(12) United States Patent
Nair

(10) Patent No.: US 11,596,469 B2
(45) Date of Patent: *Mar. 7, 2023

(54) DEVICE, SYSTEM, AND METHOD FOR IMAGING AND TISSUE CHARACTERIZATION OF ABLATED TISSUE

(71) Applicant: Volcano Corporation, San Diego, CA (US)

(72) Inventor: Anuja Nair, Bedford, MA (US)

(73) Assignee: PHILIPS IMAGE GUIDED THERAPY CORPORATION, San Diego, CA (US)

(*) Notice: Subject to any disclaimer, the term of this patent is extended or adjusted under 35 U.S.C. 154(b) by 908 days.

This patent is subject to a terminal disclaimer.

(21) Appl. No.: 15/483,925

(22) Filed: Apr. 10, 2017

(65) Prior Publication Data

US 2017/0215952 A1     Aug. 3, 2017

Related U.S. Application Data

(63) Continuation of application No. 14/137,393, filed on Dec. 20, 2013, now Pat. No. 9,615,878.
(Continued)

(51) Int. Cl.
*A61B 18/12*     (2006.01)
*A61B 18/14*     (2006.01)
(Continued)

(52) U.S. Cl.
CPC ........ *A61B 18/1492* (2013.01); *A61B 8/0891* (2013.01); *A61B 8/12* (2013.01); *A61N 7/022* (2013.01); *A61B 5/0075* (2013.01); *A61B 2018/00214* (2013.01); *A61B 2018/00267* (2013.01); *A61B 2018/00404* (2013.01);
(Continued)

(58) Field of Classification Search
CPC ..... A61B 18/1492; A61B 8/12; A61B 8/0891; A61B 2090/3784; A61B 2090/3735; A61B 2018/00577; A61B 2018/00511; A61B 2018/00434; A61B 2018/00404;
(Continued)

(56) References Cited

U.S. PATENT DOCUMENTS 4,917,097 A    4/1990   Eberle
5,368,037 A    11/1994   Eberle
(Continued)

*Primary Examiner* — Jaymi E Della

(57) ABSTRACT

Disclosed herein is a system for ablating and characterizing tissue. The system comprises an ablation element configured to emit ablative energy toward a tissue of interest, an imaging apparatus configured to emit energy and collect imaging data including reflected signals from the tissue of interest, and a characterization application. The characterization application comprises a signal analyzer for analyzing the imaging data and determining one or more signal properties from the reflected signals, and a correlation processor configured to associate the one or more signal properties to pre-determined tissue signal properties of different tissue components through a pattern recognition technique. The pre-determined tissue signal properties are embodied in a database, and the correlation processor is configured to identify a tissue component and an ablation level of the tissue of interest based on the pattern recognition technique.

17 Claims, 22 Drawing Sheets

Related U.S. Application Data

(60) Provisional application No. 61/745,476, filed on Dec. 21, 2012.

(51) Int. Cl.
  *A61N 7/02* (2006.01)
  *A61B 8/08* (2006.01)
  *A61B 8/12* (2006.01)
  *A61B 18/00* (2006.01)
  *A61B 90/00* (2016.01)
  *A61B 5/00* (2006.01)

(52) U.S. Cl.
  CPC ............ *A61B 2018/00434* (2013.01); *A61B 2018/00511* (2013.01); *A61B 2018/00577* (2013.01); *A61B 2018/00684* (2013.01); *A61B 2018/126* (2013.01); *A61B 2018/1253* (2013.01); *A61B 2090/3735* (2016.02); *A61B 2090/3784* (2016.02)

(58) Field of Classification Search
  CPC .......... A61B 2018/00267; A61B 2018/00214; A61N 7/022
  See application file for complete search history.

(56) References Cited

U.S. PATENT DOCUMENTS

| | | | |
|---|---|---|---|
| 5,453,575 A | 9/1995 | Eberle | |
| 5,603,327 A | 2/1997 | Eberle | |
| 5,779,644 A | 7/1998 | Eberle | |
| 5,857,974 A | 1/1999 | Eberle | |
| 5,876,344 A | 3/1999 | Baker | |
| 5,921,931 A | 7/1999 | Bleam | |
| 5,938,615 A | 8/1999 | Eberle | |
| 6,033,357 A | 3/2000 | Ciezki | |
| 6,049,958 A | 4/2000 | Eberle | |
| 6,123,673 A | 9/2000 | Eberle | |
| 6,165,128 A | 12/2000 | Cespedes | |
| 6,283,920 B1 | 9/2001 | Eberle | |
| 6,309,339 B1 | 10/2001 | Ciezki | |
| 6,381,350 B1 | 4/2002 | Klingensmith | |
| 6,457,365 B1 | 10/2002 | O'Donnell | |
| 6,712,767 B2 | 3/2004 | Hossack | |
| 6,725,081 B2 | 4/2004 | Ciezki | |
| 6,767,327 B1 | 7/2004 | Corl | |
| 6,776,763 B2 | 8/2004 | Dickinson | |
| 6,779,257 B2 | 8/2004 | Brunicardi | |
| 6,785,415 B1 | 8/2004 | Kido | |
| 6,899,682 B2 | 5/2005 | Eberle | |
| 6,962,567 B2 | 11/2005 | Eberle | |
| 6,976,965 B2 | 12/2005 | Corl | |
| 7,097,620 B2 | 8/2006 | Corl | |
| 7,226,417 B1 | 6/2007 | Eberle | |
| 7,676,910 B2 | 3/2010 | Brunicardi | |
| 7,711,413 B2 | 5/2010 | Castella | |
| 7,736,317 B2 | 6/2010 | O'Donnell | |
| 9,615,878 B2 * | 4/2017 | Nair | A61B 8/12 |
| 2002/0107512 A1 | 8/2002 | Edwards | |
| 2003/0195504 A1 * | 10/2003 | Tallarida | A61B 18/1492 606/41 |
| 2004/0176699 A1 | 9/2004 | Flores | |
| 2006/0089556 A1 * | 4/2006 | Bambot | A61B 5/0071 600/476 |
| 2006/0241577 A1 * | 10/2006 | Balbierz | A61B 18/1206 606/32 |
| 2007/0149967 A1 * | 6/2007 | Chapelon | A61B 18/1492 606/41 |
| 2008/0161801 A1 | 7/2008 | Kelleher | |
| 2008/0262489 A1 | 10/2008 | Steinke | |
| 2010/0152590 A1 * | 6/2010 | Moore | A61B 1/00082 600/466 |
| 2010/0168572 A1 * | 7/2010 | Sliwa | A61B 18/1492 600/439 |
| 2010/0292571 A1 | 11/2010 | Dighe | |
| 2011/0106074 A1 | 5/2011 | Ascondeguy | |
| 2011/0251487 A1 | 10/2011 | Bowden | |
| 2012/0165667 A1 * | 6/2012 | Altmann | A61B 18/1492 600/439 |
| 2012/0265192 A1 * | 10/2012 | Sliwa | A61B 8/5223 606/33 |
| 2013/0116511 A1 | 5/2013 | Sui | |
| 2013/0216114 A1 | 8/2013 | Courtney | |
| 2013/0289369 A1 | 10/2013 | Margolis | |

* cited by examiner

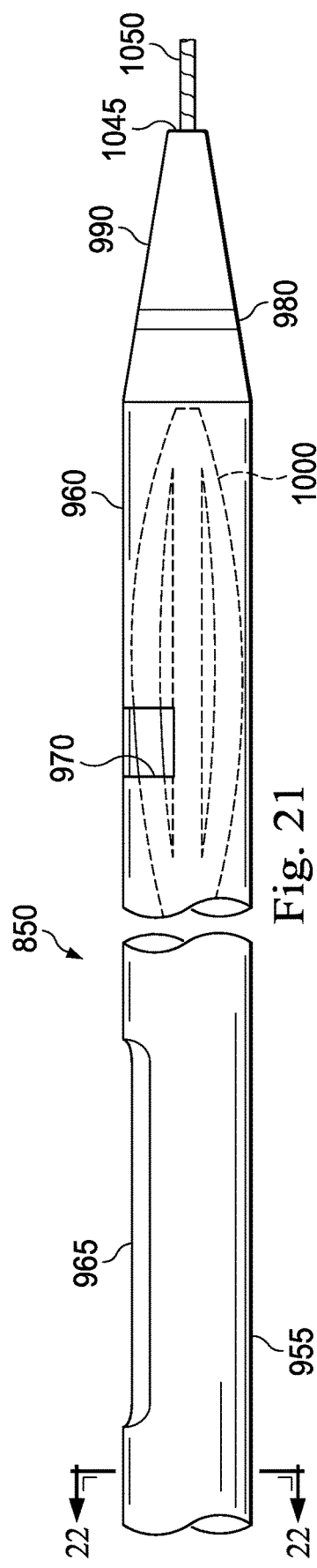
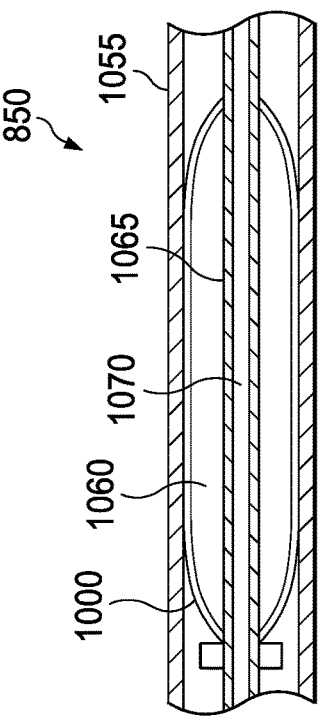
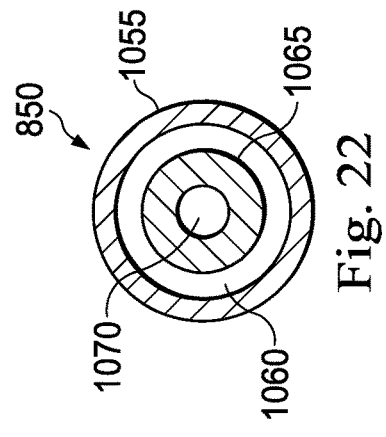

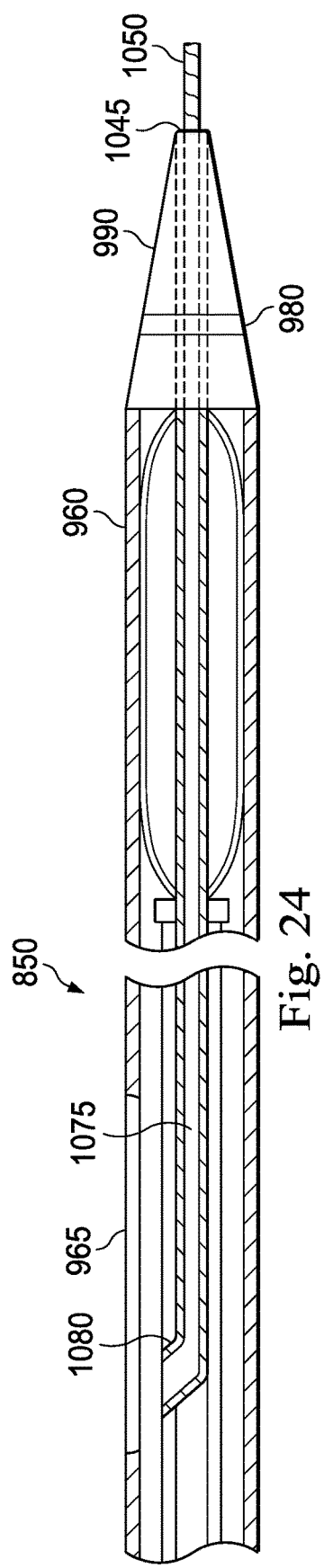
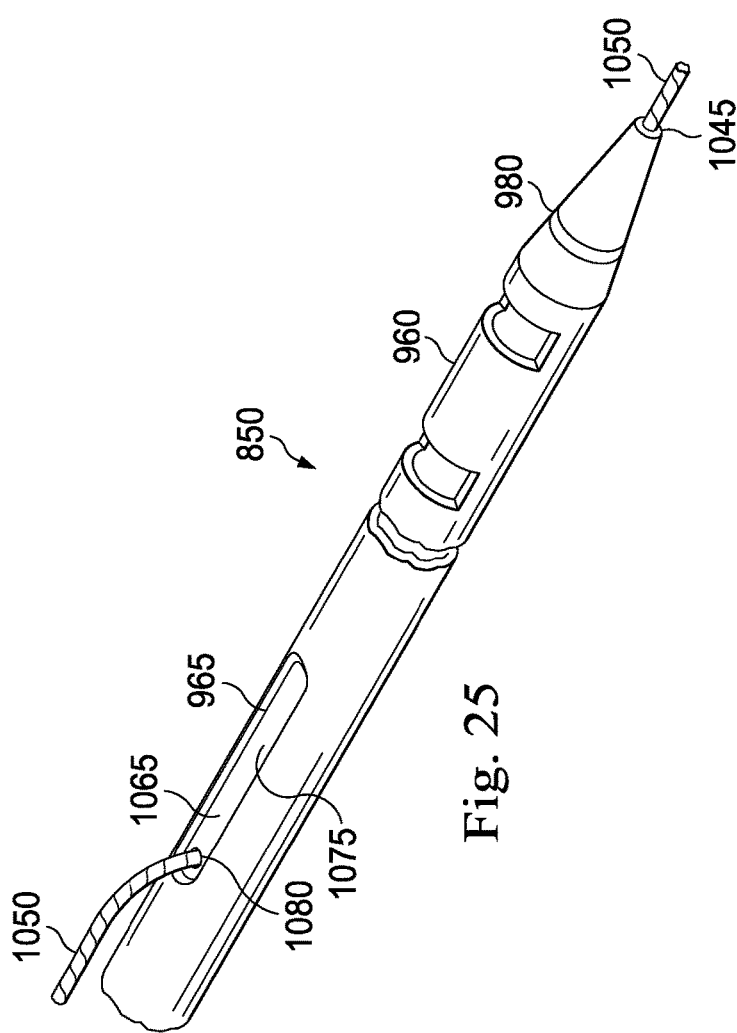

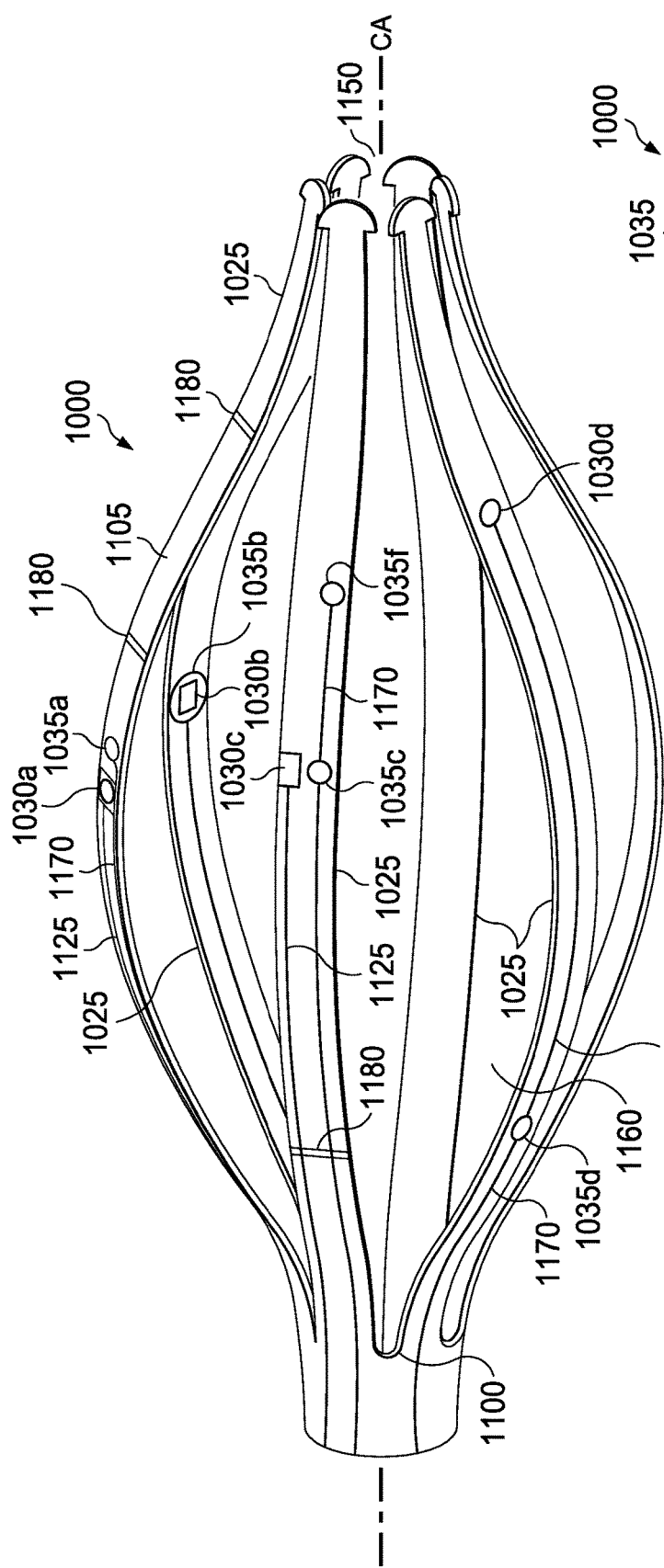
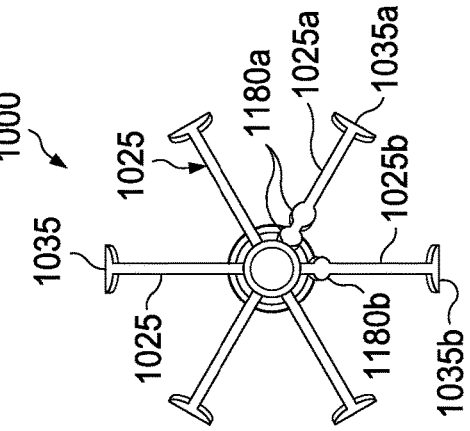
Fig. 27
Fig. 28

DEVICE, SYSTEM, AND METHOD FOR IMAGING AND TISSUE CHARACTERIZATION OF ABLATED TISSUE

CROSS-REFERENCE TO RELATED APPLICATIONS

The present application is a continuation of U.S. application Ser. No. 14/137,393, filed Dec. 20, 2013, now U.S. Pat. No. 9,615,878, which claims priority to and the benefit of U.S. Provisional Patent Application No. 61/745,476, filed Dec. 21, 2012, each of which is hereby incorporated by reference in its entirety.

FIELD OF THE INVENTION

The present disclosure relates generally to tissue ablation procedures and imaging with tissue characterization to guide the ablation therapy.

BACKGROUND

Ablation therapy is utilized throughout the body to disrupt unwanted tissues of a patient. In one example, ablation catheters can be used to create tissue necrosis to treat a variety of health conditions, including cardiovascular conditions such as cardiac arrhythmias. A common cause of cardiac arrhythmias is the abnormal routing of electricity through the cardiac tissue. Thus, arrhythmias can be treated by ablating suspected areas of electrical misfiring, thereby inactivating such aberrant firing. An ablation catheter can apply ablative energy (e.g., without limitation, radiofrequency (RF) energy, cryoablation, lasers, chemicals, high-intensity focused ultrasound (HIFU)) to target tissues to purposefully create lesions in an effort to disrupt undesirable electrical and/or neural pathways to limit or prevent the aberrant signals that lead to the underlying conditions. In some instances, the ablation catheter ablates sufficient target and surrounding tissue to create non-conductive barriers to the progression of aberrant electrical activity through the cardiac tissue. In particular, ablation therapy using RF waves on cardiac tissue is used to cure a variety of cardiac arrhythmias such as, without limitation, supraventricular tachycardia, Wolff-Parkinson-White syndrome (WPW), ventricular tachycardia, atrial fibrillation, atrial flutter, and ectopic atrial tachycardia.

The ablative energy must be directed such that the target tissue is ablated without unduly injuring the surrounding tissue. In some instances, the ablation procedure can cause undesirable charring of adjacent tissue and localized coagulation. A difficulty associated with ablation procedures stems from a healthcare provider's lack of real-time knowledge over the size, shape, and depth of the treated region. Such uncertainty can make it difficult for the healthcare provider to monitor the degree to which the tissue has been ablated, which makes it difficult to determine when to stop, reduce, or redirect the application of ablative energy.

Currently, lesions are evaluated following the ablation procedure. In some instances following a cardiac ablation procedure, a physician will evaluate the lesions through electrophysiologic mapping by positioning a catheter in the heart to measure the remaining electrical activity and determine whether the lesions have created a nonconductive pathway that is adequately halting aberrant conductivity. Conventional mapping techniques used during ablation procedures require the clinician to manually mark treated regions on an anatomical map. If it is established that the lesions were inadequately formed, then additional lesions may be created to complete the nonconductive pathway and address the aberrant conductivity. However, this post-ablation evaluation entails further medical procedures and extends the time required to treat the patient's underlying condition. Moreover, the anatomical marking may be affected by numerous variables, including movement of the target tissue and/or the catheter due to cardiac contractions and ventilation. Thus, there may not be strong correlation between the lesions marked on the anatomical map and the effective delivery of ablative therapy.

One method of evaluating lesions as they are formed is to measure the electrical impedance and/or the temperature of the target tissue and surrounding tissues. Biochemical differences between ablated and normal tissues can result in changes in electrical impedance between the tissue types. In general, impedance measurements are roughly correlated with impedance measurements. Though impedance is routinely monitored during electrophysiologic therapy, however, it is not directly related to lesion formation. Measuring impedance provides data as to the location of the ablated tissue, but it does not provide any qualitative, real-time data about the character of the ablated tissue to enable evaluation of the effectiveness of the lesion or the degree of ablation.

Another approach is lesion pacing, where the healthcare provider can measure the electrical conductance between two points of tissue bridging the lesion. However, lesion pacing only measures the effectiveness of the lesion in creating a nonconductive area. It does not provide any qualitative data about the character of the ablated tissue or the degree of ablation.

The devices, systems, and methods disclosed herein overcome one or more of the deficiencies of the prior art.

SUMMARY

In one aspect, the present disclosure provides a system and method for performing an ablation procedure on a patient's tissue while utilizing active tissue characterization to at least in part guide the ablation therapy. Among other features, the tissue characterization information can assist the user in one or more of the following: evaluation of tissue to be ablated, the amount of energy to utilize, the extent of the area to be ablated, damage to adjacent tissue, the direction of the tissue to be ablated, and the depth of ablation.

In one embodiment, the present disclosure provides a system for ablating and characterizing tissue within the ablation zone. The system can include an ablation element configured to emit ablative energy toward a tissue of interest and an imaging apparatus configured to emit energy and collect imaging data including reflected signals from the tissue of interest. The system also includes a characterization application having a signal analyzer for analyzing the imaging data and determining one or more signal properties from the reflected signals; and a correlation processor configured to associate the one or more signal properties to pre-determined tissue signal properties of different tissue components through a pattern recognition technique. In one aspect, the pre-determined tissue signal properties are embodied in a database, and the correlation processor is further configured to identify a tissue component and an ablation level of the tissue of interest based on the pattern recognition technique. In another aspect, the ablation element is expandable.

In another embodiment, the present disclosure provides a method of ablating and characterizing one or more tissue components of a scanned tissue zone in a patient. The method comprises positioning a device including an ablative element and an imaging apparatus adjacent a region of interest of the scanned tissue zone. The method continues by directing ablative energy from an ablative element toward the region of interest, receiving reflected signals from an imaging apparatus scanning the region of interest, determining one or more signal properties of the region of interest from the reflected signals, and associating the one or more signal properties to pre-determined signal properties of tissue components of an tissue similar to the scanned tissue zone wherein the pre-determined signal properties comprise classification conditions stored in a data structure. The method includes identifying one or more tissue components and their corresponding levels of ablation based on the associating. In one aspect, the positioning can include inserting a catheter device into a patient through a natural orifice or through an opening formed in the skin.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments of the devices and methods disclosed herein and together with the description, serve to explain the principles of the present disclosure. Throughout this description, like elements, in whatever embodiment described, refer to common elements wherever referred to and referenced by the same reference number. The characteristics, attributes, functions, interrelations ascribed to a particular element in one location apply to those elements when referred to by the same reference number in another location unless specifically stated otherwise.

The figures referenced below are drawn for ease of explanation of the basic teachings of the present disclosure only; the extensions of the figures with respect to number, position, relationship and dimensions of the parts to form the preferred embodiment will be explained or will be within the skill of the art after the following description has been read and understood. Further, the exact dimensions and dimensional proportions to conform to specific force, weight, strength and similar requirements will likewise be within the skill of the art after the following description has been read and understood.

The following is a brief description of each figure used to describe the present invention, and thus, is being presented for illustrative purposes only and should not be limitative of the scope of the present invention.

Figure 1:
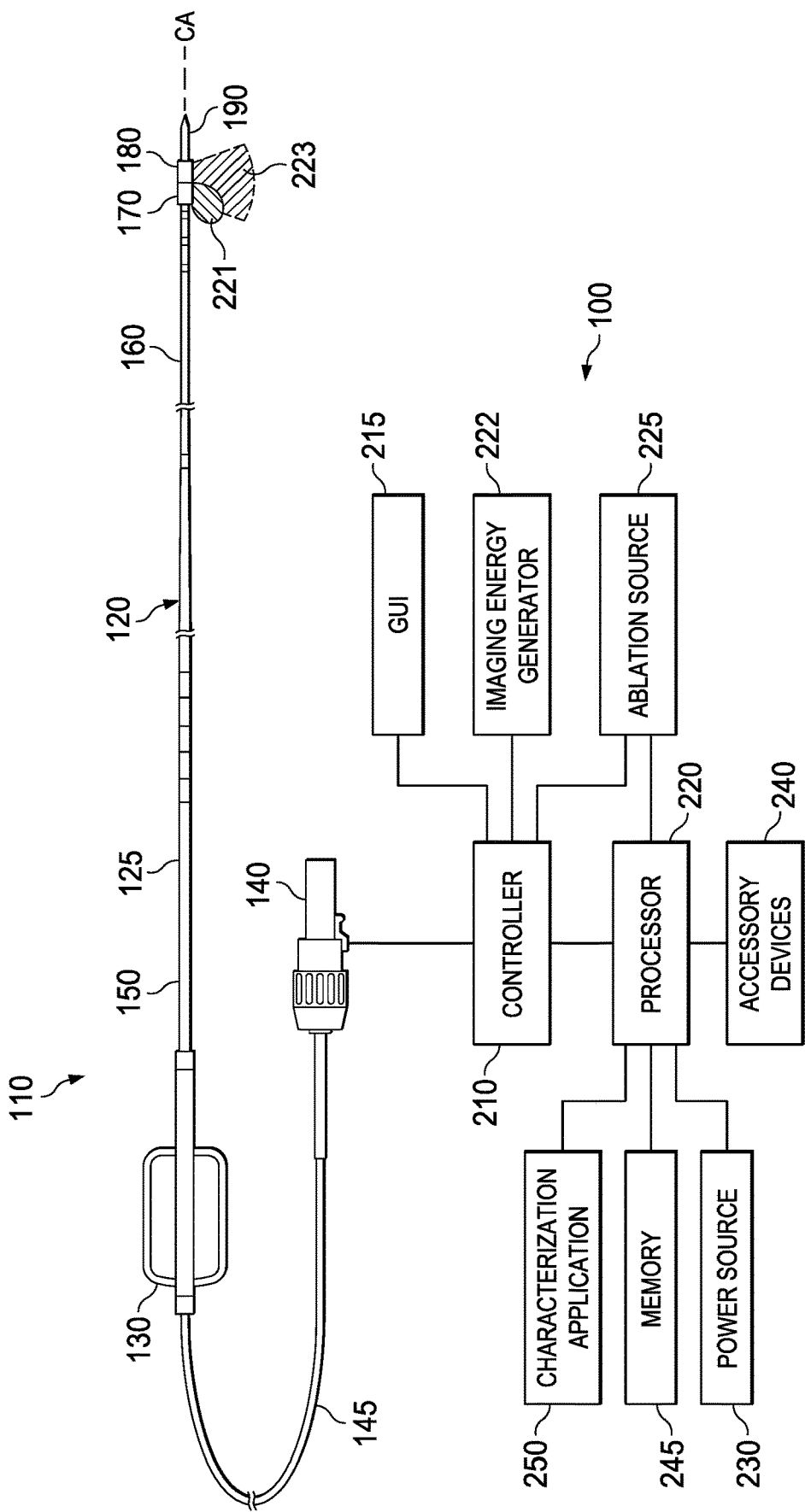

FIG. 1 is a schematic illustration of an ablation system including an ablation catheter in accordance with one embodiment of the present disclosure.

Figure 2:
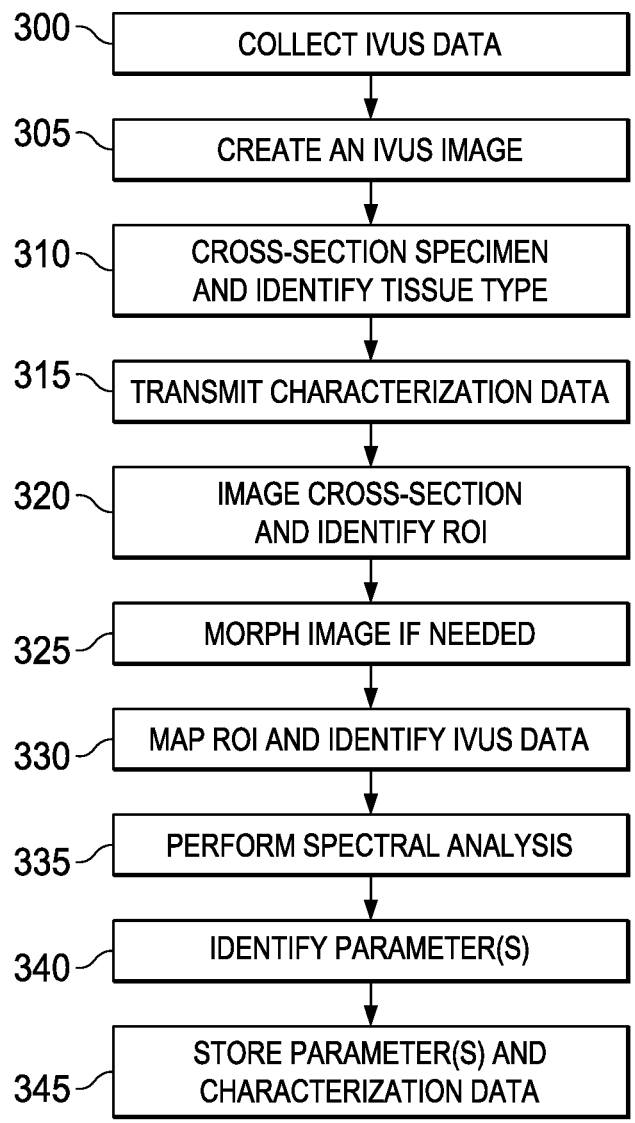

FIG. 2 illustrates an exemplary method of characterizing a specimen to populate a characterization database in accordance with one embodiment of the present disclosure.

Figure 3:
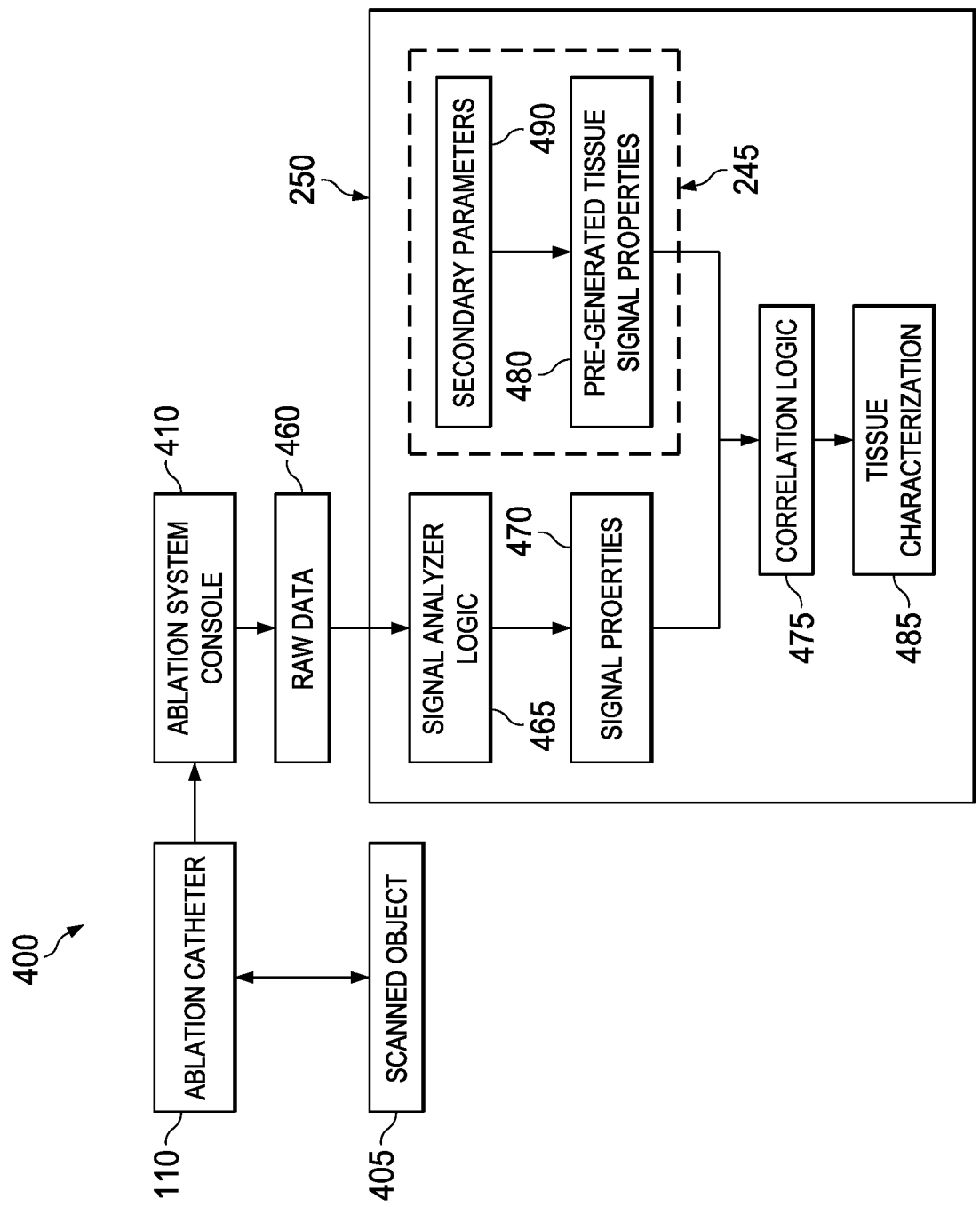

FIG. 3 is a simplified block diagram of the individual components of an exemplary ablation system according to one embodiment of the present disclosure.

Figure 4:
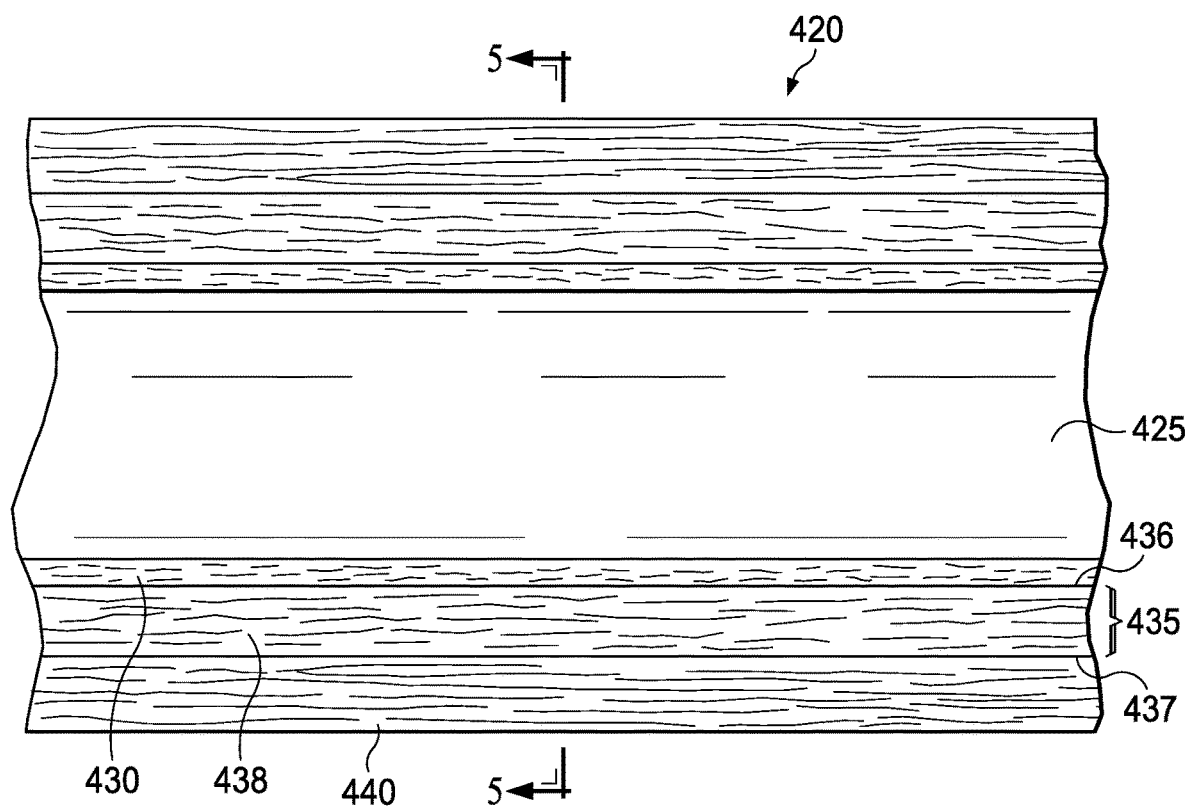

FIG. 4 is a diagrammatic, cross-sectional illustration of an unobstructed artery, showing its layers.

Figure 5:
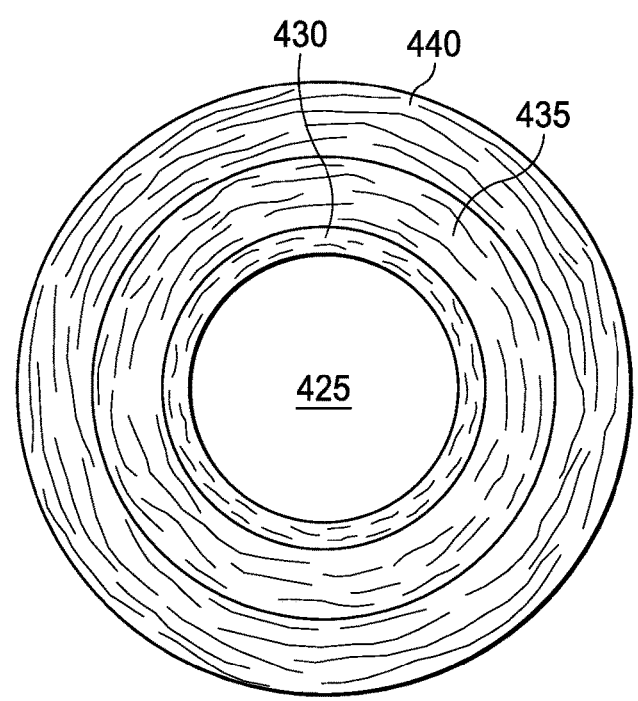

FIG. 5 is a transverse sectional illustration of the artery shown in FIG. 4 along the lines 5-5.

Figure 6:
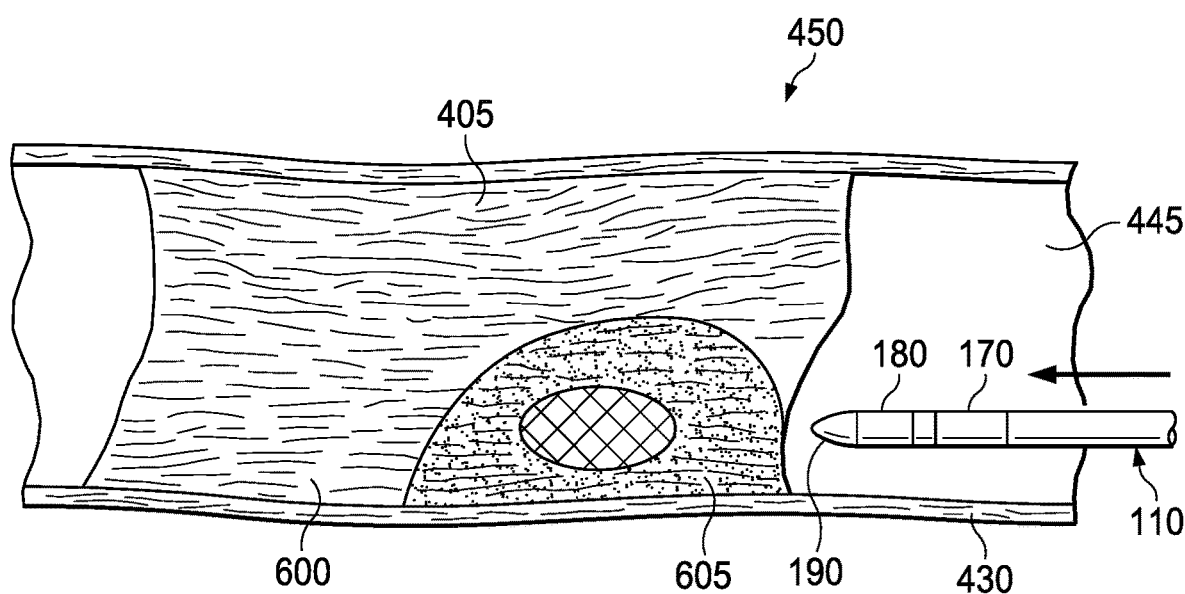

FIG. 6 is an illustration of the ablation catheter shown in FIG. 1 positioned adjacent a total occlusion within an artery according to one embodiment of the present disclosure.

Figure 7:
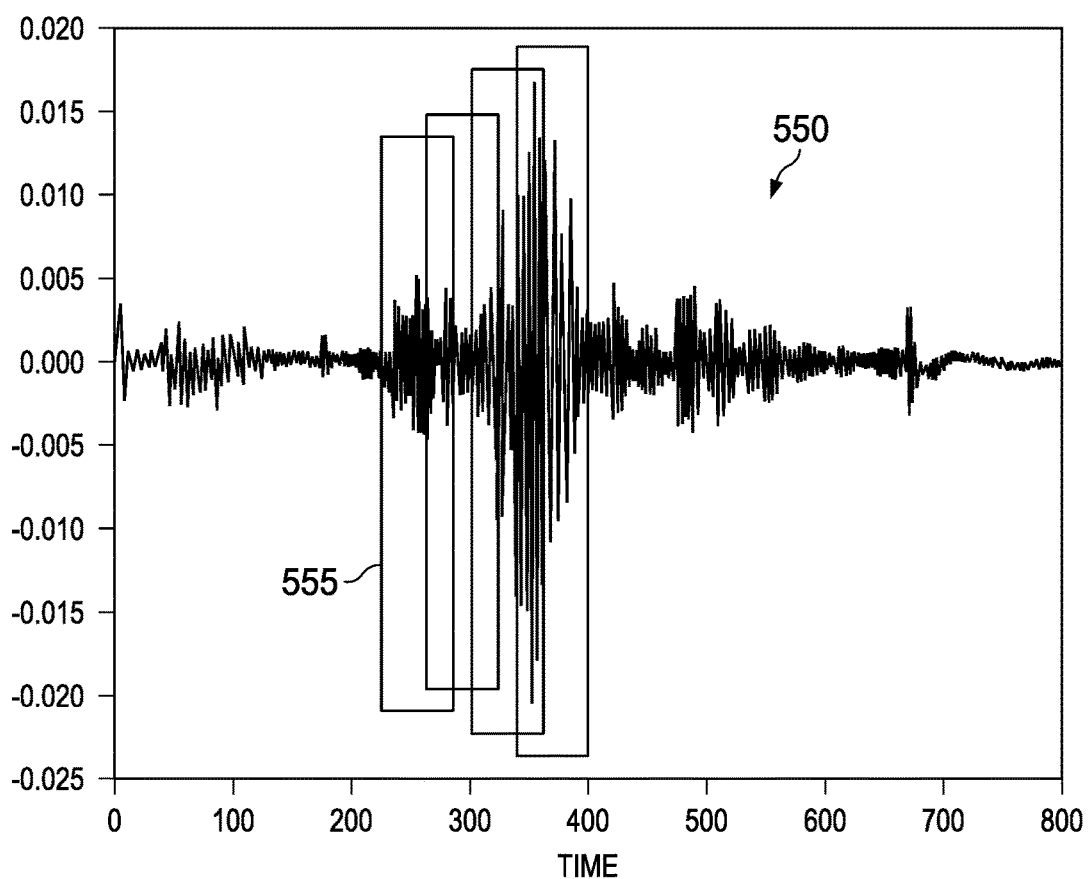

FIG. 7 is an illustration of an ultrasonic A-scan according to one embodiment of the present disclosure.

Figure 8:
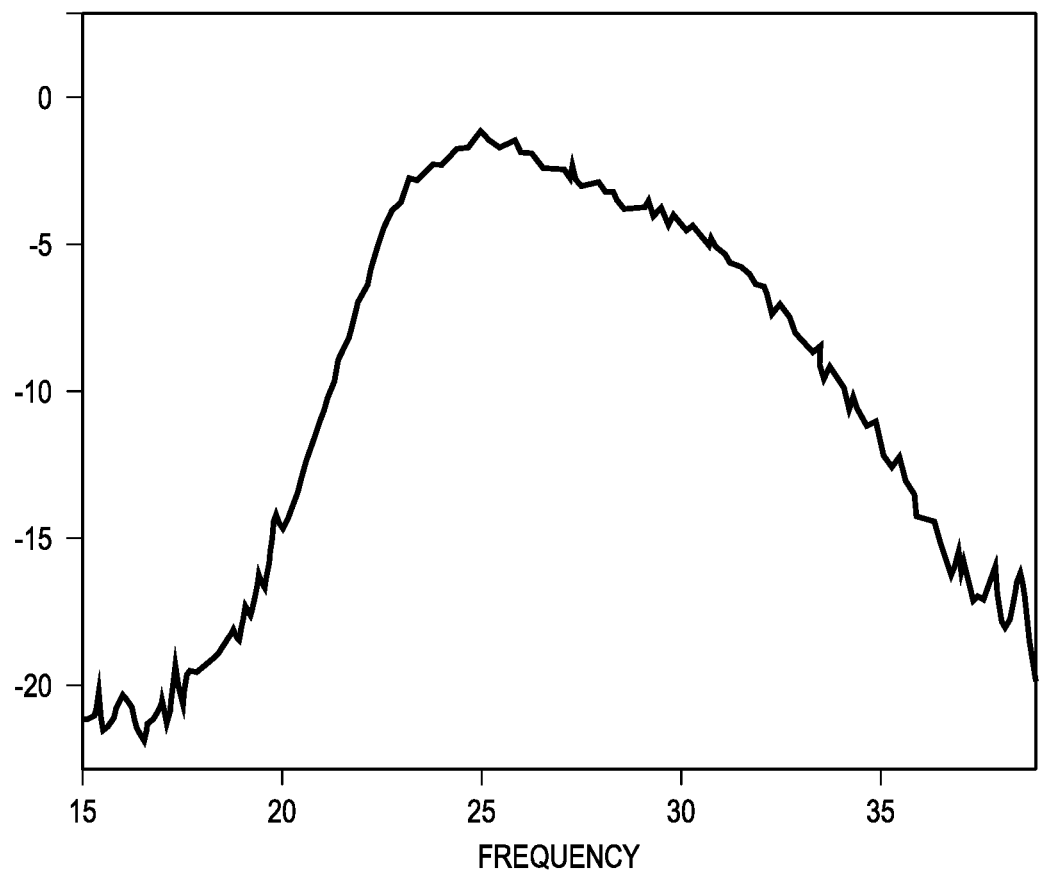

FIG. 8 is an illustration of a power spectrum plot generated from the A-scan signal shown in FIG. 7.

Figure 9:
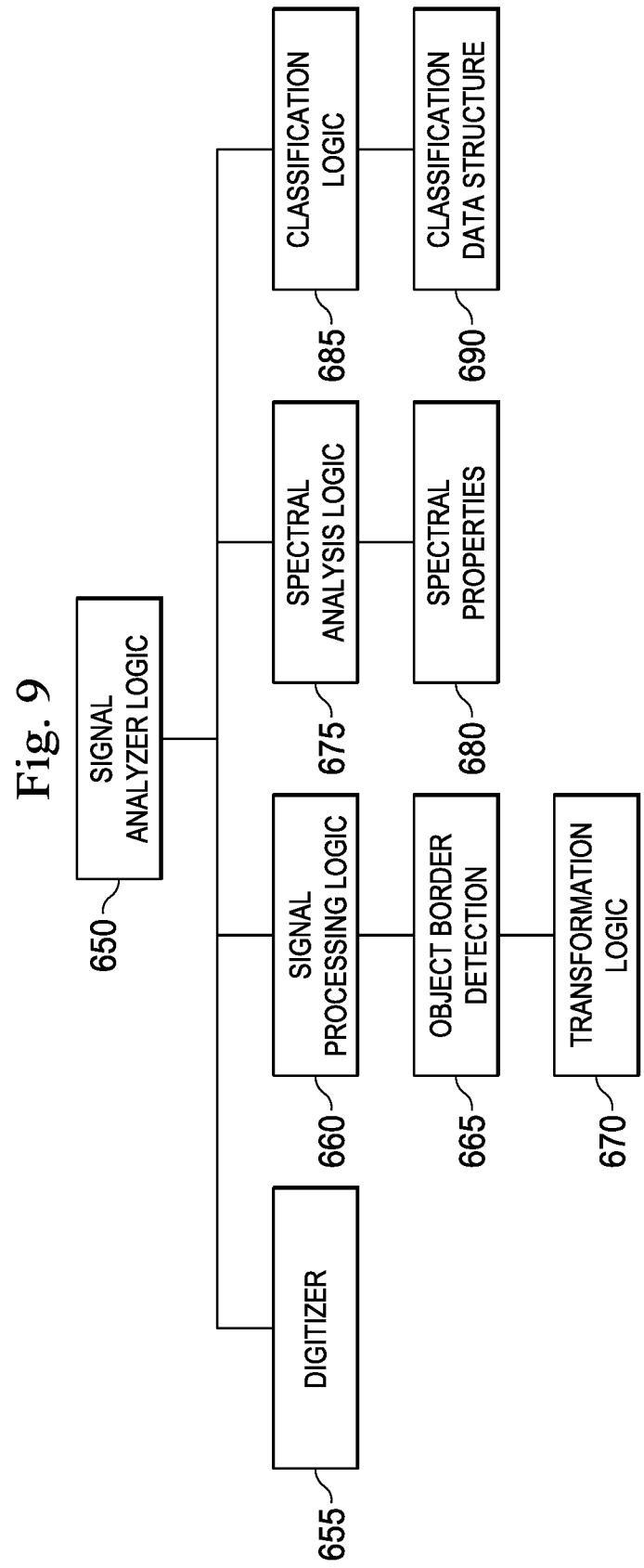

FIG. 9 is a simplified block diagram of an exemplary signal analyzer system according to one embodiment of the present disclosure.

Figure 10:
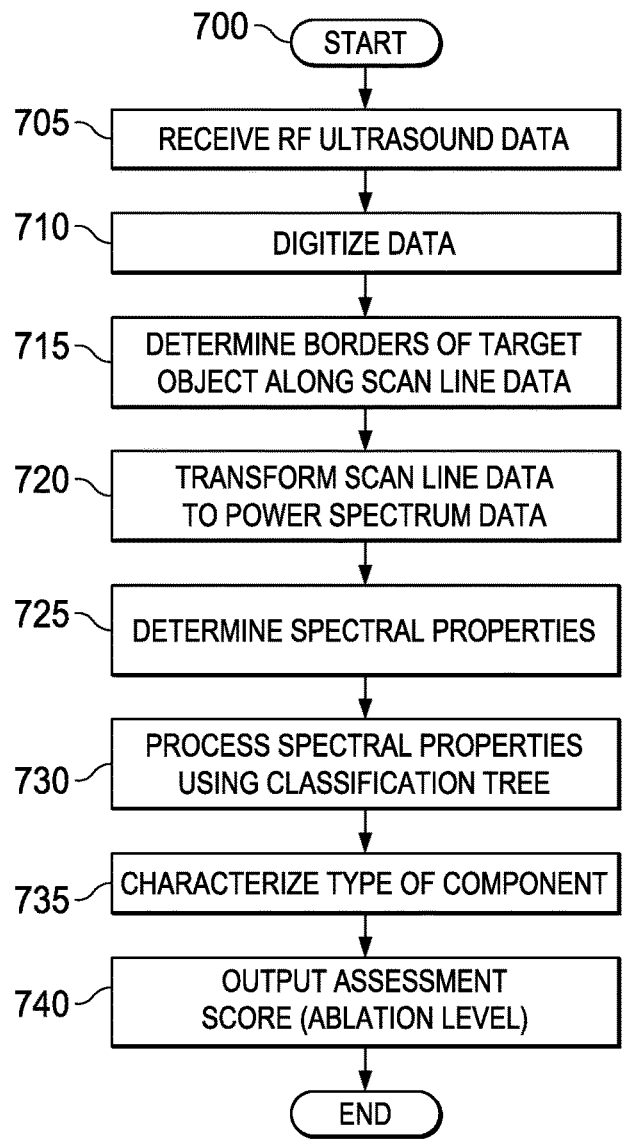

FIG. 10 is a simplified flow diagram illustrating a methodology for characterizing tissue components using the imaging system shown in FIG. 3 according to one embodiment of the present disclosure.

Figure 11:
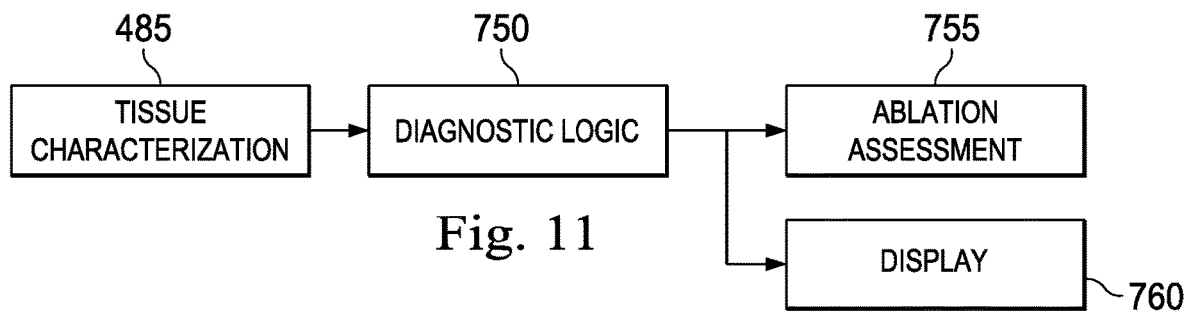

FIG. 11 is a simplified block diagram of individual components of an exemplary diagnostic system according to one embodiment of the present disclosure.

Figure 12:
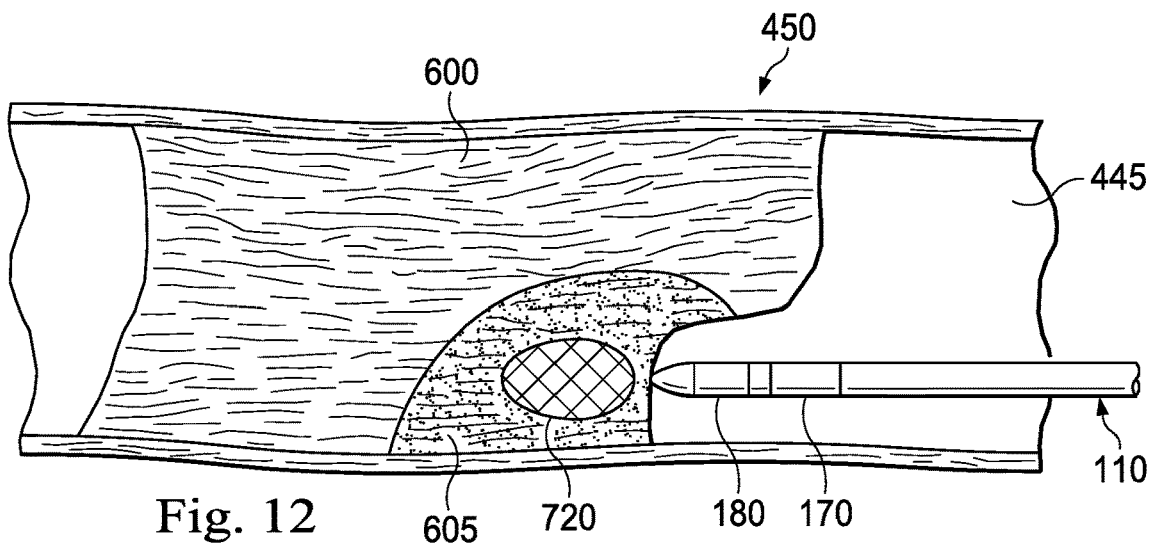
Figure 13:
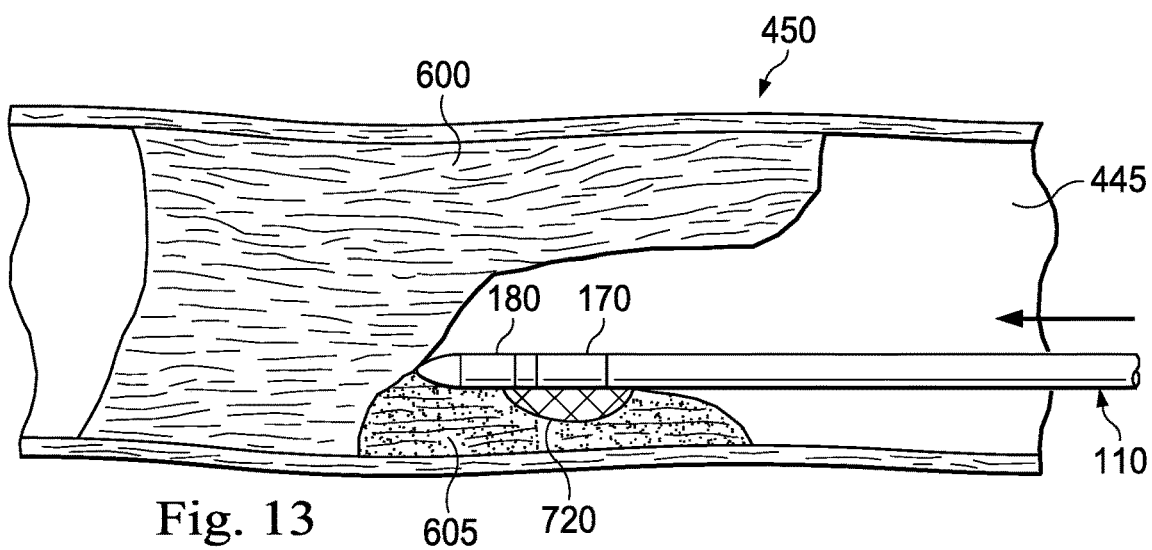
Figure 14:
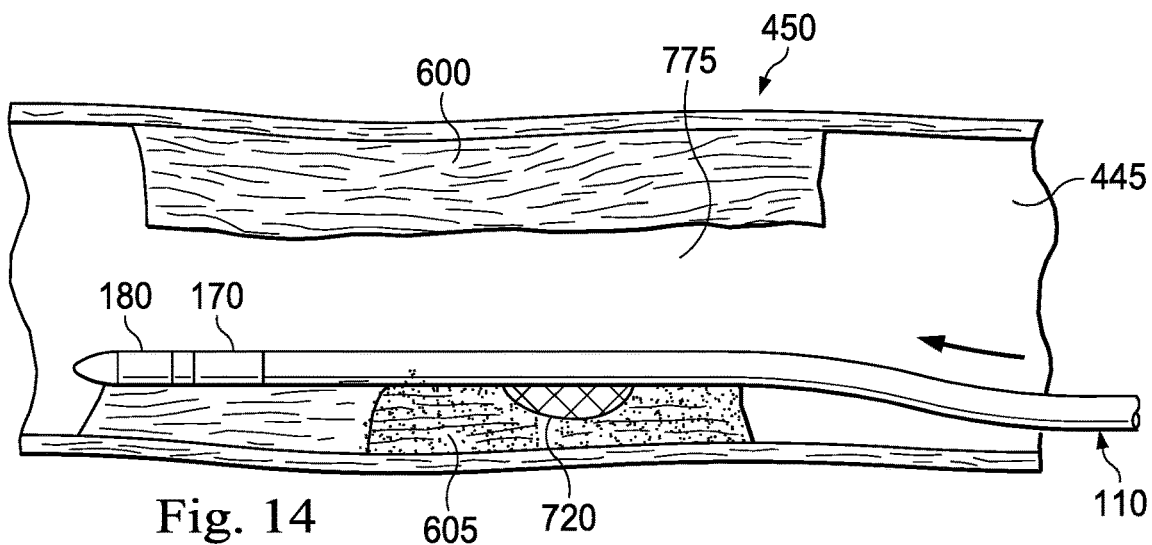

FIGS. 12-14 are illustrations of the ablation catheter shown in FIG. 1 advancing through a total occlusion within an artery according to one embodiment of the present disclosure.

Figure 15:
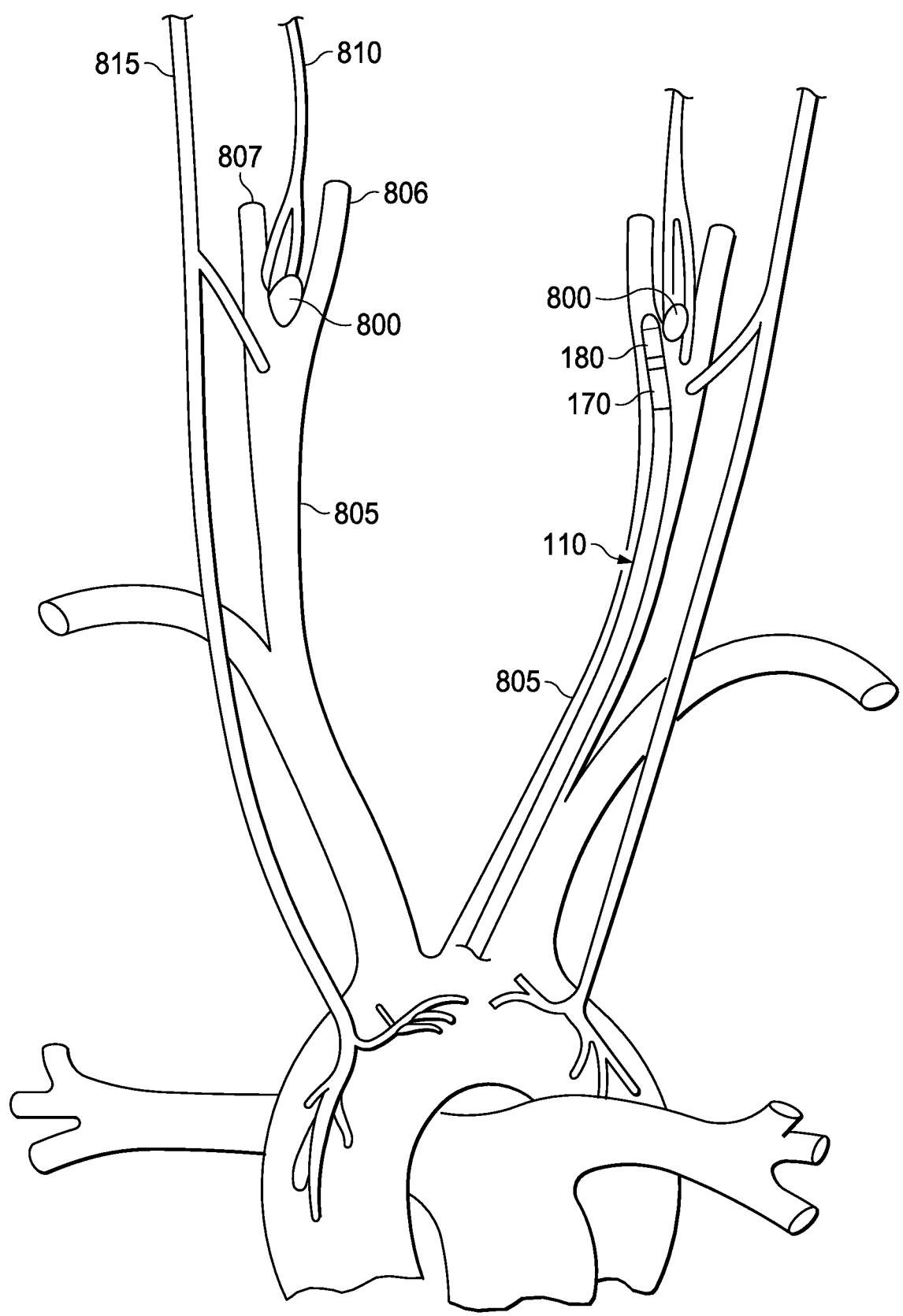

FIG. 15 is a schematic diagram illustrating an exemplary ablation catheter positioned adjacent a carotid body according to one embodiment of the present disclosure.

Figure 16:
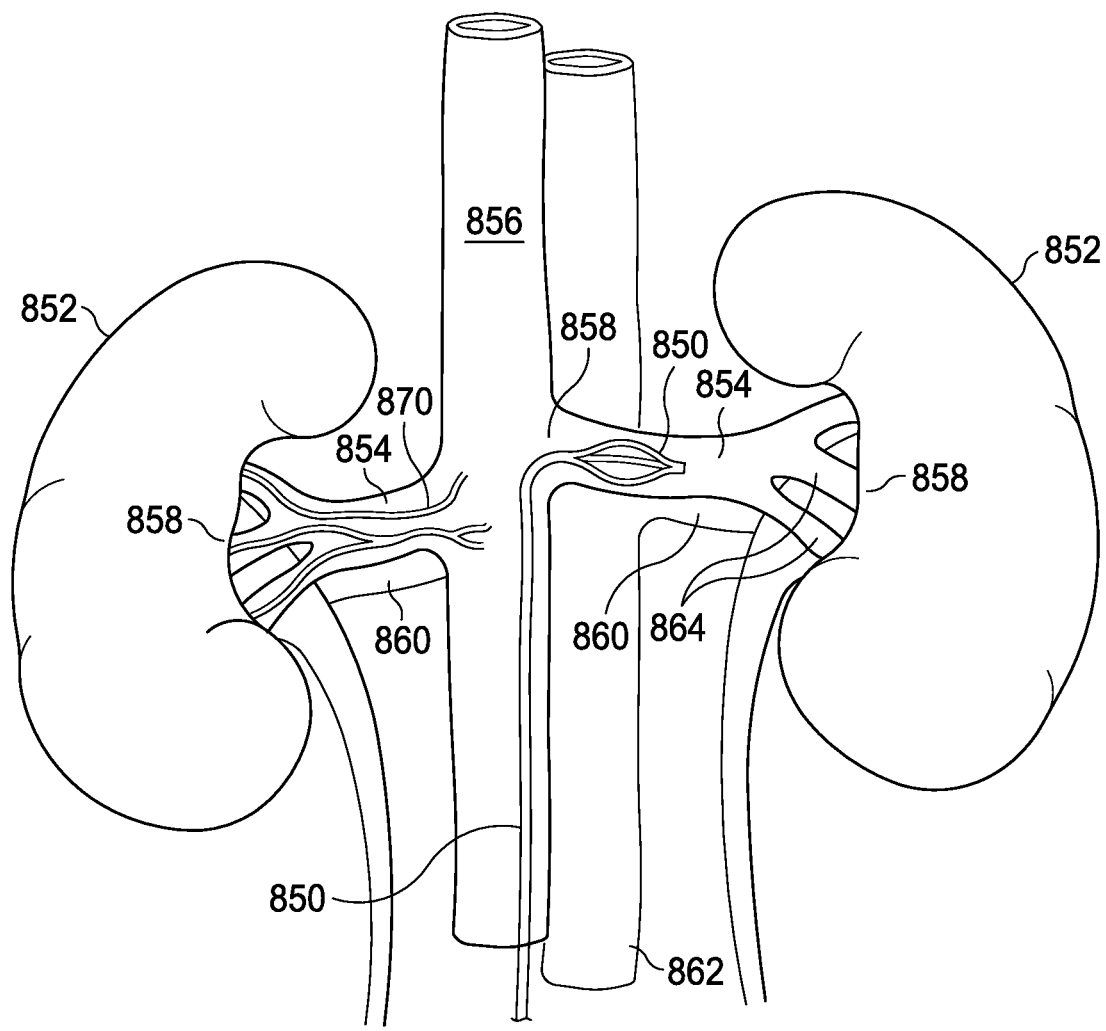

FIG. 16 is a schematic diagram illustrating an exemplary thermal basket catheter in an expanded condition positioned in the left renal artery according to one embodiment of the present disclosure.

Figure 17:
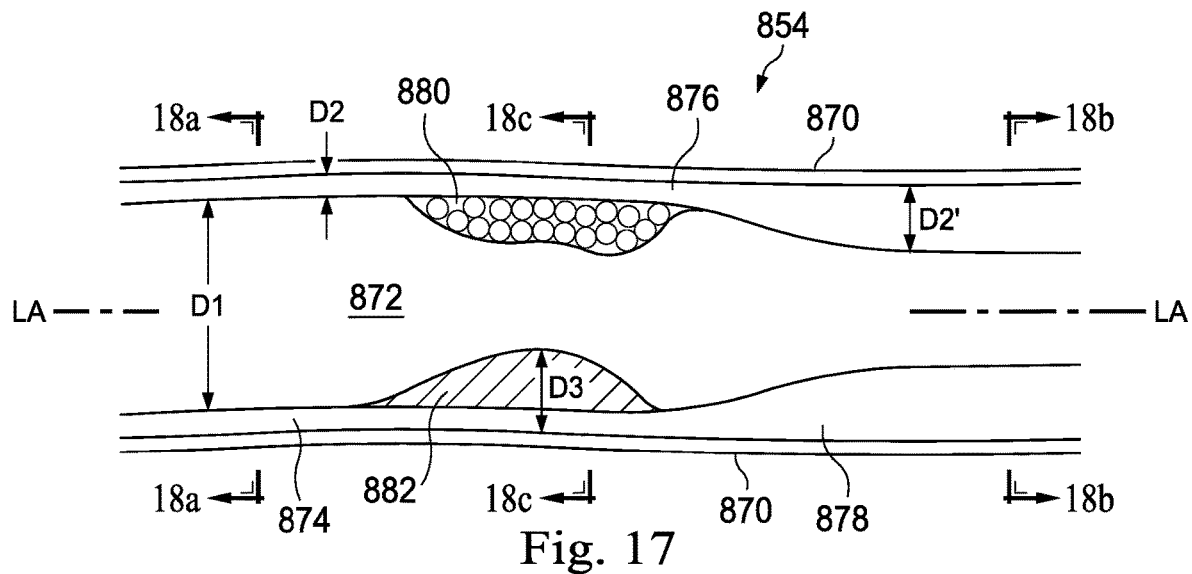

FIG. 17 is a schematic diagram illustrating a cross-sectional view of a segment of a renal artery.

Figure 18A:
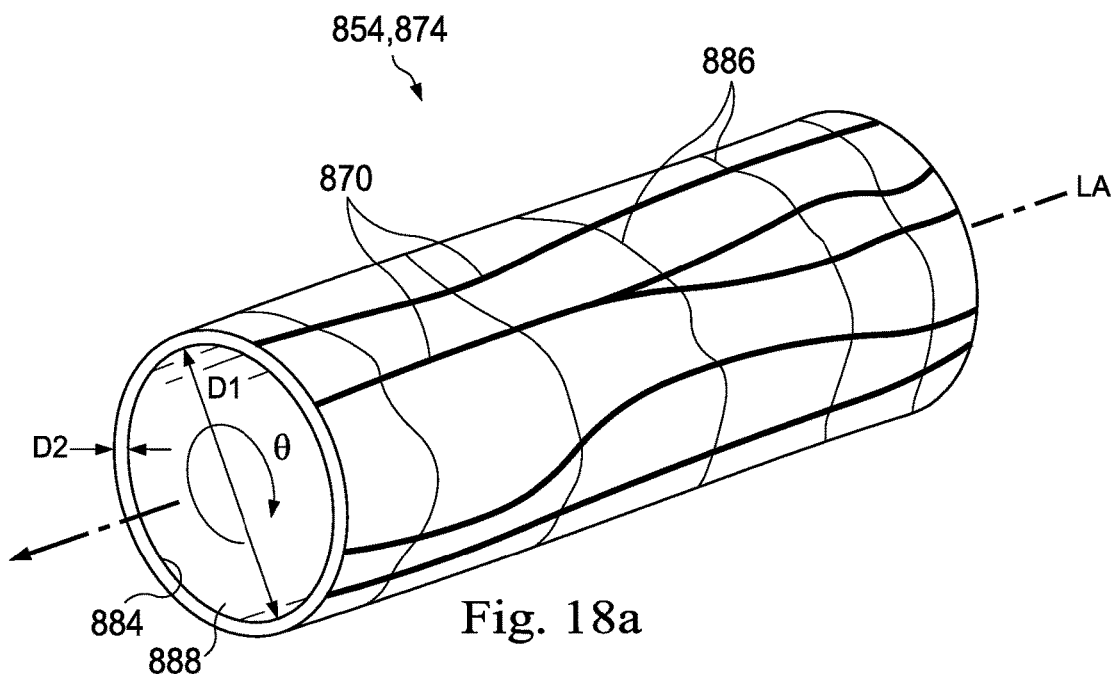

FIG. 18a is a schematic diagram illustrating a perspective view of a portion of the renal nerve plexus overlying a segment of a renal artery.

Figure 18B:
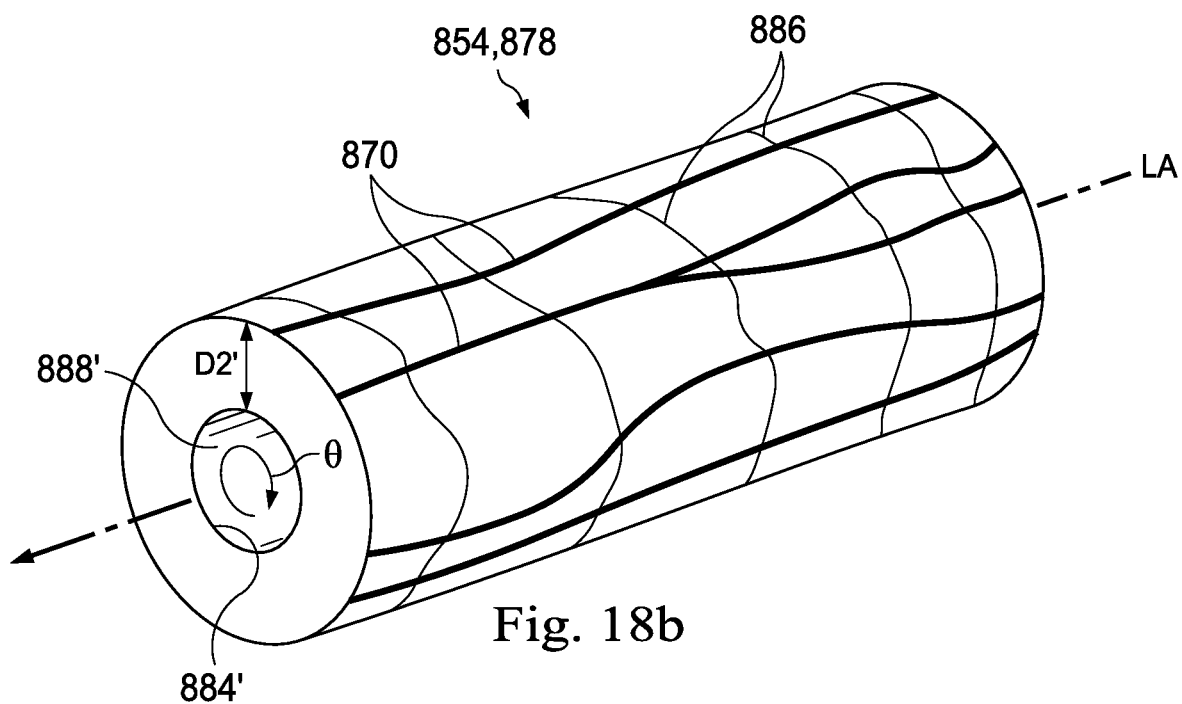

FIG. 18b is a schematic diagram illustrating a perspective view of a portion of the renal nerve plexus overlying a segment of an atherosclerotic renal artery.

Figure 18C:
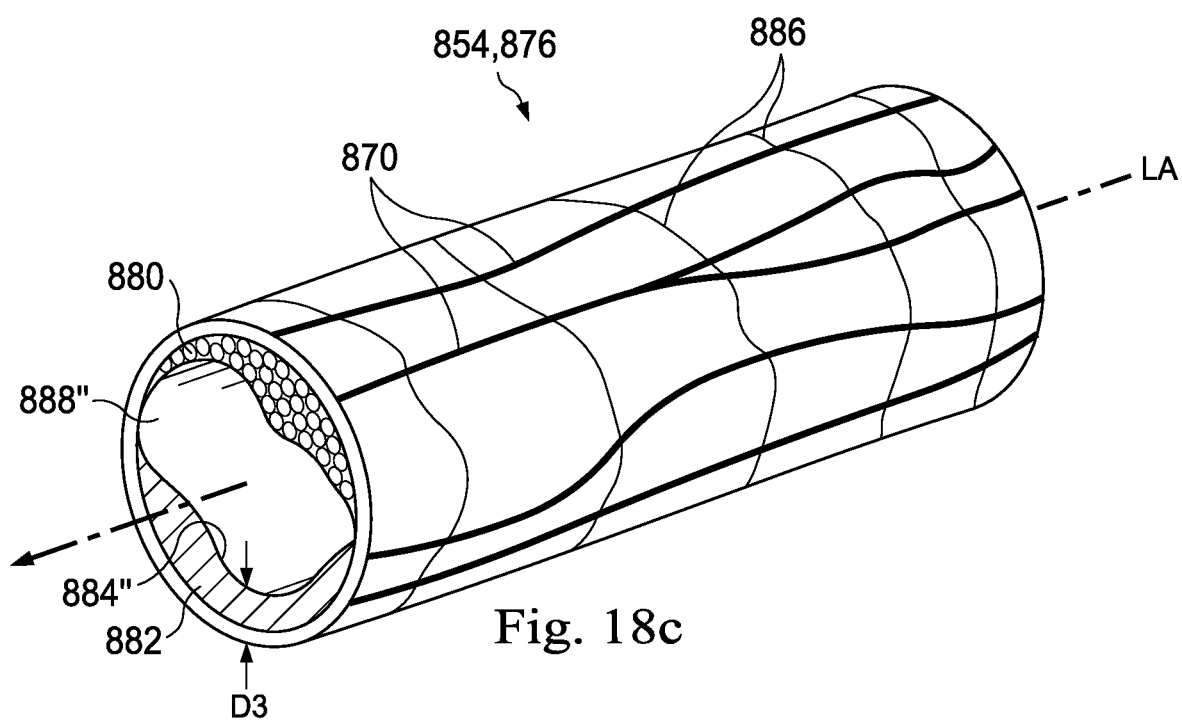

FIG. 18c is a schematic diagram illustrating a perspective view of a portion of the renal nerve plexus overlying a segment of a renal artery.

Figure 19:
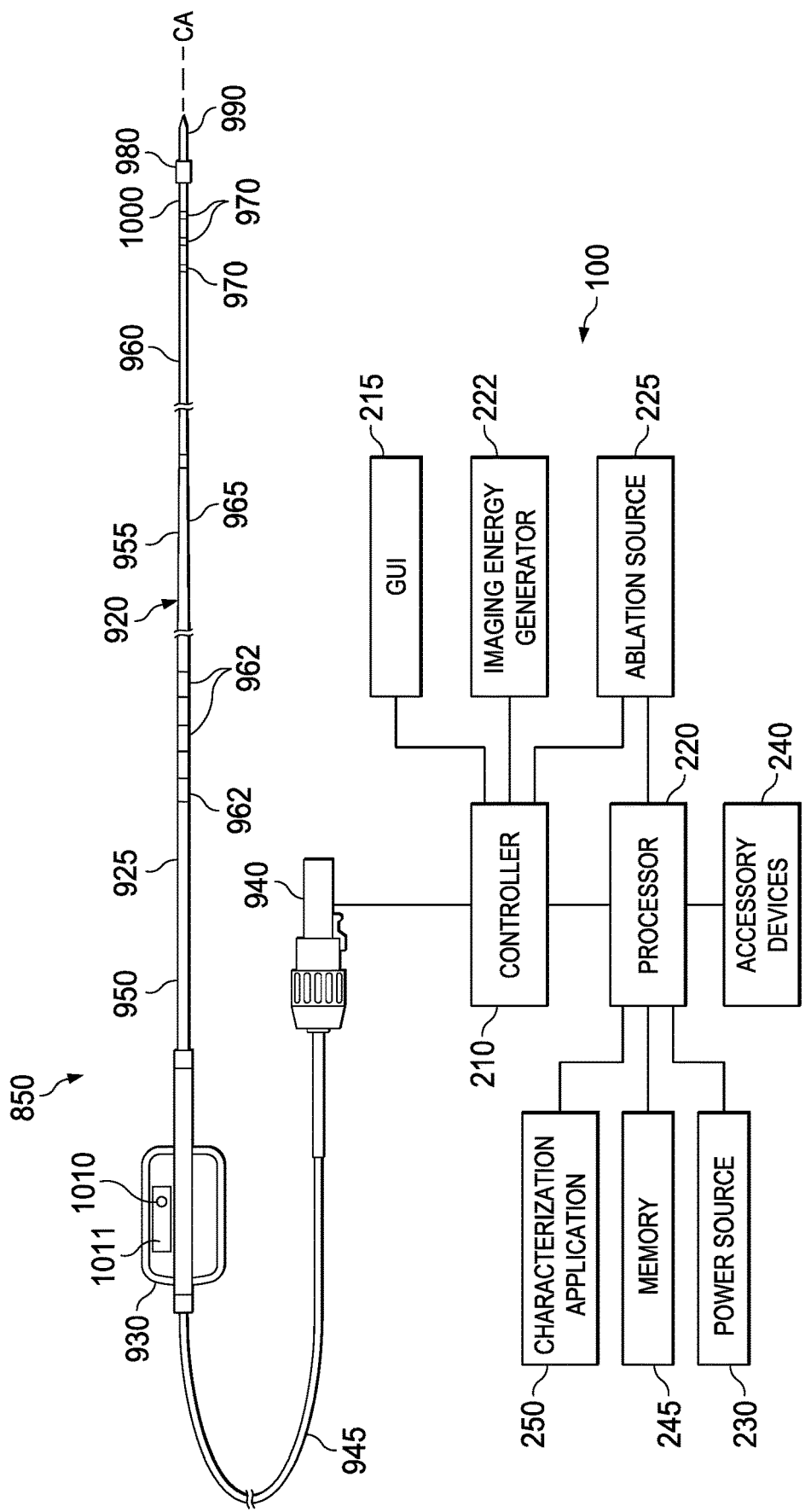

FIG. 19 is a schematic illustration of a thermal neuromodulation system including an exemplary thermal basket catheter according to one embodiment of the present disclosure.

Figure 20A:
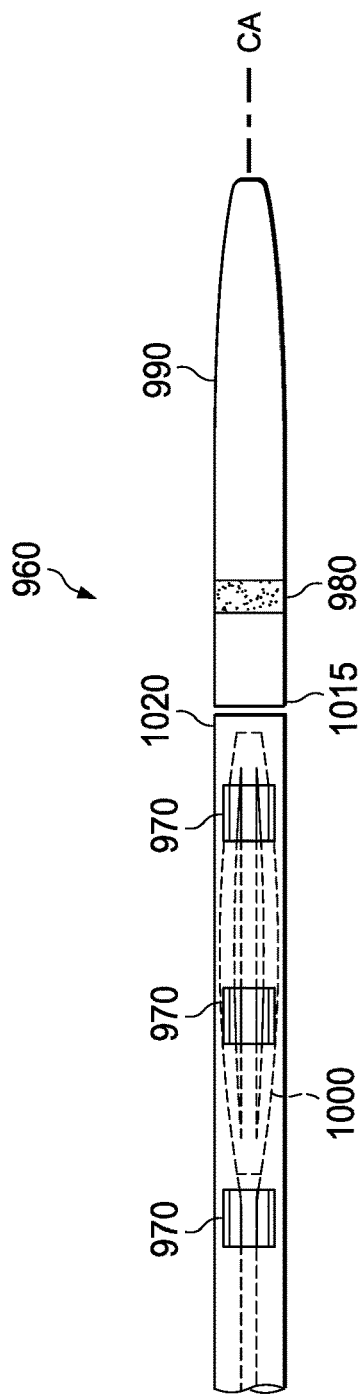

FIG. 20a is an illustration of a side view of a portion of the thermal basket catheter in an unexpanded condition according to one embodiment of the present disclosure.

Figure 20B:
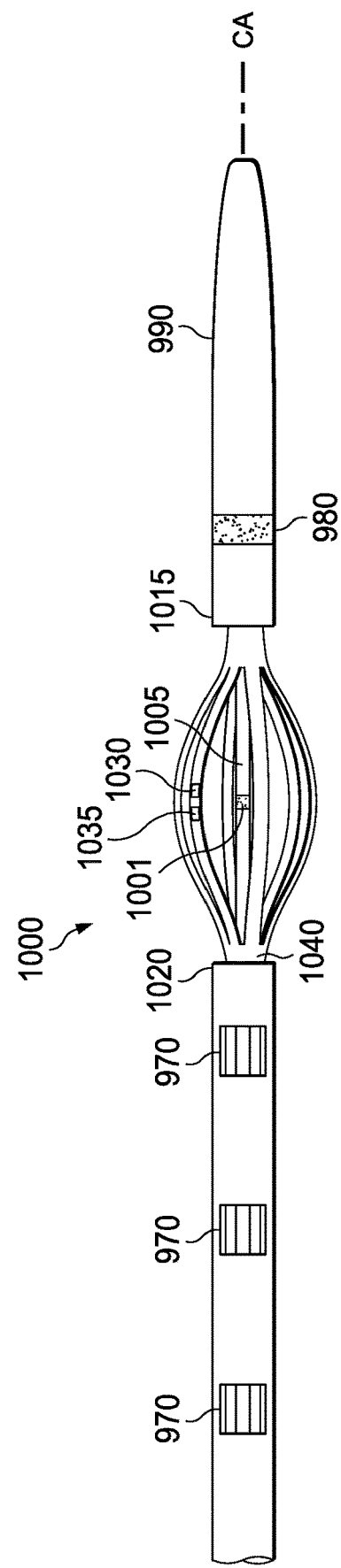

FIG. 20b is an illustration of a side view of a portion of the thermal basket catheter in an expanded condition according to one embodiment of the present disclosure.

FIG. 21 is an illustration of a partially cross-sectional side view of a portion of the thermal basket catheter in an unexpanded condition according to one embodiment of the present disclosure.

FIG. 22 is an illustration of a transverse cross-sectional view of the body of the thermal basket catheter as taken along the lines 22-22 of FIG. 21 according to one embodiment of the present disclosure.

FIG. 23 is an illustration of a cross-sectional side view of the expandable structure in a non-deployed and unexpanded condition according to one embodiment of the present disclosure.

FIG. 24 is an illustration of a cross-sectional view of a portion of the thermal basket catheter in an unexpanded condition according to one embodiment of the present disclosure.

FIG. 25 is an illustration of a perspective view of a portion of the thermal basket catheter in an unexpanded condition according to one embodiment of the present disclosure.

Figure 26:
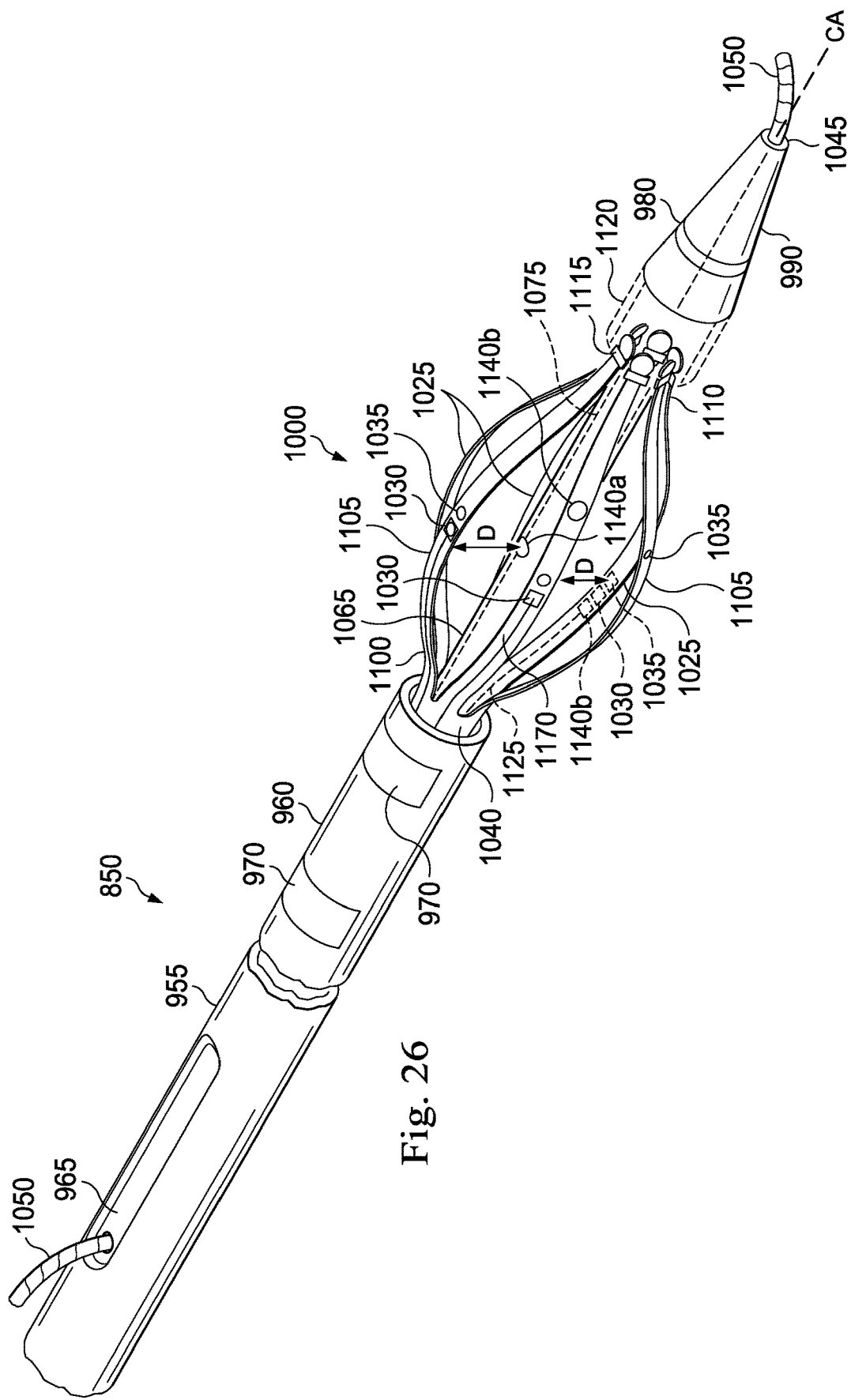

FIG. 26 is an illustration of a perspective view of a portion of the thermal basket catheter in an expanded condition according to one embodiment of the present disclosure.

FIG. 27 is an illustration of a perspective view of the expandable structure in an expanded condition according to one embodiment of the present disclosure.

FIG. 28 is an illustration of a plan view of the expandable structure in an expanded condition according to one embodiment of the present disclosure.

Figure 29A:
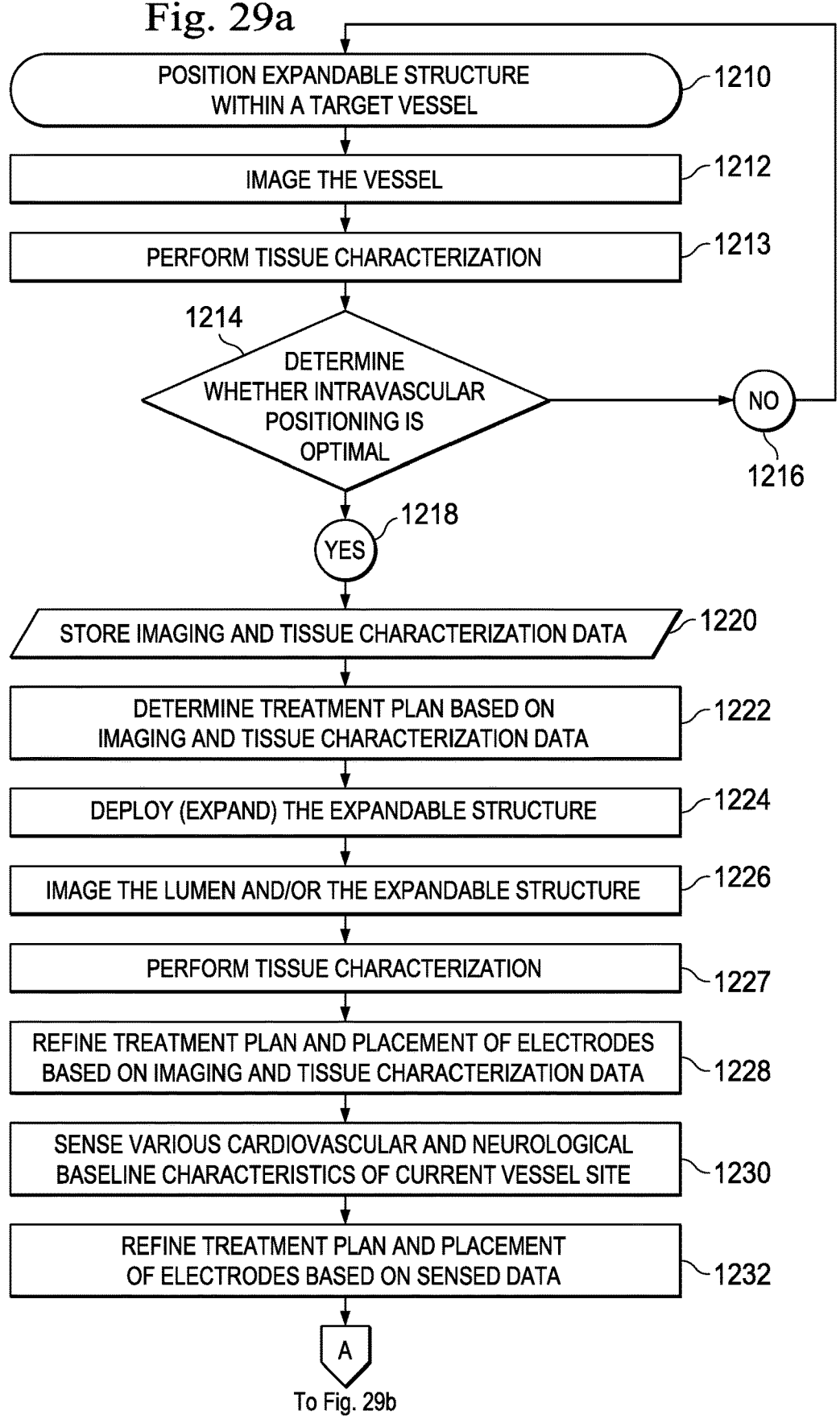
Figure 29B:
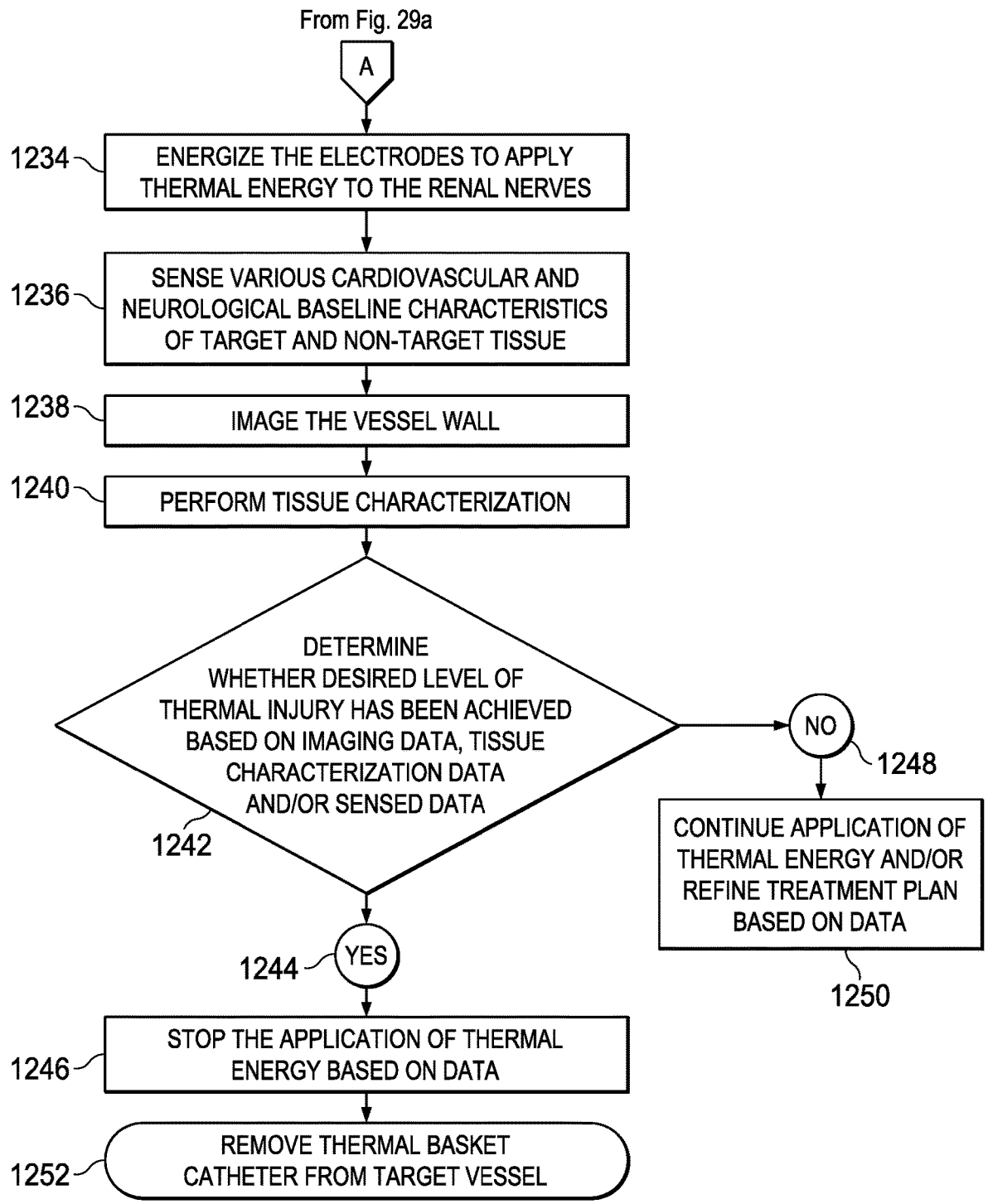

FIGS. 29a and 29b provide a schematic flowchart illustrating methods of delivering, controlling, and monitoring the thermal neuromodulation to renal vessels.

Figure 30:
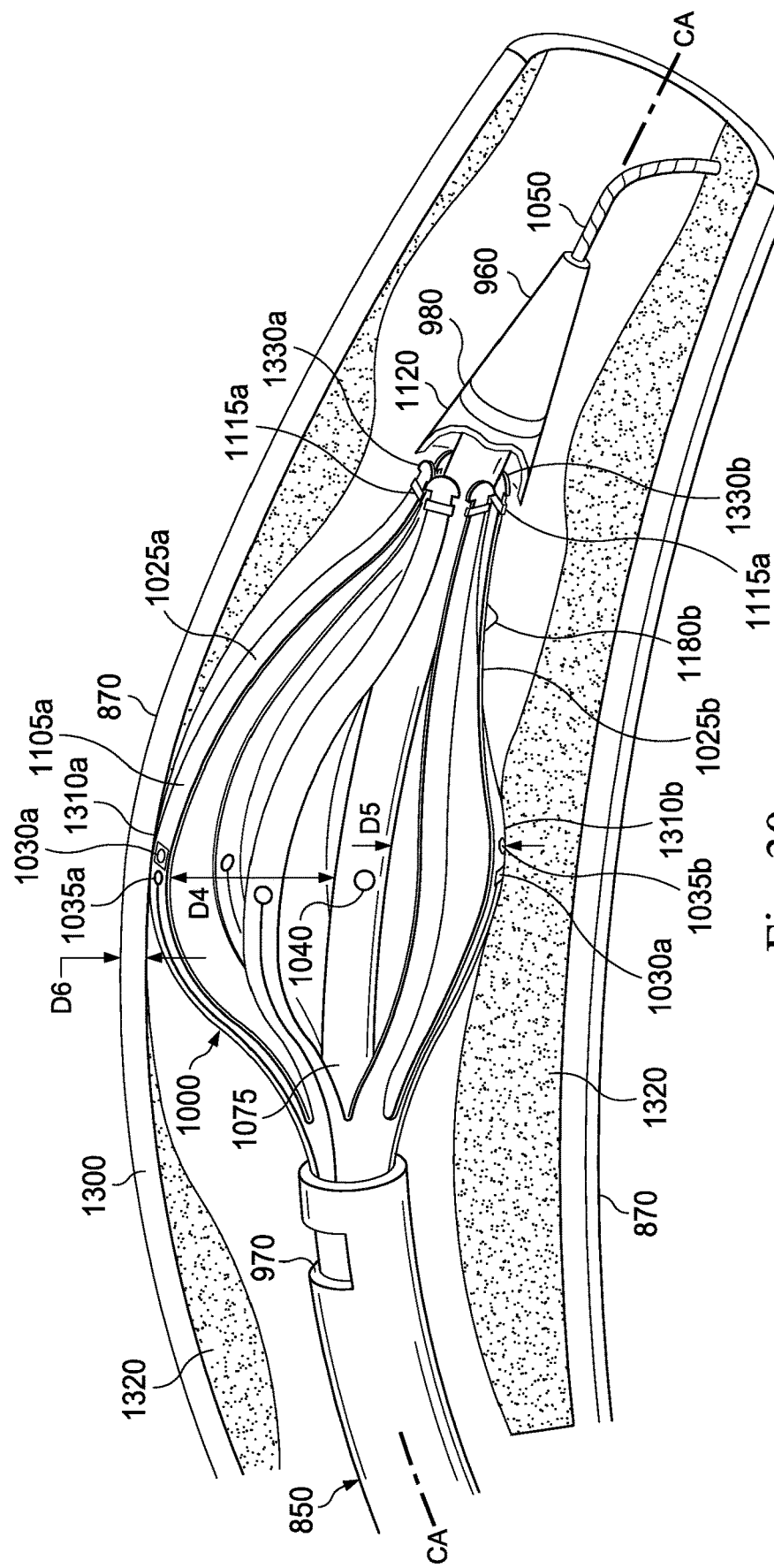

FIG. 30 is an illustration of a partially cross-sectional perspective view of a portion of the thermal basket catheter positioned within a vessel according to one embodiment of the present disclosure.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For simplicity, in some instances the same reference numbers are used throughout the drawings to refer to the same or like parts.

The present disclosure relates generally to an apparatus, systems, and methods for tissue ablation and image-guided monitoring of tissue ablation through tissue characterization. More particularly, the present disclosure relates to an ablating tool including an imaging device and in communication with a processor capable of tissue characterization for use in guiding, monitoring, and assessing the ablation procedure in real-time. The present disclosure describes systems and methods for tissue characterization by analyzing images created by an energy emission device, such as, by way of non-limiting example, an ultrasound transducer, deployable with an imaging system to facilitate interpretation of images of a patient's tissues of interest, such as ablated and neighboring tissue. The systems and methods described herein correlate image properties of the tissues of interest with pre-determined tissue properties to automatically and reproducibly characterize the tissues of interest in real time (i.e., as the tissues are being imaged and/or ablated). In some embodiments, the systems and methods described herein utilize various parameters related to the type of tissue being imaged, the type of ablation technique being employed, particular anatomical characteristics of the patient, and/or medical conditions of the patient to better characterize the tissues of interest. By automatically and reproducibly characterizing the imaged tissues in real time, the systems and methods described herein minimize the known observer-variability associated with tissue characterization by observers. Moreover, by specifically characterizing the specific tissue types and the degree of ablation in real-time, the systems and methods described herein allow the healthcare provider to appropriately adjust the degree, location, and type of ablation during the ablation procedure.

FIG. 1 illustrates an ablation system 100 that is configured to deliver ablative energy to target tissues and monitor the ablated tissues according to one embodiment of the present disclosure. The system 100 includes an ablation catheter 110 comprising an elongate, flexible, tubular body 120 that is configured for intravascular placement and defines an internal lumen 125. The body 120 extends from a handle 130 along a longitudinal axis CA, which is coupled to an interface 140 by an electrical connection 145. The body 120 includes a proximal portion 150 and a distal portion 160. In FIG. 1, the distal portion 160 includes an ablative element 170 and an imaging apparatus 180 positioned proximal to a distal tip 190. The ablative element 170 and imaging apparatus 180 are positioned on a proximal segment of the distal tip 190. In the pictured embodiment, the ablative element 170 is positioned proximal to the imaging apparatus 180. In other embodiments, the ablative element 170 is positioned distal to the imaging apparatus 180. Generally, the catheter 110 may be configured to take on any desired profile, which may depend upon the type of ablative element, the type of imaging apparatus (e.g., ultrasound, OCT, multi-modality, etc.), the desired application, or the particular tissue of interest. In some embodiments, aspects of the catheter 110 may be substantially similar to aspects of a catheter disclosed in U.S. Patent Application No. 2011/0251487, titled "Apparatus and Method s for Intravascular Ultrasound Imaging and for Crossing Severe Vascular Occlusions," and published Oct. 13, 2011, which is incorporated by reference herein in its entirety.

The interface 140 is configured to connect the catheter 110 to a patient interface module or controller 210, which may include a graphic user interface (GUI) 215. More specifically, in some instances the interface 140 is configured to communicatively connect at least the imaging apparatus 180 and the ablative element 170 of the catheter 110 to a controller 210 suitable for carrying out ablation and intravascular imaging. The controller 210 is in communication with and performs specific user-directed control functions targeted to a specific device or component of the system 100, such as the ablation catheter 110, the imaging apparatus 180, and/or the ablative element 170.

The interface 140 may also be configured to include a plurality of electrical connections, each electrically coupled to the ablative element 170 via a dedicated conductor and/or a cable (not shown), respectively, running through the lumen 125 of the body 120. Such a configuration allows for a specific group or subset of electrodes on the ablative element 170 to be easily energized with either monopolar or bipolar energy, for example. Such a configuration may also allow the ablative element 170 to transmit data from any of a variety of sensors on the ablative element via the controller 210 to data display modules such as a GUI 215 and/or a processor 220. The interface 140 is coupled to an ablation source 225 via the controller 210, with the controller 210 allowing energy to be selectively directed to the portion of the target tissue that is engaged by the ablative element 170.

The ablation catheter 110 includes one ablative element 170 positioned on the distal portion 160 of the body 120, as described above. However, other embodiments may include any number of ablative elements positioned in any of a variety of arrangements along the body 120. The ablative element may employ any ablative method known in the art, including, without limitation, radiofrequency (RF) energy, cryoablation, lasers, chemicals, high-intensity focused ultrasound (HIFU). Thus, the ablative element 170 may comprise, without limitation, RF ablation electrodes, microwave ablation antenna, laser ablators, HIFU ablators, and cryogenic ablators. The ablation element 170, which may be constructed of one or more electrode materials known in the art, has an ablating field (or ablating volume) 221 and is configured to ablate the tissue located within the ablating field 221. In some embodiments, the ablating field 221 comprises a fixed size and shape. In other embodiments, the size and/or shape of the ablating field 221 is alterable upon instructions from the user and/or the processor 220. In some embodiments, for example, where the ablative element comprises a high intensity focused ultrasound (HIFU) ablator, the ablating field may be cone-shaped. In other embodiments, where the ablative element comprises a radiofrequency (RF) ablator, the ablating field may be hemispherical. In some embodiments, the ablative element is configured to employ more than one type of ablative energy. In some embodiments, the ablation catheter 110 employs multiple ablative elements capable of using different ablative energies. In some embodiments, the ablation catheter 110 may have multiple ablative elements that operate separately or in concert to form the desired lesions during an ablation procedure.

In the pictured embodiment, the imaging apparatus 180 comprises an ultrasound imaging transducer. The imaging apparatus 180 can take the form of any one of a number of known ultrasound imaging transducers, such as, for example and without limitation, a phased array, a forward-looking array, a mechanically steered sector array, a rotational transducer, a vector array, a forward-looking oscillator transducer or a linear array. For example, in some embodiments involving cardia ablation applications, the imaging apparatus comprises intracardiac echocardiography (ICE) or forward-looking ICE. The imaging apparatus has an imaging field of view 223 that may or may not overlap with the ablating field 221. In the pictured embodiment, the imaging field of view 223 is shown overlapping with the ablating field 221, thereby allowing the user to image the tissue being ablated within the ablating field 221 in real-time.

It should be appreciated that while the exemplary embodiments herein are described in terms of an ultrasonic imaging apparatus, or more particularly the use of IVUS data (or a transformation thereof) to render images of an object, the present disclosure is not so limited. Thus, for example, an imaging apparatus using backscattered data (or a transformation thereof) based on electromagnetic radiation (e.g., light waves in non-visible ranges such as Optical Coherence Tomography, X-Ray CT, infrared spectroscopy, etc.) to render images of any tissue type or composition (not limited to vasculature, but including other human as well as non-human structures) is within the spirit and scope of the present disclosure. Any form of imaging, measuring, and/or evaluation device (and resultant data) is within the spirit and scope of the present disclosure. Still further, while the system and techniques are described in the context of an invasive ultrasound system, it will be appreciated that the system and method of conducting ablation therapy in combination with tissue characterization may be accomplished throughout the body whether tissues are accessed through natural openings or through openings formed through the skin. In addition, the same techniques may be applied to external tissue of the body.

The controller 210 is connected to the processor 220, which is typically an integrated circuit with power, input, and output pins capable of performing logic functions, an imaging energy generator 222, and the ablation source 225. The processor 220 may include any one or more of a microprocessor, a controller, a digital signal processor (DSP), an application specific integrated circuit (ASIC), a field-programmable gate array (FPGA), or equivalent discrete or integrated logic circuitry. In some examples, processor 220 may include multiple components, such as any combination of one or more microprocessors, one or more controllers, one or more DSPs, one or more ASICs, or one or more FPGAs, as well as other discrete or integrated logic circuitry. The functions attributed to processor 220 herein may be embodied as software, firmware, hardware or any combination thereof.

The processor 220 may include one or more programmable processor units running programmable code instructions for implementing the ablative methods described herein, among other functions. The processor 220 may be integrated within a computer and/or other types of processor-based devices suitable for a variety of intravascular applications, including, by way of non-limiting example, ablation, intravascular imaging, and tissue characterization. The processor 220 can receive input data from the controller 210, a memory 245, a characterization database 250, accessory devices 240, the imaging apparatus 180, and/or the ablative element 170 directly or via wireless mechanisms. The processor 220 can interpret and use such input data to generate control signals to control or direct the operation of the catheter 110. In some embodiments, the user can program or direct the operation of the catheter 110 and/or the accessory devices 240 from the controller 210 and/or the GUI 215. In some embodiments, the processor 220 is in wireless communication with the imaging apparatus 180 and/or the ablative element 170, and can receive data from and send commands directly to the imaging apparatus 180 and/or the ablative element 170.

In various embodiments, the processor 220 is a targeted device controller that may be connected to a power source 230, accessory devices 240, the memory 245, and/or the ablation source 225. In such a case, the processor 220 is in communication with and performs specific control functions targeted to a specific device or component of the system 100, such as the imaging apparatus 180 and/or the ablative element 170, without utilizing user input from the controller 210. For example, the processor 220 may direct or program the imaging apparatus 180 and/or the ablative element 170 to function for a period of time without specific user input to the controller 210. In some embodiments, the processor 220 is programmable so that it can function to simultaneously control and communicate with more than one component of the system 100, including the accessory devices 240, the power source 230, and/or the ablation source 225. In other embodiments, the system includes more than one processor and each processor is a special purpose controller configured to control individual components of the system.

In the pictured embodiment, the controller 210 is configured to couple the imaging apparatus 180 to the imaging energy generator 222. In embodiments where the imaging apparatus 180 is an intravascular ultrasound (IVUS) transducer(s), the imaging energy generator comprises an ultrasound energy generator. Under the user-directed operation of the controller 210, the imaging energy generator 222 may generate a selected form and magnitude of energy (e.g., a particular energy frequency) best suited to a particular application. At least one supply wire (not shown) passing through the body 120 and the interface 140 connects the imaging apparatus 180 to the imaging energy generator 222.

The user may use the controller 130 to initiate, terminate, and adjust various operational characteristics of the imaging energy generator 222.

The ablation source 225 may be configured to produce thermal energy that may be directed to the ablative element 170. As illustrated in FIG. 1, the ablative element 170 is connected to the ablation source 225. In some embodiments, wires or conductors extending through the lumen 125 of the body 120 connect to the conductor 145 and/or the interface 140, which ultimately couples the ablative element 170 to the ablation source 225. Under the control of the user or an automated control algorithm in the processor 220, the ablation source 225 generates a selected form and magnitude of thermal energy, including, without limitation HIFU energy or RF energy. The ablation source 225 may be utilized with any of the catheters described herein for delivery of a thermal electric field with the desired field parameters, i.e., parameters sufficient to thermally induce ablation and/or neuromodulation via heating, cooling, and/or other mechanisms such as electroporation. It should be understood that the catheters described herein may be electrically connected to the ablation source 225 even though the ablation source 225 is not explicitly shown or described with respect to each embodiment. The user may direct whether the ablative element 170 is energized with monopolar or bipolar RF energy by using the controller 210 or programming the processor 220.

In the pictured embodiment, the ablation source 225 is located external to the patient. In other embodiments, the ablation source 225 may be positioned internal to the patient. In alternative embodiments, the ablation source may additionally comprise or may be substituted with an alternative thermal energy generator, such as, by way of non-limiting example, a thermoelectric generator for heating and/or cooling (e.g., a Peltier device) or a thermal fluid injection system for heating and/or cooling. For embodiments that provide for the delivery of a monopolar electric field via an electrode on the ablative element 170, a neutral or dispersive ground pad or electrode (not shown) can be electrically connected to the ablation source 225.

The power source 230 may be a rechargeable battery, such as a lithium ion or lithium polymer battery, although other types of batteries may be employed. In other embodiments, any other type of power cell is appropriate for power source 230. The power source 230 provides power to the system 100, and more particularly to the processor 220. The power source 230 may be an external supply of energy received through an electrical outlet. In some examples, sufficient power is provided through on-board batteries and/or wireless powering.

The various peripheral devices 240 may enable or improve input/output functionality of the processor 220. Such peripheral devices 240 include, but are not necessarily limited to, standard input devices (such as a mouse, joystick, keyboard, etc.), standard output devices (such as a printer, speakers, a projector, graphical display screens, etc.), a CD-ROM drive, a flash drive, a network connection, and electrical connections between the processor 220 and other components of the system 100. By way of non-limiting example, a processor may manipulate signals from the imaging apparatus 180 to generate an image on a display device, may coordinate aspiration, irrigation, and/or thermal neuromodulation, and may register the treatment with the image. Such peripheral devices 240 may also be used for downloading software containing processor instructions to enable general operation of the catheter 110, and for downloading software implemented programs to perform operations to control, for example, the operation of any auxiliary devices attached to the catheter 110. In some embodiments, the processor may include a plurality of processing units employed in a wide range of centralized or remotely distributed data processing schemes.

The memory or database 245 is typically a semiconductor memory such as, for example, read-only memory, a random access memory, a FRAM, or a NAND flash memory. The memory 245 interfaces with processor 220 such that the processor 220 can write to and read from the memory 345. For example, the processor 220 can be configured to read data from the imaging apparatus 180 and write that data to the memory 345. In this manner, a series of data readings can be stored in the memory 245. The processor 220 is also capable of performing other basic memory functions, such as erasing or overwriting the memory 245, detecting when the memory 345 is full, and other common functions associated with managing semiconductor memory. In the pictured embodiment, the memory 245 comprises a database of characterization data.

The characterization application 250 is adapted to receive data (e.g., imaging data) from the processor 220 and/or the controller 210. The characterization application may exist as a single application or as multiple applications, and be locally or remotely stored. In an exemplary embodiment, the characterization application 250 is adapted to receive and store characterization data (e.g., tissue type, ablation characteristics, and secondary parameters). In particular, to create a database of characterization data, after a tissue specimen has been imaged and IVUS data has been collected, a histology correlation is prepared by collecting, dissecting, and preparing the tissue specimen for slide review (e.g., fixing and staining the tissue specimen with a process that is well known in the art). Slide review allows a clinician to identify and characterize the tissue type(s) and/or histological chemicals/markers (i.e., chemicals and/or markers associated with particular tissue types) found within the specimen. It should be noted that the particular method used to characterize the tissue specimen is not a limitation of the present disclosure, and all tissue specimen characterization methods generally known to those skilled in the art are within the scope of the present disclosure.

In one embodiment, the tissue specimen comprises a region of ablated tissue. The tissue may be any of a variety of tissue types, including, by way of non-limiting example, muscle tissue, fatty tissue, fibrous tissue, fibrolipidic tissue, vessel tissue (e.g., by way of non-limiting example, compositional tissues such as vessel wall, luminal wall, medial-advential boundary), neural tissue, calcific tissue, necrotic tissue, calcified-necrotic tissue, collagen compositions, cholesterol deposits, and/or adventitial tissue. In addition, the tissue specimen can comprise ablated tissue in any of a variety of stages of ablation, including, by way of non-limiting example, minimally ablated tissue, moderately ablated tissue, majorly ablated tissue, and/or completely ablated tissue. The characterization data gathered from the tissue specimens can include all other identifiable characteristics generally known to those of skill in the art. In some embodiments, tissue specimens having a full range of varying degrees of ablation per tissue type are interrogated (imaged and histologically sectioned) for inclusion in the characterization application 250.

The identified tissue type(s) and/or characterization conclusions are provided to the characterization application 250 as characterization data. In some embodiments, the characterization data is provided via the GUI 215 or another input device that is electrically coupled to the controller 210 and/or the processor 220. The characterization data is then stored in the memory or database 245.

In one embodiment, the characterization application 250 is adapted to create a histology image of the tissue specimen and to identify the at least one corresponding region on an image (e.g., an IVUS image) of the tissue specimen. A region of interest (ROI) on the histology image (which may be provided to the characterization application 250 via the GUI 215 or another input device in the form of digitized data that is used to create the histology image) can then be identified by the user. The ROI may be characterized by the characterization data, and can comprise the whole tissue specimen or only a portion thereof. The characterization application is adapted to identify a corresponding region on the scanned image (e.g., IVUS image).

In some instances, the histology image may need to be morphed or warped to accurately match and substantially fit the contour of the IVUS image (thereby removing histological preparation artifacts). In some embodiments, therefore, the characterization application 250 is adapted to morph or warp the histology image to accurately match the IVUS image. Specifically, the characterization application 250 is configured to identify at least one landmark common to both the histology image and the IVUS image and is adapted to use various algorithms to substantially align the two images. The landmark may comprise an anatomic landmark (such as, by way of non-limiting example, side-branching vessels, a vessel wall, and a tumor border) or a marker (such as, by way of non-limiting example, a suture tie or an inked mark). In one embodiment, the characterization application is adapted to use a first algorithm (e.g., a morphometric algorithm) to substantially align the corresponding landmarks and a second algorithm (e.g., a thin plate spline (TPS) deformation technique) to substantially align the non-landmark portions of the object.

In one embodiment, the characterization application 250 is further adapted to determine and store at least one parameter associated with the ROI portion of the IVUS image. In particular, the characterization application 250 is adapted to identify the IVUS data (i.e., the raw backscatter data) that corresponds to the ROI identified on the IVUS image (i.e., the IVUS data that was originally used to create the ROI on the IVUS image). Different types and densities of tissue absorb and reflect emitted energy differently. Each reflected signal is characteristic of the type of tissue and the condition of the tissue that reflected it. Differences in the reflected signal along each path can be determined by performing analysis on the signals. As a result, identifying different signal characteristics along each reflected path allows for a correlation to the type of tissue and the condition of the tissue associated with those particular signal characteristics. As will be described below, the signal characteristics of each reflected signal can serve as a signature for different types of components within the scanned tissue, including, for example and without limitation, necrotic plaque components within an artery, minimally ablated muscle tissue, or completely ablated neural tissue.

The at least one parameter is then stored in the memory 245, where it is linked to the characterization data associated with the ROI. Each parameter may be associated with more than one tissue type or degree of ablation. For example, a first parameter may be common to multiple tissue types and multiple degrees of ablation. In some embodiments, signal analysis (i.e., frequency analysis, etc.) is performed on the identified IVUS data before the parameters are identified because the frequency information can serve as a "signature" for a particular tissue type or characteristic. The IVUS data may be converted or transformed into the frequency domain to identify the specific frequency spectrum of the ROI. The characterization application 250 and this transformation process are described in further detail below with reference to FIG. 3.

It should be appreciated that the number and location of the components depicted in FIG. 1 are not intended to limit the present invention, and are merely provided to illustrate an exemplary environment in which the catheters, systems, and methods described herein may operate. Thus, for example, a system having a plurality of databases and/or a remotely located characterization application is within the spirit and scope of this disclosure.

An exemplary method of populating the database or memory 245 is illustrated in FIG. 2. Specifically, at step 300, IVUS data (i.e., RF backscatter data) is collected from a portion of the specimen. This data is used to create an IVUS image, which may be a two dimensional image or a three dimensional image, at step 305. At step 310, the scanned portion of the specimen is dissected and/or cross-sectioned and a tissue type (and/or characterizations thereof) is identified. At step 315, this characterization data is transmitted to the tissue characterization system 100. In particular, the characterization data may be transmitted to the memory 245 and/or the characterization application 250. The characterization data may include a variety of identifying and/or characterization information, such as, for example and without limitation, information about the type of tissue, the different cell components within the tissue, and the degree of ablation (e.g., varying cellular changes due to ablation). As a further feature, IVUS data may be collected for an unablated ROI and compared to an existing database to obtain an initial characterization. Ablation energy can then be applied to the ROI to change the nature of the tissue in the ROI. Then, the ROI tissue may be dissected and/or cross-sectioned. At step 320, an image of the cross-sectioned object is created and an ROI is identified (e.g., by a user and/or the processor 220). The image may be two-dimensional or three dimensional. At step 325, this image may be morphed, if needed, to substantially match the cross-section image to the IVUS image formed at step 305. This may include identifying and matching up at least one common landmark on the two images using an algorithm, as described above. At step 330, the ROI is mapped to the IVUS image and associated IVUS data is identified. Image analysis (including, for example and without limitation, spectral analysis and frequency analysis) is then performed on the associated IVUS data at step 335, and at least one parameter is identified at step 340. At step 345, the at least one parameter and the characterization data is stored in the memory 245 and/or the characterization application 250. In some embodiments, the at least one parameter is stored such that it is linked to the characterization data.

The process depicted in FIG. 2 is repeated for each tissue component or section desired to be identified and/or characterized, and may be repeated for each component as many times as desired in order to obtain an accurate range of signal properties. With the database or memory 245 populated with an accurate range of signal properties corresponding to several tissue types at various degrees of ablation, a tissue type and ablation level can be identified when the acquired parameters substantially match parameters stored in the memory 245, as described in further detail below with respect to FIG. 3.

FIG. 3 illustrates one embodiment of an ablation system 400 configured to ablate, scan, and analyze one or more characteristics of an object 405, which may be located on the external surface or inside a patient's body, to characterize the tissue components and/or degree of ablation associated with the object 405. In the pictured embodiment, the system 400 includes an ablation system console 410 that includes data processing, analysis, and/or display capabilities. The ablation system console 410 may comprise components found within the ablation system 100, including, for example and without limitation, the GUI 215, the imaging energy generator 222, the ablation source 225, the controller 210, and the processor 220. The ablation system console 410 may be a general purpose computer configured to communicate with and collect data from the catheter 110. In another embodiment, the console 410 may be a small portable ablator and scanner. The ablation system console 410 is in communication with the characterization apparatus 250, the memory 245, and the power source 230. In some embodiments, the ablation system console 400 is in communication with the accessory devices 240.

To perform a guided ablation procedure of the object 405, the catheter 110 may maneuvered such that the ablative element 170 and the imaging apparatus 180 are positioned near the object 405. In some instances, the object 405 may be located within a vessel in a patient's body. FIGS. 4 and 5 illustrate the layers of a normal artery 420. The innermost layer that defines the lumen 425 of the artery 420 comprises the intima 430. In a healthy artery, the intima is relatively thin. As plaque develops and infiltrates the intima, it increases in thickness. Medial layers 435 surround the intima 430. The medial layers 435 include smooth muscle tissue and provide structural integrity for the artery 420. The medial layers are made up of three layers that include two elastic layers, an inner elastic lamina 436 and an outer elastic membrane 437, along with a thicker muscular media 438. The outermost layer is the adventitia 440, which typically comprises fibrous tissue such as collagen.

FIG. 6 illustrates the distal portion 160 of the catheter 110 positioned within a vascular lumen 445 of an occluded artery 450, in which the lumen 445 has been blocked by atherosclerosis. When the lumen of an artery has been severely of completely occluded, as shown in FIG. 6, a healthcare provider may not be able to advance a therapeutic device through the stenosis without first creating a passage through the occlusion. In order to reduce the risk of perforating the blood vessel and/or inadvertently injuring non-target layers of the blood vessel by ablation, it is important for the user to be able to characterize the tissue layers and tissue components within the lumen to distinguish the regions that are more susceptible to injury and to evaluate the degree of ablation through the ablation procedure. The devices, systems, and methods of the present disclosure provide a user with the tools to ablate the occlusive tissue and tunnel a passageway through the occlusion and enhance blood flow through the artery. Moreover, the devices, systems, and methods of the present disclosure provide a user with the tools to create such a passageway while guarding against inadvertently over-ablating tissue and/or ablating non-target areas or tissue types.

In FIG. 6, the object 405 is the occlusion or stenosis located within the lumen 445. In some instances, the object 405 comprises a chronic total occlusion of the vessel 450 as shown in FIG. 6. The user can advance the catheter 110 through the lumen 445 until the ablative element 170 and the imaging apparatus 180 are situated adjacent the object 405. The user can then activate the imaging apparatus 180 to image at least a portion of the object 405. In some embodiments, the imaging apparatus 180 is oriented at an angle to the longitudinal axis of the catheter 110 so that as the imaging apparatus is rotated, it will emit ultrasound energy in a conical, side-looking pattern or field of view 223 (shown in FIG. 1). In other embodiments, the imaging apparatus may emit ultrasound energy in a forward-looking pattern or field of view 223. The imaging apparatus 180 then collects waves of ultrasound energy reflected back from the object 405 and surrounding tissues as data.

With reference back to FIG. 3, the data collected by the imaging apparatus 180 of the catheter 110 is initially in the form of raw data 460 of the reflected signals along each scan line. The data 460 is then refined or transformed into a format that can be analyzed by the characterization application 250 to determine various signal characteristics that may identify associated tissue types within and adjacent the scanned object 405. In the pictured embodiment, the characterization application 250 includes several component parts, including the memory or database 245, a signal analyzer logic 465, and a correlation logic 475. The signal analyzer logic 465 is configured to process and analyze the data 460 to identify, in real-time, the various components of the scanned object 405. The signal analyzer logic 465 is configured to identify various types of tissue and/or tissue components and to provide an assessment as to the degree of ablation based on the type of tissues and/or tissue components identified, an amount of ablated tissue identified, or both.

The signal analyzer logic 465 includes logic to transform the data 460 into an analyzable domain and analyze the transformed information from the signals to determine one or more signal properties 470. For example, each scan line can be analyzed in segments and signal properties can be determined for each segment. The segments may be equal in size, different in size, equally spaced from each other, overlapping each other, and/or defined in other desired ways.

The signal properties 470 are processed by the correlation logic 475, which is configured to correlate the signal properties of the scan line segment with the type of tissue component having those or similar signal properties. In that regard, the correlation logic 475 is configured to compare and match the signal properties 470 to pre-determined or pre-generated tissue signal properties 480 contained within the memory or database 245. Various parameters may comprise the database of pre-determined tissue signal properties 480. The parameters comprising the database 245 would be pertinent to both the desired application or tissue-of-interest and the imaging modality of the imaging probe (i.e., ultrasound, OCT, spectroscopy, etc.). The correlation logic 475 is configured to recognize the type of imaging modality employed by the imaging probe 115 and to use the appropriate pre-determined tissue signal properties 480 associated with that particular imaging modality. For example, if the imaging modality being used were ultrasound, the pre-determined signal properties 480 may include various parameters in the spectral domain directly associated with scatter size, density, viscosity, and their acoustic properties such as impedance and attenuation coefficient. The database also contain macro-data about overall ablation characteristics, such as size, cell directionality, morphology, as well as the likelihood of bubble formation during ablation.

In some embodiments, the imaging system 100 may employ a multitude of different imaging modalities to image the same object 405. In some embodiments, these imaging modalities are used sequentially, whereas in other embodiments, the different imaging modalities are used simultaneously (e.g., using a multi-modality imaging apparatus). In one embodiment, the imaging probe 115 may be configured to image the object 405 using a multitude of different imaging modalities (e.g., OCT and ultrasound). In some embodiments, the correlation logic 475 is configured to combine or analyze the pre-determined signal properties 480 associated with each imaging modality used to perform a tissue characterization 485.

Secondary parameters 490 may be included within the data structure to reflect the type of tissue and/or the particular pre-existing conditions or differential diagnoses of the patient. The secondary parameters 490 may be utilized by the correlation logic to more accurately compare and match the signal properties 470 to the pre-determined signal properties 480. One secondary parameter 490 may comprise the type of tissue observed within the object 405. In some embodiments, the imaging system 400 can determine the type of tissue or anatomic region observed with the object 405 and use this as a secondary parameter before automatically selecting the appropriate pre-determined signal properties associated with the type of tissue or anatomic region or appropriately adjusting the pre-determined signal properties 480 to reflect the type of tissue or anatomic region. In other embodiments, the user may enter the type of tissue or anatomic region manually (e.g., via the GUI 215 attached to the ablation system console 410), and either the user or the imaging system 400 may select the appropriate pre-determined signal properties 480 associated with that type of tissue/region or appropriately adjust the pre-determined signal properties to reflect this type of tissue/region. For example, if the tissue being scanned is a calcified vascular plaque, either the user or the imaging system 400 may select the appropriate pre-determined signal properties 480 associated with calcified plaque tissue or appropriately adjust the pre-determined signal properties to reflect ablative changes observed for calcified plaque tissue. In some embodiments, a three-dimensional data set can be constructed with the imaging apparatus 180 to provide further parameters related to tissue type and matched back to the secondary parameters 490 in the database 245 that contains these pre-determined ablation values for various tissue types.

Another secondary parameter 490 associated with the imaging may comprise the particular frequency or harmonics employed by the imaging apparatus 180. For example, the database 245 may contain particular sets of pre-determined signal properties 480 associated with particulars frequencies or harmonic patterns.

Other secondary parameters 490 included within the database 245 of pre-determined signal properties 480 may relate to the particular pre-existing conditions or differential diagnoses of the patient. For example, in the context of imaging atherosclerosis, it might be important to relate whether a patient is diabetic and/or hypertensive to better analyze the signal properties and to give an appropriate disease risk level. The secondary parameters 490 may be entered into the database 245 by the user or be selected from a pre-established menu or list of options already present within the database.

In one embodiment, the pre-determined signal properties 480 and secondary parameters 490 discussed above are configured in the database 245 that associates measured or observed signal properties 470 to pre-determined tissue signal properties 480 that reflect specific types of tissue component such as, by way of non-limiting example, fluid, blood, normal tissue, necrotic tissue, fatty tissue, or calcific tissue, with varying degrees of ablation. The database 245 may be implemented in a variety of ways including a data file, an array, a table, a linked list, a tree structure, a database, combinations of these and multiple components of each if desired. The correlation logic 475 matches the signal properties 470 from a path or scan line, or a region of the path or scan line, to the pre-determined properties 480 and outputs a tissue characterization 165 that identifies the type of tissue and the level of ablation. In some embodiments, the correlation logic 475 weights the pre-determined properties with other parameters (such as the secondary parameter of tissue type and/or anatomic region) before matching the signal properties 470 from a path or scan line, or a region of the path or scan line, to the weighted pre-determined properties 480 and outputting the tissue characterization 485. The system 100 then repeats the analysis for other segments on the current path or scan line and then for the other paths or scan lines. In some embodiments, the system 400 may repeat the analysis for the imaging data received by each of the other imaging modalities. In some such embodiments, the system 400 utilizes the correlation logic 475 to combine the correlation conclusions from different imaging modalities to arrive at a final tissue characterization 485.

Returning to the example shown in FIG. 6, in which the object 405 is the occlusion located within the lumen 445 of the vessel 450, the imaging apparatus 180 collects waves of ultrasound energy reflected back from the object 405 and surrounding tissues as raw data 460. In the pictured embodiment, the imaging apparatus is located proximal to the ablation element 170. As described above, in other embodiments, the imaging apparatus may be located distal to the ablation element, and may enable forward-looking imaging. In some embodiments, the catheter 110 employs two imaging apparatuses positioned on either side of the ablative element. In embodiments using ultrasound imaging, the transducers of the imaging apparatus 180 would be pulsed along scan lines and then acquire echoes of backscatter signals reflected from the tissue along each scan line. The backscatter signal is characteristic of the type of tissue (including the tissue composition and level of ablation) that reflected it. Differences in the backscatter signal along each scan line can be determined by performing a frequency analysis, using spectral analysis and autoregressive coefficients, a wavelet decomposition, and/or a curvelet decomposition on the signals. As a result, identifying different signal characteristics along each scan line allows for a correlation to the type of tissue and a certain level of ablation associated with those particular signal characteristics. As described above, signal characteristics of the backscattered signal can serve as a signature for different types of components and ablative effects within an object, including, for example, plaque components within an artery or the level of ablation within the plaque.

With reference again to FIG. 3, the data collected by the imaging apparatus 180 is initially in the form of raw ultrasound data 460 of the backscattered signals along each scan line. The ultrasound data 460 is then analyzed to determine various signal characteristics that may identify associated tissue types. The signal analyzer logic 465 is configured to process and analyze the data 460 to identify, in real-time, the components and level of ablation of the scanned occlusion. Because different types and densities of tissue absorb and reflect the ultrasound pulses differently, the signal analyzer logic 465 utilizes the reflected backscatter data to assemble a two-dimensional or three-dimensional ultrasound characterization of the object 405 from hundreds of pulse/acquisition cycles. In this embodiment, the logic is configured to identify various types of plaque components, vessel wall structures such as intima, medial layers and adventitia, and ablation levels within the object 405, and to provide an assessment as to the next step in the patient's ablative procedure based on the type of plaque identified, an amount of plaque component identified, and/or the level of ablation including potential damage to the vessel wall.

In the pictured embodiment, the signal analyzer logic 465 includes logic to transform the data 460 to the frequency domain and analyze frequency information of the signals to determine one or more signal properties 470. Illustrated in FIG. 7 is one example of data of one scan line 550 plotted as voltage over time. The scan line can be analyzed in segments represented by the windows illustrated in the figure, such as window 555. The data within the window 555 is transformed in this embodiment to a power spectrum density plot as shown in FIG. 8. Signal properties from the segment 555 are determined from the power spectrum of FIG. 8. Signal properties, in this case also referred to as spectral properties, may include the y-intercept, maximum power, mid-band fit, minimum power, frequencies at maximum and minimum powers, slope of regression line, integrated backscatter, or combinations of these or others.

Illustrated in FIG. 9 is one embodiment of a signal analyzer logic 650 for processing and analyzing radio frequency ultrasound data. It will be appreciated that the signal analyzer logic 650 may be embodied as part of an ultrasound imaging console, an ablation system console, or as part of a separate system that receives raw radio frequency data from an ultrasound apparatus. If the radio frequency data is in analog form, a digitizer 655 may be provided to digitize the data. A signal processing logic 660 is configured to process each scan line of the ultrasound data and transform it to a format that can be analyzed. To reduce processing time, a border detection logic 665 may be used to determine the location of the borders of the object being scanned. Because the analysis in FIG. 6 is most interested in the components of the vascular occlusion 600, scan line data outside of the vessel 450 can be filtered and removed. One example of a border detection system is described in U.S. Pat. No. 6,381, 350, entitled "Intravascular Ultrasonic Analysis Using Active Contour Method and System," which is incorporated herein by reference for all purposes.

After border detection, the scan line data is transformed. Of course, border detection can be performed after transformation. Transformation logic 670 is configured to transform the remaining scan line data into a format suitable for analysis. In general, the transformed format should match the same format used to build the pre-determined signal properties of the object component. In one embodiment, the transformation logic 670 transforms the data to a power spectrum plot of frequency versus power output as shown in FIG. 8. Various transformation algorithms include a Fourier transformation, Welch periodograms, and autoregressive modeling. Other types of transformations can include transforming the data to wavelets that provide an image with frequency and time information. For example, other signal processing techniques may include wavelet decomposition or curvelet decomposition to deliver parameters that are relevant for discrimination between tissue types while not being influenced by the system transfer function of the imaging system and probe. Another transformation includes using impedance, rather than frequency, which gives an image of acoustic impedance. In this format, different tissue components have different impedance properties that provide different signal reflections. In the following example, a power spectrum density plot is used from a Fourier transformation.

With further reference to FIG. 9, a spectral analysis logic 675 analyzes the power spectrum of the scan line data to determine its spectral properties 680. As mentioned previously, spectral properties or parameters may include maximum power, frequency at the maximum power, minimum power, the frequency at the minimum power, the slope, y-intercept, mid-band fit, and integrated backscatter. The spectral parameters 680 are then inputted to a classification logic 685 that attempts to classify the spectral parameters associated to a particular scan line segment with previously measured spectral parameters from a known tissue component. As mentioned above, the signal analyzing techniques need not be limited to spectral analysis and autoregressive coefficients, but could entail use of wavelet decomposition or curvelet decomposition to deliver parameters that may be used by the classification logic 685 to discriminate between tissue types.

In one embodiment, a classification data structure 690 contains a statistical classification of measured or observed spectral properties (and/or other properties) associated with particular types of tissue and/or ablated tissue components. The classification data structure 690, in one embodiment, is previously generated from laboratory studies that correlate ultrasound data analysis of ablated tissue samples with their corresponding histology sections, as described above in relation to FIG. 2

A variety of pattern recognition approaches may be used by the classification logic 685 and/or correlation logic 475. For example, the database 245 of relevant secondary parameters 490 and pre-determined tissue signal properties 480 could be the starting point of various pattern recognition approaches, covering, but not limited to, classification trees, random forests, neural networks, regression trees, principal components, and/or a combination of these to arrive at an accurate tissue characterization. For example, in one embodiment, the pre-determined tissue signal properties 480 and/or the secondary parameters 490 may be stored in the database 245 as a classification tree or a regression tree having branch node conditions based on the pre-determined tissue signal properties and one or more leaf nodes that identify a tissue component with a particular level of ablation. In another embodiment, the pre-determined tissue signal properties 480 may be embodied in the database as an artificial neural network having one or more nodes that identify a tissue component with a particular level of ablation. In some embodiments, the classification logic 685 and/or the correlation logic 475 may utilize a random forest classifier to analyze a number of classification trees (e.g., different classification trees based on different pre-determined signal properties or based on a multitude of different imaging modalities) to arrive at a tissue characterization.

Continuing the analysis for other segments of a backscatter signal and segments from other scan lines collected from a scan, the system can provide helpful identification of the types of components within the object 405. Additionally, based on the location of a segment along a scan line, the system can make a determination as to the location of the corresponding tissue within the object 405. Then by combining data from adjacent segments and adjacent scan lines having the same tissue component, the system can estimate the size and/or volume of the tissue component. This may be important because certain components may create a greater risk of inadvertent rupture and/or injury based on their tissue type, location, and/or size, and it would be helpful to identify these conditions prior to continuing ablation. Similarly, in the evaluation of other conditions, using ultrasound or other imaging modalities, certain components may indicate a greater need for higher levels of ablation than others.

With reference again to FIGS. 3 and 6, the signal properties 470 are processed by the correlation logic 475 configured to correlate the signal properties of the scan line segment with the type of vascular component and a level of ablation having those or similar signal properties. In that regard, the correlation logic 475 is configured to compare and match the signal properties 470 to pre-determined tissue signal properties 480. In some embodiments, the correlation logic may first identify the type of vascular component, and then identify the level of ablation. In other embodiments, the correlation logic may identify the type of vascular component and its level of ablation at once. In some embodiments, the type of vascular component may be a secondary parameter as described above. In one embodiment, the pre-determined signal tissue properties 480 are configured in a database or data structure that associates measured or observed signal properties to a type of vascular component such as intima, media, adventitia, and types of plaque components that may be present. Various plaque components include calcium, fibrous, fibrolipid, and calcified-necrosis.

The correlation logic 475 matches the signal properties 470 from a scan line, or a region of the scan line, to the pre-determined properties 480, factors in any relevant secondary parameters 490, and outputs a tissue characterization 485 that identifies the type of tissue and the level of ablation of that tissue. The system may then repeat the analysis for other segments on this scan line and for the other scan lines. Thus, the tissue characterization 485 can identify the more ablated, less ablated, and non-ablated areas in real-time during the ablation procedure.

Illustrated in FIG. 10 is one embodiment of a methodology 700 associated with analyzing ultrasound signals and identifying the type of tissue component that corresponds to the signals. The illustrated elements denote "processing blocks" and represent computer software instructions or groups of instructions that cause a computer or processor to perform an action(s) and/or to make decisions. Alternatively, the processing blocks may represent functions and/or actions performed by functionally equivalent circuits such as a digital signal processor circuit, an application specific integrated circuit (ASIC), or other logic device. The diagram does not depict syntax of any particular programming language. Rather, the diagram illustrates functional information one skilled in the art could use to fabricate circuits, generate computer software, or use a combination of hardware and software to perform the illustrated processing. It will be appreciated that electronic and software applications may involve dynamic and flexible processes such that the illustrated blocks can be performed in other sequences different than the one shown and/or blocks may be combined or separated into multiple components. They may also be implemented using various programming approaches such as machine language, procedural, object-oriented, artificial intelligence, or other techniques. This applies to all methodologies described herein.

In other embodiments, the steps of the methodology 700 may be employed to analyze imaging signals received from another imaging modality and to identify the type of tissue component that corresponds to the signals. In such embodiments, instead of receiving ultrasound data and analyzing ultrasound imaging properties such as spectral properties, the ablation system 100 may instead receive imaging data specific to the particular type of imaging modality and analyze imaging properties specifically associated with the type of imaging modality used, in light of the relevant secondary parameters.

With reference to FIG. 10, analysis may begin as ultrasound data is received in real time during a scan or after a scan is completed (block 705). If the ultrasound data is still in the raw radio frequency form, it is digitized (block 710). In one embodiment, the digitized data is analyzed along a scan line, in one or more segments. The embodiment of FIG. 10 illustrates the analysis of one segment of data. Although not shown in FIG. 10, the processing repeats for each segment of a scan line and repeats for other scan lines until complete or until processing is stopped. Optionally, the process may allow for changing the properties of how a scan line is segmented such as defining various sizes and intervals of segments.

For a scan line being analyzed, a border detection algorithm may be used to identify the borders of the target object (block 715) and the analysis can be focused on the scan line data corresponding to the target object. Since the scan is not intravascular in this example, a scan line that passes through the target object may pass through two or more walls of the object. For example, in one embodiment, the region of interest for the scan is a vascular object such as a carotid body. The border detection algorithm may identify the borders of the carotid body and/or an adjacent vessel. A number of scan lines may pass through two walls of the carotid body. Thus, the border detection would attempt to search and identify at least two borders along a scan line. Many different border detection methods are available including analyzing signal properties of the scan line, reconstructing an image from the ultrasound data and detecting borders from the image data, and other methods. Scan line data outside the borders of the target object may be ignored or removed from analysis if desired.

The scan line can be segmented and analyzed by segment. In one embodiment, the signal data from a segment is transformed to a power spectrum form (block 720) such as in FIGS. 7 and 8. Spectral properties may be determined from the power spectrum (block 725) which may include the y-intercept, maximum power, mid-band fit, minimum power, frequencies at maximum and minimum powers, slope of regression line, integrated backscatter, and/or other properties from the power spectrum. Other properties may be determined from wavelet decomposition or curvelet decomposition techniques. The spectral properties and/or other properties of the scan line data are then compared to corresponding pre-determined properties of known tissue components to determine which type of component best matches the scan line spectral properties.

In one embodiment, the pre-determined tissue properties are structured as a classification tree generated from statistical analysis of how the properties correlate to a type of tissue component. The scan line spectral properties are then processed through the tree (block 730), traversing branches based on how the spectral properties meet the conditions of the branch nodes. The tree is traversed to a leaf node that identifies a type of tissue component. The spectral properties of the scan line segment are then characterized as this type of component (block 735). The system 100 may also output an assessment score of the observed ablation level within the tissue component (block 740).

With reference to FIG. 11, once a sufficient amount of data is analyzed and the tissue type and ablation level of the object 405 are characterized, a diagnostic logic 750 may be included in the ablation system 400 to generate an ablation assessment 755 as to the level of progress made in the patient's treatment in light of the patient's preexisting health conditions, symptoms, and differential diagnosis. For example, in some embodiments, the diagnostic logic may quantify the appropriate level of ablation to be employed next or the diagnostic logic may indicate that the treatment is complete based on the types of tissues and levels of ablation observed. Additionally, the diagnostic logic 750 may be configured to reconstruct the received data into displayed 2D or 3D images, and the identified components may be visually distinguished on a display 760. In some embodiments, the display 760 may be included as a component of the ablation system console 410 (shown in FIG. 3). In other embodiments, the display 760 may be an independently located device that communicates either wirelessly or through a wired connection with the ablation system 400. In some embodiments, the display 760 may be remotely located.

Based on the assessment of the scanned object or region of interest, the diagnostic logic 750 can be configured to generate a score indicating the level of ablation. For example, in one instance, if the scanned object of interest was a nerve or nerve bundle, a score of zero may indicate no ablation or a healthy nerve while a score of ten may indicate a high level of ablation or a non-conductive nerve. Depending upon the real-time score, the user and/or the processor 220 (shown in FIG. 1) may decide to continue ablative therapy at the same level of ablative energy, reduce the level of ablative energy, increase the level of ablative energy, or discontinue ablative therapy at that location. The score may also be recorded and stored in the memory 245, and later used to create an anatomical mapping of the ablation procedure. In one example, the user may set the desired score to a specific number, i.e. 6, and the system will continue ablation in a ROI until the score 6 is reached without user input.

For the example shown in FIG. 6, the tissue characterization 485 may output a tissue characterization of the object 405 as a vascular plaque 600 containing a focal area of calcification 605. Based on the tissue characterization 485 and/or the ablation assessment 755 (shown in FIG. 11), the user and/or the system 400 may alter the level of ablation applied next to the object 405. In some embodiments, the system may accomplish this by appropriately tuning the ablative element 180 and/or the amount of energy provided by the ablation source 225 (shown in FIG. 1). For example, in FIG. 6, once the tissue characterization of an area of calcification was reported by the characterization application 250, the user and/or the processor 220 may increase the level of ablative energy emitted from the ablative element 180 in order to more effectively ablate the calcified area 605.

FIGS. 12-14 illustrate advancement of the ablation catheter 110 and the modification of applied ablative energy through the occlusion 600. In FIG. 12, the catheter 110 is shown after having ablated through a portion of the calcific area 605. Based on the data received from the imaging apparatus 170, the tissue characterization 485 and, in some instances, the ablation assessment 755 can indicate that the ablative element 180 is now positioned adjacent to a softer area of necrotic tissue 720 having low to no levels of ablation. Based on this information, the user and/or the processor 220 can decrease the level of ablative energy emitted from the ablative element 180 in order to ablate and tunnel through the necrotic area 720. As the ablative element 180 ablates the necrotic area 720, the user may periodically image the area with the imaging apparatus 170 and reassess the appropriate level of ablation based on the current tissue characterization 485 and/or ablation assessment 755.

In FIG. 13, the catheter 110 is shown after having ablated through a portion of the calcific area 605 and the necrotic area 720. Based on the data received from the imaging apparatus 170, the tissue characterization 485 and, in some instances, the ablation assessment 755 can indicate that the ablative element 180 is now positioned adjacent to a harder area of calcific tissue 605 having low to no levels of ablation. Based on this information, the user and/or the processor 220 can increase the level of ablative energy emitted from the ablative element 180 in order to effectively ablate and tunnel through the calcific tissue 605 without penetrating the vessel wall.

In FIG. 14, the catheter 110 is shown after having ablated through the calcific area 605. Based on the data received from the imaging apparatus 170, the tissue characterization 485 and, in some instances, the ablation assessment 755 can indicate that the ablative element 180 is now positioned beyond the occlusion 600 within the lumen 445 of the vessel 450. Based on this information, the user and/or the processor 220 can stop the emission of ablative energy from the ablative element 180. In some instances, the user may ablate more of the occlusion 600 than is shown in FIG. 14. In other instances, the user may later insert other therapeutic devices, including, for example and without limitation, balloon catheters and stents, through a passageway 775 created by the ablation in order to further widen the passageways 775 and increase the cross-sectional area of the lumen 445.

In one particular embodiment, the present disclosure relates to an apparatus, systems, and methods of using and monitoring thermal energy neuromodulation for the treatment of various cardiovascular diseases, including, by way of non-limiting example, hypertension, chronic heart failure, and/or chronic renal failure, through tissue characterization. In some instances, embodiments of the present disclosure are configured to image and characterize tissue before, during, and/or after ablation of a carotid body. As shown in FIG. 15, a carotid body 800 lies deep to the bifurcation of each common carotid artery 805 into an internal carotid artery 806 and an external carotid artery 807. FIG. 15 illustrates the ablation catheter 110 positioned adjacent the carotid body 800 and within the left common carotid artery 805. The carotid body 800 is a small, flattened, oval structure, 2 to 5 mm in diameter, with a characteristic structure composed of epithelioid cells, which are in close relation to capillary sinusoids and an abundance of nerve fibers. Surrounding the carotid body 800 is a delicate fibrous capsule. The carotid body 800 is part of the visceral afferent system of the body, containing chemoreceptor endings that respond to low levels of oxygen or high levels of carbon dioxide and lowered pH of the blood. It is supplied by nerve fibers from both the glossopharyngeal nerve 810 and the vagus nerve 815. Specifically, the carotid body 800 detects changes in the composition of arterial blood flowing past it, and is also sensitive to changes in pH and temperature. Denervation of the carotid body has been associated with alleviation of hypertension.

In some instances, the catheter 110 may be used to ablate and monitor the ablation of the carotid body 800 to treat diseases associated at least in part with peripheral chemoreceptor hyperactivity or heightened sympathetic activity. The devices, systems, and methods of the present disclosure allow the user to appropriately reduce afferent nerve signaling from the carotid body by ablating it without inadvertently damaging the vessel wall of the carotid artery or destroying the carotid body. Thus, embodiments of the present disclosure allow the user to ablate the carotid body to a specific degree by monitoring the ablation process through tissue and ablation level characterization. Moreover, embodiments of the present disclosure may allow the user to selectively denervate the carotid body 800 (e.g., destroying afferent nerves from the carotid body while preserving nerves from the carotid sinus that conduct baroreceptor signals) by using imaging and tissue characterization to guide the ablation procedure.

In some instances, embodiments of the present disclosure are configured to image and characterize tissue during the delivery of thermal energy to the renal nerve plexus to decrease renal sympathetic activity. Renal sympathetic activity may worsen symptoms of hypertension, heart failure, and/or chronic renal failure. In particular, hypertension has been linked to increased sympathetic nervous system activity stimulated through any of four mechanisms, namely (1) increased vascular resistance, (2) increased cardiac rate, stroke volume and output, (3) vascular muscle defects, and/or (4) sodium retention and renin release by the kidney. As to this fourth mechanism in particular, stimulation of the renal sympathetic nervous system can affect renal function and maintenance of homeostasis. For example, an increase in efferent renal sympathetic nerve activity may cause increased renal vascular resistance, renin release, and sodium retention, all of which exacerbate hypertension.

Blood pressure is controlled by a complex interaction of electrical, mechanical, and hormonal forces in the body. The main electrical component of blood pressure control is the sympathetic nervous system (SNS), a part of the body's autonomic nervous system, which operates without conscious control. The sympathetic nervous system connects the brain, the heart, the kidneys, and the peripheral blood vessels, each of which plays an important role in the regulation of the body's blood pressure. The kidneys affect blood pressure by signaling the need for increased or lowered pressure through the SNS (electrical), by filtering blood and controlling the amount of fluid in the body (mechanical), and by releasing key hormones that influence the activities of the heart and blood vessels to maintain cardiovascular homeostasis (hormonal). The kidneys send and receive electrical signals from the SNS and thereby affect the other organs related to blood pressure control. They receive SNS signals primarily from the brain, which partially control the mechanical and hormonal functions of the kidneys. At the same time, the kidneys also send signals to the rest of the SNS, which can boost the level of sympathetic activation of all the other organs in the system, effectively amplifying electrical signals in the system and the corresponding blood pressure effects.

Thus, overactive sympathetic stimulation of the kidneys plays a significant role in the progression of hypertension, CHF, CRF, and other cardio-renal diseases. Heart failure and hypertensive conditions often result in abnormally high sympathetic activation of the kidneys, creating a vicious cycle of cardiovascular injury. An increase in renal sympathetic nerve activity leads to the decreased removal of water and sodium from the body, as well as increased secretion of renin, which leads to vasoconstriction of blood vessels supplying the kidneys. Vasoconstriction of the renal vasculature causes decreased renal blood flow, which causes the kidneys to send afferent SNS signals to the brain, triggering peripheral vasoconstriction and increasing a patient's hypertension. Reduction of sympathetic renal nerve activity, e.g., via renal neuromodulation or denervation of the renal nerve plexus, may reverse these processes.

By blocking afferent sympathetic activity from the kidney to the brain, renal denervation may lower the level of activation of the whole SNS. Thus, renal denervation may also decrease the electrical stimulation of other members of the sympathetic nervous system, such as the heart and blood vessels, thereby causing additional anti-hypertensive effects. In addition, blocking renal nerves may also have beneficial effects on organs damaged by chronic sympathetic overactivity, because it may lower the level of cytokines and hormones that may be harmful to the blood vessels, kidney, and heart.

Furthermore, because renal denervation reduces overactive SNS activity, it may be valuable in the treatment of several other medical conditions related to hypertension. These conditions, which are characterized by increased SNS activity, include left ventricular hypertrophy, chronic renal disease, chronic heart failure, insulin resistance (diabetes and metabolic syndrome), cardio-renal syndrome, osteoporosis, and sudden cardiac death. For example, other benefits of renal denervation may theoretically include: reduction of insulin resistance, reduction of central sleep apnea, improvements in perfusion to exercising muscle in heart failure, reduction of left ventricular hypertrophy, reduction of ventricular rates in patients with atrial fibrillation, abrogation of lethal arrhythmias, and slowing of the deterioration of renal function in chronic kidney disease. Moreover, chronic elevation of renal sympathetic tone in various disease states that exist with or without hypertension may play a role in the development of overt renal failure and end-stage renal disease. Because the reduction of afferent renal sympathetic signals contributes to the reduction of systemic sympathetic stimulation, renal denervation may also benefit other organs innervated by sympathetic nerves. Thus, renal denervation may also alleviate various medical conditions, even those not directly associated with hypertension.

Thermal neuromodulation by either intravascular ablation (e.g., heating or cooling) may decrease renal sympathetic activity by disabling the efferent and/or afferent sympathetic nerve fibers that surround the renal arteries and innervate the kidneys through renal denervation, which involves selectively disabling renal nerves within the SNS to create at least a partial conduction block within the SNS. Thermal neuromodulation is due at least in part to the thermally-induced alterations of the neural structures themselves. Additionally or alternatively, the thermal neuromodulation may be due at least in part to the thermally-induced alteration of vascular structures, e.g. arteries, arterioles, capillaries, and/or veins, which perfuse the neural fibers surrounding the target area. Additionally or alternatively, the thermal neuromodulation may be due at least in part to the electroporation of the target neural fibers.

FIG. 16 illustrates a portion of a thermal basket catheter 850 in an expanded condition positioned within the human renal anatomy. The human renal anatomy includes kidneys 852 that are supplied with oxygenated blood by right and left renal arteries 854, which branch off an abdominal aorta 856 at the renal ostia 858 to enter the hilum 858 of the kidney 852. The abdominal aorta 856 connects the renal arteries 854 to the 860 and an inferior vena cava 862. Specifically, the thermal basket catheter 850 is shown extending through the abdominal aorta and into the left renal artery 854. In alternate embodiments, the thermal basket catheter may be sized and configured to travel through the inferior renal vessels 864 as well. The thermal basket catheter 850 is substantially similar to the ablation catheter 110 except for the differences described below. The thermal basket catheter 850 will be described in more detail below with respect to FIGS. 19-28 and 30. In some instances, the thermal basket catheter 850 includes components or features similar or identical to those disclosed in U.S. patent application Ser. No. 13/458,856, entitled "Methods and Apparatus for Renal Neuromodulation," filed Apr. 27, 2012, which is hereby incorporated by reference in its entirety.

Left (not shown) and right renal plexi or nerves 870 surround the left and right renal arteries 854, respectively. Anatomically, the renal nerve 870 forms one or more plexi within the adventitial tissue surrounding the renal artery 854. For the purpose of this disclosure, the renal nerve is defined as any individual nerve or plexus of nerves and ganglia that conducts a nerve signal to and/or from the kidney 852 and is anatomically located on the surface of the renal artery 854, parts of the abdominal aorta 856 where the renal artery 854 branches off the aorta 856, and/or on inferior branches of the renal artery 854.

Proper renal function is essential to maintenance of cardiovascular homeostasis so as to avoid hypertensive conditions. Excretion of sodium is key to maintaining appropriate extracellular fluid volume and blood volume, and ultimately controlling the effects of these volumes on arterial pressure. Under steady-state conditions, arterial pressure rises to that pressure level which results in a balance between urinary output and water and sodium intake. If abnormal kidney function causes excessive renal sodium and water retention, as occurs with sympathetic overstimulation of the kidneys through the renal nerves 120, arterial pressure will increase to a level to maintain sodium output equal to intake. In hypertensive patients, the balance between sodium intake and output is achieved at the expense of an elevated arterial pressure in part as a result of the sympathetic stimulation of the kidneys through the renal nerves 120. Thermal neuromodulation of the renal nerves 120 may help alleviate the symptoms and sequelae of hypertension by blocking or suppressing the efferent and afferent sympathetic activity of the kidneys 10.

FIG. 17 illustrates a segment of the renal artery 854 in greater detail, showing various intraluminal characteristics and intra-to-extraluminal distances that may be present within a single vessel. In particular, the renal artery 854 includes a lumen 872 that extends lengthwise through the renal artery along a longitudinal axis LA. The lumen 872 is a tube-like passage that allows the flow of oxygenated blood from the abdominal aorta to the kidney. The sympathetic renal nerves 870 extend generally within the adventitia (not shown) surrounding the renal artery 854, and include both the efferent (conducting away from the central nervous system) and afferent (conducting toward the central nervous system) renal nerves.

The renal artery 854 includes a first portion 874 having a generally healthy luminal diameter D1 and an intra-to-extraluminal distance D2, a second portion 876 having a narrowed and irregular lumen and an enlarged intra-to-extraluminal distance D3 due to atherosclerotic changes in the form of plaques 880, 882, and a third portion 878 having a narrowed lumen and an enlarged intra-to-extraluminal distance D2' due to a thickened arterial wall 884. Thus, the intraluminal contour of a vessel, for example, the renal artery 854, may be greatly varied along the length of the vessel. Variable intra-to-extraluminal distances along the length of the vessel may affect the treatment protocols for implementing thermal neuromodulation at different portions of the vessel at least because the amount of thermal energy necessary to travel the intra-to-extraluminal distance to affect neural tissue surrounding the vessel varies with varying intra-to-extraluminal distances. As described further below in relation to FIGS. 29*a* and 29*b*, the thermal basket catheters disclosed herein may aid in determining appropriate and effective treatment protocols by pre-treatment, in-treatment, and post-treatment imaging and sensing of various characteristics, including the extent or level of ablation.

FIGS. 18*a*, 18*b*, and 18*c* illustrate the portions 874, 878, 876, respectively, of the renal artery 854 in perspective view, showing the sympathetic renal nerves 870 that line the renal artery 854. FIG. 18*a* illustrates the portion 874 of the renal artery 854 including the renal nerves 870, which are shown schematically as a branching network attached to the external surface of the renal artery 854. The renal nerves 870 extend generally lengthwise along the longitudinal axis LA of renal artery 854. In the case of hypertension, the sympathetic nerves that run from the spinal cord to the kidneys 852 signal the body to produce norepinephrine, which leads to a cascade of signals ultimately causing a rise in blood pressure. Neuromodulation of the renal nerves 870 (or renal denervation) removes or diminishes this response and facilitates a return to normal blood pressure.

The renal artery 854 has smooth muscle cells 886 that surround the arterial circumference and spiral around the angular axis $\theta$ of the artery. The smooth muscle cells 886 of the renal artery 854 have a longer dimension extending transverse (i.e., non-parallel) to the longitudinal axis LA of the renal artery 854. The misalignment of the lengthwise dimensions of the renal nerves 870 and the smooth muscle cells 886 is defined as "cellular misalignment." This cellular misalignment of the renal nerves 870 and the smooth muscle cells 886 may be exploited to selectively affect renal nerve cells with a reduced effect on smooth muscle cells.

In FIG. 18*a*, the first portion 874 of the renal artery 854 includes a lumen 888 that extends lengthwise through the renal artery along the longitudinal axis LA. The lumen 888 is a generally cylindrical passage that allows the flow of oxygenated blood from the abdominal aorta to the kidney. The lumen 888 includes a luminal wall 884 that forms the blood-contacting surface of the renal artery 854. The distance D1 corresponds to the luminal diameter of lumen 888 and defines the diameter or perimeter of the blood flow lumen. A distance D2, corresponding to the wall thickness, exists between the luminal wall 884 and the renal nerves 870. The relatively healthy renal artery 854 may have an almost uniform distance D2 or wall thickness with respect to the lumen 888. The relatively healthy renal artery 854 may decrease substantially regularly in cross-sectional area and volume per unit length, from a proximal portion near the aorta to a distal portion near the kidney.

FIG. 18*b* illustrates the third portion 878 of the renal artery 854 including a lumen 888' that extends lengthwise through the renal artery along the longitudinal axis LA. The lumen 888' includes a luminal wall 884' which forms the blood-contacting surface of the renal artery 854 at the third portion 878. In some patients, the smooth muscle wall of the renal artery is thicker than in other patients, and consequently, as illustrated in FIG. 18*b*, the lumen of the third portion 878 of the renal artery 854 possesses a smaller diameter relative to the renal arteries of other patients. The lumen 888', which is smaller in diameter and cross-sectional area than the lumen 888 pictured in FIG. 18*a*, is a generally cylindrical passage that allows the flow of oxygenated blood from the abdominal aorta to the kidney. A distance D2' exists between the luminal wall 884' and the renal nerves 870 that is greater than the distance D2 pictured in FIG. 18*a*.

FIG. 18*c* illustrates the diseased second portion 876 of the renal artery 854 including atherosclerotic changes. The second portion 876 includes a lumen 888" that extends lengthwise through the renal artery along the longitudinal axis LA. Unlike the renal artery of a patient without atherosclerotic changes, as is pictured in FIGS. 18*a* and 18*b*, the lumen 888" is an irregularly-shaped passage that may allow the flow of oxygenated blood from the abdominal aorta to the kidney at a reduced rate because the narrowed lumen creates a reduced cross-sectional area for blood flow. The lumen 888" includes a luminal wall 884" which forms the blood-contacting surface of the renal artery 854 at the second portion 876. The luminal wall 884" is irregularly shaped by the presence of two atherosclerotic plaques 880, 882. A distance D3 exists between the luminal wall 884" and the renal nerves 870 that is greater than the distance D2 pictured in FIG. 18*a*.

In FIG. 18*c*, the atherosclerotic plaque 880 is a predominantly fatty plaque in the earlier stages of plaque formation. The atherosclerotic plaque 882 is a hardened, calcified plaque in the later stages of plaque formation. The distance D3 extending from the luminal wall 884" to the renal nerves ranges in thickness along the circumferential and longitudinal span of the plaques 880, 882. Different types of plaques may possess different conductive and impedance properties, thereby affecting the amount, type, and duration of thermal energy that may be required to effectively modulate the nerves overlying the vessels in the region of the plaques.

FIG. 19 illustrates the thermal basket catheter 850 that is configured to deliver a thermal electric field to renal nerve fibers in order to achieve renal neuromodulation via heating and/or cooling (i.e., through ablation) according to one embodiment of the present disclosure. The thermal basket catheter 850 is substantially similar to the ablation catheter 110 except for the differences described below. The thermal basket catheter 850 comprises an elongate, flexible, tubular body 920 that is configured for intravascular placement and defines an internal lumen 925. The body 920 extends from a handle 930 along a longitudinal axis CA, which is coupled to an interface 940 by an electrical connection 945. The body 920 includes a proximal portion 950, and intermediate portion 955, and a distal portion 960. In FIG. 19, the thermal basket catheter 850 is pictured in an unexpanded condition. The proximal portion 950 may include shaft markers 962 to aid in positioning the catheter in the body of a patient. The intermediate portion 955 may include a guidewire exit port 965 from which a guidewire may emerge. The distal portion 960 may include several radiopaque markers 970, an imaging apparatus 980, and a distal tip 990. In addition, the distal portion 960 comprises an expandable structure 1000 (not shown in FIG. 19) in an unexpanded condition within the body 920, located within the distal portion 960 and proximal to the distal tip 990. The imaging apparatus 980 is positioned on a proximal segment of the distal tip 090, which may be axially spaced from the rest of the body 920 along the longitudinal axis CA to reveal the expandable structure 1000 in a gradually expanding condition.

The interface 940 is configured to connect the catheter 850 to the ablation system 100 described above in reference to FIG. 1. More specifically, in some instances the interface 940 is configured to communicatively connect at least the imaging apparatus 980 and the expandable structure 1000 of the catheter 850 to the controller 210 suitable for carrying out imaging and thermal neuromodulation. The interface 940 may also be configured to include a plurality of electrical connections, each electrically coupled to an electrode and/or a sensor on the expandable structure 1000 via a dedicated conductor and/or a sensor cable (not shown), respectively, running through the body 920 as described in more detail below with respect to FIG. 12. Such a configuration allows for a specific group or subset of electrodes on the expandable structure 1000 to be easily energized with either monopolar or bipolar energy, for example. Such a configuration may also allow the expandable structure 1000 to transmit data from any of a variety of sensors via the controller 210 to data display modules such as the GUI 215 and/or the processor 220. The interface 940 may be coupled to the ablation source 225 via the controller 210, with the controller 210 allowing energy to be selectively directed to the portion of a luminal wall of the renal artery that is engaged by the expandable structure 1000 while in an expanded condition.

In the pictured embodiment, the ablation source 225 is configured to produce thermal energy, e.g. RF energy, that may be directed to the expandable structure 1000 when it assumes an expanded condition. Under the control of the user or an automated control algorithm in the processor 220, the ablation source 225 generates a selected form and magnitude of thermal energy. The ablation source 225 may be utilized with any of the thermal basket catheters described herein for delivery of a thermal electric field with the desired field parameters, i.e., parameters sufficient to thermally induce renal neuromodulation via heating, cooling, and/or other mechanisms such as electroporation. It should be understood that the thermal basket catheters described herein may be electrically connected to the ablation source 225 even through the ablation source 225 is not explicitly shown or described with respect to each embodiment. The user may direct whether the expandable structure 1000 is energized with monopolar or bipolar RF energy by using the controller 210 or programming the processor 220.

FIG. 19 illustrates the thermal basket catheter 850 in an unexpanded condition according to one embodiment of the present disclosure. The thermal basket catheter includes the expandable structure 1000 in an unexpanded condition positioned within the distal portion 960. As described above, the body 920 is an elongate flexible tube that defines the lumen 925 and the longitudinal axis of the catheter CA. The body 920 is configured to flex in a substantial fashion to traverse tortuous intravascular pathways and gain entrance to the renal arteries. The lumen 925 may be used for the delivery of thermal energy, for sensing various characteristics, and for imaging the vascular and neural anatomy. The lumen 925 may also be used as an access lumen for a guidewire. In some embodiments, the lumen 925 may be used for irrigation of a vessel lumen and aspiration of cellular debris, such as plaque material. In some embodiments, the body 920 includes more than one lumen.

As described above, the proximal portion 950 may include shaft markers 962 disposed along the body of the catheter 850 that aid in positioning the catheter in the body of a patient. The shaft markers 962 may be positioned a specific distance from each other and comprise a measurement scale reflecting the distance of the marker 962 from the expandable structure 1000. The proximal portion 950 may include any number of shaft markers 962 positioned a fixed distance away from the expandable structure 1000 associated with a range of expected distances from the patient's skin surface at the point of catheter entry to the desired zone of thermal neuromodulation. For example, the shaft markers may be positioned, by way of non-limiting example, 1 millimeter from each other, 1 centimeter from each other, and/or 1 inch from each other. After initially positioned the expandable structure within the target vessel for neuromodulation, the user may utilize the shaft markers 962 to knowledgeably shift or reposition the catheter 850 along the intravascular target vessel to apply thermal energy at desired intervals along the target vessel before, after, or without employing imaging guidance. By noting the measurement and/or change in measured distance indicated by the shaft markers located immediately external to the patient's body as the catheter 850 is shifted, the user may determine the approximate distance and axial direction the expandable structure 1000 has shifted within the patient's vasculature. In addition, the user may use the measurement and/or change in measured distance indicated by the shaft markers located immediately external to the patient's body to cross reference the intravascular position of the expandable structure 1000 indicated by intravascular imaging. In some embodiments, the shaft markers 962 may be radiopaque or otherwise visible to imaging guidance. Other embodiments may lack shaft markers.

As described above, the intermediate portion 955 may include a guidewire exit port 965 from which a guidewire may emerge. The structure and function of the guidewire exit port 965 will be described in further detail below with respect to FIGS. 21-25.

The radiopaque markers 970 are spaced along the distal portion 960 at specific intervals from each other and at a specific distance from the distal tip 990. The radiopaque markers 970 may aid the user in visualizing the path and ultimate positioning of the catheter 850 within the vasculature of the patient. In addition, the radiopaque markers 970 may provide a fixed reference point for co-registration of various imaging modalities and treatments, including by way of non-limiting example, external imaging including angiography and fluoroscopy, imaging by the imaging apparatus 980, and thermal neuromodulation by the expandable structure 1000. Other embodiments may lack radiopaque markers.

The imaging apparatus 980 is substantially similar to the imaging apparatus 180 described above in relation to FIG. 1 except for the differences described below. In the pictured embodiment, the imaging apparatus 980 is an intravascular ultrasound (IVUS) apparatus. More specifically, the imaging apparatus 980 pictured in FIG. 19 represents an ultrasound transducer. The entire IVUS apparatus may extend through the body 920 and include all the components associated with an IVUS module, such as a transducer(s), multiplexer(s), electrical connection(s), etc., for performing IVUS imaging. The imaging apparatus 980 of the pictured embodiment may utilize any IVUS configuration that allows at least a portion of the body 920 to be introduced over a guidewire. For example, in some instances, the imaging apparatus 980 utilizes an array of transducers (e.g., 32, 64, 128, or other number transducers) disposed circumferentially about the central lumen 925 of the body 920 in a fixed orientation. In other embodiments, the IVUS portion 118 is a rotational IVUS system. In some instances, the imaging apparatus 980 includes components similar or identical to those found in IVUS products from Volcano Corporation, such as the Eagle Eye® Gold Catheter, the Visions® PV8.2F Catheter, the Visions® PV 018 Catheter, and/or the Revolution® 45 MHz Catheter, and/or IVUS products available from other manufacturers. Further, in some instances the catheter 850 includes components or features similar or identical to those disclosed in U.S. Pat. Nos. 4,917,097, 5,368,037, 5,453,575, 5,603,327, 5,779,644, 5,857,974, 5,876,344, 5,921,931, 5,938,615, 6,049,958, 6,0854,109, 6,123,673, 6,165,128, 6,283,920, 6,309,339; 6,033,357, 6,457,365, 6,712,767, 6,725,081, 6,767,327, 6,776,763, 6,779,257, 6,7854,157, 6,899,682, 6,962,567, 6,976,965, 7,097,620, 7,226,417, 7,641,4854, 7,676,910, 7,711,413, and 7,736,317, each of which is hereby incorporated by reference in its entirety.

In alternate embodiments, the imaging apparatus 980 may be or include, by way of non-limiting example, any of grey-scale IVUS, forward-looking IVUS, rotational IVUS, phased array IVUS, solid state IVUS, or optical coherence tomography. It is understood that, in some instances, wires associated with the imaging apparatus 980 extend along the length of the elongated tubular body 920 through the handle 930 and along electrical connection 945 to the interface 940 such that signals from the imaging apparatus 980 can be communicated to the controller 210. In some instances, the imaging apparatus 980 communicates wirelessly with the controller 210 and/or the processor 220.

In alternate embodiments, the imaging apparatus 980 may work in cooperation with or be substituted by an independent imaging catheter that is threaded through the lumen 925 of the catheter 850. In such embodiments, the independent imaging catheter may be axially moveable and rotational within the body 920 such that the imaging components of the imaging catheter may be positioned in a multitude of places along the longitudinal axis CA relative to the expandable structure 1000. For example, a distal tip of the imaging catheter may be positioned proximal, within, or distal to the expandable structure 1000 to gather image data about the surrounding tissue. In an embodiment where the imaging catheter is positioned within the expandable structure, the expandable structure may be constructed of translucent material or material that does not interfere with the data collection of the imaging catheter.

With reference to FIG. 20b, in alternate embodiments, the imaging apparatus 980 may work in cooperation with or be substituted by a central imaging apparatus 1001, which may be positioned on an exterior surface of an inner body 1005 of the body 920. The central imaging apparatus 1001 may be configured to function in substantially the same manner as the imaging apparatus 980.

The proximal portion 950 of the body 920 connects to the handle 930, which is sized and configured to be securely held and manipulated by a user outside a patient's body. By manipulating the handle 930 outside the patient's body, the user may advance the body 920 of the catheter 850 through an intravascular path and remotely manipulate or actuate the distal portion 960. In the pictured embodiment, the handle 930 includes an elongated, slidable body actuator 1010 positioned within an actuator recess 1011. The body actuator 1010 may be configured as any of a variety of elements, including by way of non-limiting example, a knob, a pin, or a lever, capable of manipulating or actuating the distal portion 960 to reveal the expandable structure 1000. The operation of the body actuator 1010 will be further described below with respect to FIGS. 20b and 21.

In alternate embodiments, the handle 930 may include a proximal port configured to receive fluid therethrough, thereby permitting the user to irrigate or flush the lumen 925 and/or the expandable structure 1000. For example, the proximal port may include a Luer-type connector capable of sealably engaging an irrigation device such as a syringe. Image guidance using the imaging apparatus 980 or external imaging, e.g., radiographic, CT, or another suitable guidance modality, or combinations thereof, can be used to aid the user's manipulation of the catheter 850. In the pictured embodiment, the body 920 is integrally coupled to the handle 930. In other embodiments, the body 920 may be detachably coupled to the handle 930, thereby permitting the body 920 to be replaceable.

The catheter 850, or the various components thereof, may be manufactured from a variety of materials, including, by way of non-limiting example, plastics, polytetrafluoroethylene (PTFE), polyether block amide (PEBAX), thermoplastic, polyimide, silicone, elastomer, metals, such as stainless steel, titanium, shape-memory alloys such as Nitinol, and/or other biologically compatible materials. In addition, the catheter 850 may be manufactured in a variety of lengths, diameters, dimensions, and shapes. For example, in some embodiments the elongated body 920 may be manufactured to have length ranging from approximately 115 cm-155 cm. In one particular embodiment, the elongated body 920 may be manufactured to have length of approximately 872 cm. In some embodiments, the elongated body 920 may be manufactured to have a transverse dimension ranging from approximately 1 mm-2.67 mm (3 Fr-8 Fr). In one embodiment, the elongated body 920 may be manufactured to have a transverse dimension of 2 mm (6 Fr), thereby permitting the catheter 850 to be configured for insertion into the renal vasculature of a patient. These examples are provided for illustrative purposes only, and are not intended to be limiting.

FIG. 20a illustrates at least a segment of the distal portion 960 of the thermal basket catheter 850 in an unexpanded condition according to one embodiment of the present disclosure. In some instances, the thermal basket catheter 850 includes components or features similar or identical to those disclosed in U.S. Patent Application Publication No. US2004/0176699, which is hereby incorporated by reference in its entirety. In the pictured embodiment, the distal tip 990 is positioned against the remainder of the body along the longitudinal axis CA, and the expandable structure 1000 is compressed within the lumen in an unexpanded condition. The distal portion 960 includes a distal connection part 1015, which is the proximal-most part of the distal tip 990, and a proximal connection part 1020, which abuts the distal connection part 1015 when the catheter 850 is in an unexpanded condition. In the pictured embodiment, the imaging apparatus 980 is positioned distal to the distal connection part 1015. Additionally or alternatively, the imaging apparatus may be positioned proximal to the proximal connection part 1020.

FIG. 20b illustrates at least a segment of the distal portion 960 of the thermal basket catheter 850 in an unexpanded condition according to one embodiment of the present disclosure. In the pictured embodiment, the distal tip 990 is moved distally away from the remainder of the body along the longitudinal axis CA to allow the expandable structure 1000 to emerge from the lumen and assume an expanded condition. Specifically, the distal connection part 1015 is separated axially away from the proximal connection part 1020 along the axis CA. The user may transition the catheter 850 from an unexpanded condition to an expanded condition by manipulating the body actuator 1010 within the actuator recess 1011 to cause the distal tip 990 to move distally away from the remainder of the body 920. In the pictured embodiment, the expandable structure 1000 is shown in a deployed and expanded condition wherein at least one support arm 1025 has expanded outwardly. The expandable structure 1000 includes six flexible support arms 1025. In other embodiments, the expandable structure may include any number of support arms 1025. At least one electrode 1030 and at least one sensor 1035 may be positioned on at least one of the support arms 1025. The at least one electrode 1030 comprises an ablative element. The at least one electrode 1030 and at least one sensor 1035 will be described in further detail below with reference to FIGS. 26 and 27.

The support arms 1025 may be manufactured from a variety of biocompatible materials, including, by way of non-limiting example, superelastic or shape memory alloys such as Nitinol, and other metals such as titanium, Elgiloy®, and/or stainless steel. The support arms 1025 could also be made of, by way of non-limiting example, polymers or polymer composites that include thermoplastics, resins, carbon fiber, and like materials. In the illustrated embodiment, the support arms 1025 are secured to a deployment support member 1040, which may be secured to an interior component of the body 920 in a variety of ways, including by way of non-limiting example, adhesively bonded, laser welded, mechanically coupled, or integrally formed. In alternate embodiments, the support arms 1025 may be secured to an interior component of the body 920 directly, thereby eliminating the need for a deployment support member 1040.

FIG. 21 illustrates the thermal basket catheter 850 in an unexpanded condition prior to deployment of the expandable structure 1000 according to one embodiment of the present disclosure. More specifically, FIG. 21 illustrates a segment of the body 920 in an unexpanded condition, including a segment of the intermediate portion 955 and a segment of the distal portion 960. The expandable structure 1000 is positioned proximate to the distal portion 960 of the catheter 850. As mentioned above, the intermediate portion 955 of the body may include the guidewire exit slot 965 thereon. The distal tip 990 of the distal portion 960 may include at least one guidewire port 1045 capable of receiving a guidewire 1050 therein.

FIG. 22 illustrates a transverse cross-sectional view of the body 920 of the thermal basket catheter 850 as taken along the lines 22-22 of FIG. 21 according to one embodiment of the present disclosure. FIG. 23 illustrates the expandable structure 1000 in a non-deployed and unexpanded condition according to one embodiment of the present disclosure. As shown in FIGS. 22 and 23, the elongated body 920 may include an outer sleeve 1055 forming a sleeve lumen 1060 and housing an inner body 1065 therein. In one embodiment, the outer sleeve 1055 may be manufactured from a material, such as PEBAX, having a wall thickness of about 0.0127 mm to about 0.0762 mm. In another embodiment, the outer sleeve 1055 has a wall thickness of about 0.0381 mm to about 0.0635 mm. These ranges are provided for illustrative purposes only, and are not intended to be limiting.

As shown in FIG. 23, the expandable structure 1000 of the catheter 850 may be positioned within the sleeve lumen 1060 formed by the outer sleeve 1055 prior to deployment. As shown, the expandable structure 1000 may be compressed inwardly by an inner surface of the outer sleeve 1055 and located within the sleeve lumen 1060. In an alternate embodiment, the elongated body 920 may be manufactured without an outer sleeve. The inner body 1065 defines an internal passage 1070 therein. In the illustrated embodiment, the internal passage 1070 is formed within the inner body 1065, however, the internal passage may not be present in some embodiments. In another embodiment, the inner body 1065 may define a plurality of internal passages therein. The internal passage 1070 formed in the inner body 1065 may be in communication with the guidewire port 1045 located on the distal tip 990 and may be capable of receiving the guidewire 1050 therein (as shown in FIG. 21).

As shown in FIG. 21, the expandable structure 1000 is positioned proximate to the distal portion 960 of the catheter 850. Returning to FIG. 23, the expandable structure is compressed inwardly by an inner surface of the outer sleeve 1055. The outer sleeve 1055 may be in communication with or attached to the elongated body actuator 1010 positioned within the actuator recess 1011 located on the handle 930 (as illustrated in FIG. 19). The rearward movement of the elongated body actuator 1010 within the actuator recess 1011 results in the outer sleeve 1055 retracting rear-wardly from the distal tip 990, thereby permitting the expandable structure 1000 to expand radially and assume an expanded condition.

In an alternate embodiment, the outer sleeve 1055 may remain stationary while the inner body 1005 may be capable of moving in telescopic relation thereto. For example, the inner body 1005 may communicate with the elongated body actuator 1010 (as illustrated in FIG. 19). The forward movement of the elongated body actuator 1010 within the actuator recess 1011 results in the inner body 1005 extending distally from the handle 930 (as illustrated in FIG. 20b), thereby advancing the expandable structure 1000 beyond the outer sleeve 1055 and permitting the expandable structure 1000 to expand radially (to contact the luminal wall of an artery, for example).

Both FIGS. 24 and 25 illustrate a distal segment of the thermal basket catheter 850 in an unexpanded condition according to one embodiment of the present disclosure. As shown in FIG. 24, a guidewire lumen 1075 may be secured to the guidewire port 1045 on the distal tip 990. A proximal end of the guidewire lumen 1075 communicates with a guidewire exit port 1080 in the inner body 1005, thereby permitting the guidewire port 1045 to communicate with the guidewire exit slot 965. The guidewire lumen 1075 may be secured to the guidewire port 1045 using, by way of non-limiting example, adhesives or bonding agents, mechanical couplers, pins, snap-fit devices, and other coupling devices known in the art.

As a shown in FIG. 25, the guidewire 1050 may be introduced into the guidewire port 1045 and made to traverse the guidewire lumen 1075 within the inner body 1005, exiting the catheter 850 through the guidewire exit port 1080 positioned in the guidewire exit slot 965. The guidewire exit slot 965 may be formed at a variety of distances along the elongated body 920. In some embodiments the distance between the guidewire port 1045 and the guidewire exit slot 965 ranges from about 10 cm to about 20 cm. For example, in one embodiment the distance between the guidewire port 1045 and the guidewire exit slot 965 ranges from about 10 cm to about 12 cm. These examples are provided for illustrative purposes only, and are not intended to be limiting.

FIG. 26 illustrates the thermal basket catheter 850 in an expanded condition according to one embodiment of the present disclosure wherein the distal tip 990 has been moved axially away from the remainder of the distal portion 960 and at least one of the support arms 1025 has expanded outwardly. The support arms 1025 may be manufactured in any of a variety of shapes, including by way of non-limiting example, arcuate shapes, bell shapes, smooth shapes, and step-transition shapes. The support arms include a proximal section 1100, a medial section 1105, and a distal section 1110. The proximal section 1100 may be capable of coupling the expandable structure 1000 to the body 920 or the inner body 1005. The medial section 1105 is configured to be positioned proximate to or in contact with a vessel luminal wall. The distal section 1110 couples each arm 1025 to a support arm retainer 1115 positioned on an exterior of the inner body 1005.

The transverse or cross-sectional profile of the support arms 1025 may be manufactured in any of a variety of shapes, including oblong, ovoid, and round. In some embodiments, the cross-sectional profile of the support arm includes rounded or atraumatic edges to minimize damage to an artery or a tubular structure through which the expandable structure 1000 may travel.

In one embodiment, the proximal sections 1100 of the support arms 1025 may be coupled to the deployment support member 1040 using an adhesive, such as, by way of non-limiting example, Loctite 3311 adhesive or any other biologically compatible adhesive. In an alternate embodiment, the expandable structure 1000 may be manufactured by laser cutting or forming the at least one support arm 1025 from a substrate. For example, any number of support arms 1025 may be laser cut within a Nitinol tube or cylinder, thereby providing a slotted expandable body. The support arms 1025 may be fabricated from a self-expanding material biased such that the medial section 1105 expands into contact with the vessel luminal wall upon expanding the catheter 850. In some embodiments, the one or more support arms 1025 may be formed in a deployed state as shown in FIG. 26 wherein at least one support arm 1025 is flared outwardly from the longitudinal axis CA of the catheter 850.

In the illustrated embodiment, the guidewire lumen 1075, capable of receiving the guidewire 1050 therein, longitudinally traverses the expandable structure 1000. The guidewire lumen 1075 is in communication with the guidewire port 1045 on the distal portion 960 and guidewire exit slot 965 located on the elongated body 920. In an alternate embodiment, the guidewire lumen 1075 may be in communication with the guidewire port 1045 on the distal tip 990 and/or a proximal port located on the handle 930 (shown in FIG. 19). In the illustrated embodiment, a retainer sleeve 1120 is positioned over a distal section of the support arms 1025 to provide a transition between the distal tip 990 and the support arms 1025. As shown, the retainer sleeve 1120 is positioned over the support arm retainers 1115, thereby preventing the support arm retainers 540 from contacting the vessel wall and causing trauma to the vessel luminal wall, damaging the support arm retainers 1115, or both. Other embodiments may lack a retainer sleeve.

During manufacture, the at least one support arm 1025 is formed to assume a deployed position in a relaxed state as shown in FIG. 26, wherein the medial section 1105 of the support arm 1025 is flared outwardly a distance D from the longitudinal axis CA of the catheter 850. The application of force to the apex of the medial section 1105 of the support arm 1025 decreases the curvature of the support arm 1025 resulting in a corresponding decrease in the distance D.

The at least one electrode 1030 may be positioned on the medial section 1105 of at least one of the support arms 1025, thereby enabling the electrode 1030 to contact or approximate the vessel luminal wall. At least one electrode cable 1125 connects each electrode 1030 to the interface 940 and/or the ablation source 225.

The at least one sensor 1035 may be positioned on the medial section 1105 of at least one of the support arms 1025, thereby enabling the sensor to contact or approximate the vessel luminal wall. At least one sensor cable connects each sensor 1035 to the sensor coupler and/or the interface 940.

The expandable structure 1000 may include at least one ancillary sensor 1140 thereon. As shown in FIG. 26, the ancillary sensor 1140a may be positioned on an exterior surface of the inner body 1005. In the alternative, at least one ancillary sensor 1140b may be positioned on at least one support arm 1025. Exemplary ancillary sensors 1140 include, without limitation, ultrasonic sensors, flow sensors, thermal sensors, blood temperature sensors, electrical contact sensors, conductivity sensors, electromagnetic detectors, pressure sensors, chemical or hormonal sensors, pH sensors, and infrared sensors. For example, in one embodiment the ancillary sensor 1140a may comprise a blood sensor positioned on the guidewire lumen 1075 in the bloodstream as shown in FIG. 26, thereby permitting the sensors 1035 located on the support arms 1025 to measure the vessel wall temperature while simultaneously the ancillary sensor 1140a measures blood temperature within the vessel. In another embodiment, the ancillary sensor 1140b may comprise a pressure sensor positioned on the support arm 1025 proximate to the electrode 1030 and/or encircling the electrode 1030. The ancillary pressure sensor 1140b may detect the pressure with which the proximate electrode 1030 is contacting the vessel wall, thereby allowing the user to determine whether the electrode 1030 is effectively contacting the vessel wall to ensure adequate energy transfer and ablation (or neuromodulation).

In the embodiment illustrated in FIG. 26, each support arm 1025 is coupled by its distal section 1110 to inner body 1005 using the support arm retainer 1115, thereby permitting each support arm 1025 to move independently relative to the inner body 1005 and the other support arms 1025. The ability of the support arms 1025 to independently move within the support arm retainer 1115 results in the creation of an expandable structure 1000 offering flexibility, while permitting the support arms 1025 to remain in contact with a vessel wall (not shown) when traversing a tortuous or curved pathway, such as may be found in the renal arteries. More particularly, when the expandable structure 1000 is in a non-deployed state, the ability of the support arms 1025 to move independently of each other in an axial direction reduces shear resistance and results in a more flexible catheter than a catheter wherein the axial movement is coupled or otherwise restricted. In addition, when the expandable structure 1000 is in a deployed and expanded state, the ability of the support arms 1025 to move independently facilitates contact of each of the support arms 1025 with the vessel wall without applying excessive force thereto, thereby decreasing or eliminating the likelihood of injury to the vessel. Maximizing contact of each of the support arms 1025 with the vessel wall in turn maximizes contact of sensors 1035 with the vessel wall, which can be important in some embodiments for obtaining accurate sensor readings.

Referring again to FIG. 26, the ability of support arms 1025 to move independently with respect to the inner body 1005 and the other support arms 1025 results in the formation of a flexible expandable structure 1000 capable of traversing tortuous vessel pathways. The support arms 1025 of the expandable structure 1000 may be manufactured in a variety of shapes, lengths, widths, and thickness to promote the flexibility of the individual support arms 1025. A high degree of flexibility of the support arms helps to ensure the atraumatic deployment and movement of the expandable structure 1000 within a vessel lumen or tubular structure. For example, in one embodiment the support arms 1025 may have a length of about 5 mm to about 26 mm, and more specifically, a length of about 10 mm to about 16 mm. Similarly, the support arms 1025 may be manufactured from a material having a thickness of about 0.0381 mm to about 0.1778 mm. More specifically, in one embodiment, the support arms 1025 have a thickness of about 0.0635 mm to about 0.1878 mm. These ranges are provided for illustrative purposes only, and are not intended to be limiting.

FIG. 27 illustrates the expandable structure 1000 removed from the catheter 850 and in an expanded condition according to one embodiment of the present disclosure. The expandable structure 1000 may be generally hollow in design and may define an expandable body passage 1150 capable of receiving the guidewire 32 or the inner body 1005 therethrough (see FIG. 12). In some embodiments, the expandable structure 1000 may be sized and configured for expansion, manipulation, and use within a renal artery. The expandable structure 1000 may include any number of support arms 1025 separated by one or more spaces 1060.

The arms 1025 may be structurally supported with an insulated material such as, by way of non-limiting example, an ultraviolet cure or heat shrink sleeve, polyethelene, Nylon™, or the like. In the illustrated embodiment, the support arms 1025 are symmetrically positioned around the expandable body passage 1150. In an alternate embodiment, the support arms 1025 are asymmetrically positioned around the expandable body passage 1150. As stated above, the expandable structure 1000 may be manufactured from a variety of materials, including, for example, shape memory alloys such as Nitinol, metals such as stainless steel and titanium, polymers, composite materials, and like materials. In one embodiment, the expandable structure 1000 may be formed from a Nitinol hypodermic tube having at least one space 1160 formed therein, thereby defining at least one support arm 1025 thereon.

Each of the support arms 1025 includes at least one electrode 1030 and at least one corresponding electrode cable 1125 thereon. The electrodes 1030 may comprise individual electrodes (i.e., independent contacts), a segmented electrode with commonly connected contacts, or a single continuous electrode. The electrode cable 1125 extends proximally from the electrode 1030. The electrode 1030 may comprise a raised component or a flat component on the support arm 1025. The electrode 1030 and/or the electrode cable 1125 may be coupled to the support arm 1025 using any of a variety of known connection methods, including by way of non-limiting example, welding, adhesive, and/or mechanical fasteners. For example, in one embodiment, the electrode 1030 may be adhesively bonded to the support arm 1025 using Loctite 3311 or any other biologically compatible adhesive. In some embodiments, the electrode 1030 may be integrally formed with the support arm 1025. Furthermore, all of a portion of the electrode may be coated or plated with gold, or a material having like properties, such as, by way of non-limiting example, silver or an alloy of copper, to improve radiopacity and/or conductivity without adversely diminishing the flexibility of the expandable structure 1000.

At least one electrode 1030 is positioned on the medial section 1105 of the support arm 1025, thereby permitting the electrode 1030 to be positioned proximate to or in contact with a vessel luminal wall when the expandable structure is deployed and in an expanded condition. Any remaining electrodes 1030 may be located at any position along the length of the support arm 1025. The expandable structure 1000 may include support arms 1025 including any variation or pattern of electrode distribution among the individual support arms. Depending upon the desired application of the thermal basket catheter 850, the expandable structure 1000 may have an identically configured pattern of electrodes 1030 on the support arms 1025, or a varying pattern of electrodes 1030 on the support arms 1025. For example, in the pictured embodiment, the electrodes 1030a, 1030b, and 1030c are positioned on the medial section 1105, while the electrode 1030d is positioned on the distal section 1110 of the support arm 1025.

Each electrode 1030 is electrically coupled to the ablation source 225, which is disposed external to the patient, for the delivery of a thermal electric field for the heating of target neural fibers. In the pictured embodiment, each electrode 1030 is connected to the corresponding electrode cable 1125, which traverses the length of the support arm 1025 from the electrode 1030 to the interface 940 and/or the thermal electric field generator 325. In some embodiments, the electrode cable 1125 may be selectively insulated such that only a selective portion of the electrode cable, e.g., a distal tip of the cable, may be electrically active. In alternate embodiments, several electrodes may be coupled to the field generator using one or more shared electrode cables. In other embodiments, the electrodes may communicate with the ablation source 225 via wireless means.

Each of the support arms 1025 includes at least one sensor 1035 and at least one corresponding sensor cable 1170 thereon. The sensor 1035 may comprise a raised component or a flat component on the support arm 1025. The sensor cable 1170 extends proximally from the sensor 1035. The sensor 1035 and/or the sensor cable 1170 may be coupled to the support arm 1025 using any of a variety of known connection methods, including by way of non-limiting example, welding, adhesive, and/or mechanical fasteners. For example, in one embodiment, the sensor 1035 may be adhesively bonded to the support arm 1025 using Loctite 3311 or any other biologically compatible adhesive. In some embodiments, the sensor 1035 may be integrally formed with the support arm 1025. For example, in some embodiments, at least one sensor 1035 may be comprised of flexible circuits integrated into at least one support arm 1025. The flexible circuit may be comprised of polymer thick film flex circuit that incorporates a specially formulated conductive or resistive ink that is screen printed onto the flexible substrate to create the thermal sensor circuit patterns. This substrate is then adhered to the surface of each of the support arms 1025. In an alternate embodiment, the substrate can be adhered to independently expandable, resilient body arms which are not part of an expandable structure 1000. The independent sensor body can be provided with the appropriate number of body arms, such as four, five, six, or more.

At least one sensor cable connects each sensor 1035 to the sensor coupler and/or the interface 940. In alternate embodiments, several sensors may be coupled to the sensor coupler and/or the interface 940 using one or more shared sensor cables, as illustrated by sensors 1035c and 1035f. In other embodiments, the sensors 1035 may communicate with the sensor coupler, interface 940, and/or processor 220 via wireless means. The at least one sensor cable 1170 may traverse the elongated body 920 through the sleeve lumen 1060, the internal passage 1070 (as illustrated in FIG. 22), or both. In some embodiments, a single cable may convey thermal energy to the electrode 1030 and convey data from the sensor 1035.

Exemplary sensors 1035 include, without limitation, ultrasonic sensors, flow sensors, thermal sensors, such as thermocouples, thermistors and infrared sensors, pressure sensors, electrical contact sensors, conductivity and/or impedance sensors, electromagnetic detectors, fluid flow sensors, electrical current sensors, tension sensors, chemical or hormonal sensors (capable of detecting the concentration or presence/absence of various gases, ions, enzymes, proteins, metabolic products, etc.), and pH sensors. For example, the sensor 1035 may comprise a thermocouple or other type of temperature sensor for monitoring the temperature of the target tissue, the non-target tissue, the surrounding blood, the electrodes 1030, or any other part of the expandable structure 1000. In one embodiment, the thermocouple may be capable of detecting thermal discontinuities or variations in vessel wall temperature, thereby providing a thermal basket catheter capable of locating inflamed or vulnerable plaques on the luminal wall of a blood vessel in vivo. The expandable structure 1000 may contain any of a variety of sensor types within a single embodiment. As a result, the catheter 850 may be capable of simultaneously examining a number of different characteristics of the target tissue, the surrounding environment, and/or the catheter 850 itself within the body of a patient, including, for example, vessel wall temperature, blood temperature, electrode temperature, fluorescence, luminescence, flow rate, and flow pressure.

The at least one sensor 1035 may be located at any position along the length of the support arm 1025. In some embodiments, the at least one sensor 1035 may be located proximate to the electrode 1030 on the support arm 1025, as illustrated by sensors 1035a and 1035c. In the same or alternate embodiments, at least one sensor 1035 may be positioned within or surrounding the electrode 1030, as illustrated by sensor 1035b. As shown in FIG. 27 by sensors 1035a and 1035c, the sensor 1035 may be positioned on or near the apex of the curved support arms 1025 when the expandable structure 1000 is deployed in an expanded state, thereby permitting the sensors to contact a vessel luminal wall. In some embodiments, the sensor 1035a, 1035b, and/or 1035c may comprise a pressure sensor(s) that may detect the pressure with which the proximate electrode 1030 is contacting the vessel wall, thereby allowing the user to determine whether the electrode 1030 is effectively contacting the vessel wall to ensure adequate energy transfer and neuromodulation/ablation. In some embodiments, as illustrated by sensors 1035d and 1035f, the at least one sensor 1035 may be positioned on the support arms 1025 at any radial distance less than the radial distance of the apex of the curved support arms 1025 relative the longitudinal axis CA when the expandable structure 1000 is in a deployed state, thereby preventing the at least one sensor from contacting a vessel luminal wall when the expandable structure 1000 is deployed to an expanded state.

Depending upon the desired application of the thermal basket catheter 850, the expandable structure 1000 may have an identically configured pattern of electrodes 1030 and sensors 1035 on the support arms 1025, or a varying pattern of electrodes 1030 and sensors 1035 on the support arms 1025. For example, in the pictured embodiment, the sensors 1035a, 1035b, and 1035c are positioned on the medial section 1105, while the sensor 1035d is positioned on the proximal section 1100 of the support arm 1025.

In some embodiments, radiopaque markers 600 may be positioned along the length of the support arms 1025, aiding in the placement and visualization of the thermal basket catheter 850. In some embodiments, as shown in FIG. 28, individual support arms 1025 may carry a distinctive pattern or shape of radiopaque markers 1180 to enable the user to distinguish individual support arms in the image data gathered from the imaging apparatus 980 and/or external imaging. For example, the support arm 1025a carries two distinctively shaped radiopaque markers 1180a while the support arm 1025b carries a distinctively shaped radiopaque marker 1180b. In other embodiments, alternatively or additionally, the electrodes 1030 and/or the sensors 1035 are radiopaque or coupled to radiopaque markers (not shown).

The electrodes 1030 may be configured to provide differential or selective heating of the vessel luminal wall, wherein individual electrodes may be selectively activated to convey thermal energy to the vessel luminal wall while other electrodes on the same or different support arm 1025 are not activated and do not provide thermal energy. In addition, individual electrodes 1030 may be configured to convey different amounts of thermal energy to different parts of the vessel luminal wall. Furthermore, the electrodes 1030 may be configured to provide a bipolar signal, or the electrodes may be used together or individually in conjunction with the separate patient ground pad or electrode 350. As illustrated in FIG. 27, the electrodes 1030 are distributed circumferentially about the axis CA in an array, with adjacent electrodes being slightly axially offset, preferably being staggered or alternating between more proximal and more distal positions on the medial section 1105. This arrangement allows bipolar energy to be directed between adjacent circumferential electrodes, between adjacent "distal" electrodes, between adjacent "proximal" electrodes, and the like.

FIGS. 29*a* and 29*b* provide a schematic flowchart illustrating methods of delivering and controlling the thermal neuromodulation to renal vessels. With reference to FIGS. 16, 29*a*, and 30, step 1210 comprises the user initiating a thermal neuromodulation procedure by positioning the thermal basket catheter 850 within the renal artery 854. Prior to insertion of the catheter 850, the guidewire 1050 (as illustrated in FIG. 21) may be introduced into the arterial vasculature of a patient using standard percutaneous techniques. Once the guidewire 1050 is positioned within the target blood vessel, which is the left renal artery 854 in the illustrated embodiment, the catheter 850 may be introduced into the arterial vasculature of a patient over the guidewire 1050 and advanced to the area of interest. In the alternative, the catheter 850 may be coupled to the guidewire 1050 external to the patient and both the guidewire 1050 and the catheter 850 may be introduced into the patient and advanced to an area of interest simultaneously. The catheter 850 may include IVUS or other imaging apparatuses 980 (as shown in FIG. 30) thereon, thereby permitting the user to precisely position the catheter 850 within the blood vessel by using in vivo, real-time intravascular imaging. Additionally or alternatively, the user may utilize external imaging, such as, by way of non-limiting example, fluoroscopy, ultrasound, CT, or Mill, to aid in the guidance and positioning of the catheter 850 within the patient's vasculature. The external and intravascular images may be co-registered to each other for side-by-side or composite display of the images.

The catheter 850 is positioned within the renal anatomy such that the expandable structure 1000, which is disposed in an unexpanded condition within the outer sleeve 1055 (as shown in FIG. 23) when introduced the patient's vasculature, is positioned proximal to the target area of interest, including, by way of non-limiting example, renal artery 854, the inferior renal vessels 864, and/or the abdominal aorta 856. Prior to expanding the expandable structure 1000, at step 1212, the user may utilize the imaging apparatus 980 and/or the central imaging apparatus 1001 to obtain intravascular images of the target area and area immediately surrounding the target area. The imaging apparatus 980 and/or the central imaging apparatus 1001 may obtain images of the vessel wall concentrically about the catheter 850 so as to measure the thickness of the vessel wall in the target area of interest. In some cases, the imaging data may allow identification and/or tissue characterization of the atherosclerotic changes, plaques, tissues, lesions, and the like from within the blood vessel.

At step 1213, the imaging data is transferred to the characterization application 250, which then characterizes the tissue composition and ablation level of the imaged tissue. The imaging and/or characterization data may lead to a determination of the optimal intravascular location for the application of thermal neuromodulation.

At step 1214 of FIG. 29*a*, the processor 220 and/or the user may analyze the intravascular images obtained by the imaging apparatus 980 and/or the central imaging apparatus 1001 and the tissue characterization data from the characterization application 250 to determine whether the renal artery 854 possesses atherosclerotic changes or other disease processes of the vessel wall in the target area of interest. In some instances, the processor 220 and/or the user may analyze both the intravascular images and the tissue characterization to determine various tissue features. As illustrated in FIG. 18*c*, distance D3 exists between the luminal wall 884" and the renal nerves 870 in the area of an atherosclerotic plaque that is greater than the distance D2 that exists between a healthy vessel wall 884 and the renal nerves 870 pictured in FIG. 18*a*.

At step 1216, if the user and/or the processor 220 determines that the vessel area immediately surrounding the expandable structure 1000 is not the optimal site for thermal neuromodulation within the vessel based on the positional imaging data based on the imaged intraluminal vessel contours, wall thicknesses, and plaque types (as shown in FIG. 17), the user and/or the processor 220 may return to step 1210 and reposition the catheter 850 into a portion of the artery 854 containing less plaque or having a thinner wall.

For example, if the intravascular imaging suggests the presence of eccentric atherosclerotic plaques or thickening along the length of the renal artery 854, as shown by portion 876 in FIGS. 17 and 18*c*, the processor 220 and/or the user may reposition the catheter 850 in an optimal area having the thinnest intra-to-extravascular distance across the vessel wall (as shown by portion 874 in FIGS. 17 and 18*a*). For example, as described above in reference to FIGS. 6 and 12-14, the intravascular imaging and/or the tissue characterization may reveal the presence of calcified changes in the vessel wall, which can hinder the transfer of energy through the vessel wall to the target nerves. Ultimately, the user and/or the processor 220 may direct more thermal energy to the electrodes 1030 positioned adjacent the thicker and/or more calcified portions of the plaque than those positioned against thinner portions of the plaque or the healthier portions of the vessel wall, thereby enabling the appropriate amount of thermal energy to reach the target renal nerves.

Once the user and/or the processor 220 have determined at step 1218 that the catheter 850 is positioned in the optimal location for neuromodulation within the vessel, at step 1220, the processor 220 and/or the user may record or store (e.g., in the memory 245) the imaging and/or tissue characterization data associated with the particular intravascular position of the catheter 850 within the renal artery 854 or the abdominal aorta 90 relative to the renal ostia 92. At step 1222, the user may use this positional data about the intraluminal characteristics of the optimal vessel site, including, by way of non-limiting example, the intra-extravascular or intra-extraluminal distance, the wall thickness, and/or the type of atherosclerotic plaque, to plan the current treatment procedure and/or repeat treatment procedures for the same intravascular site. Throughout the neuromodulation procedure, the user and/or the processor 220 may store imaged, characterized, and/or sensed data (e.g., in the memory 245).

At step 1224 of FIG. 29*a*, after assessing the intravascular target area of interest and positioning the catheter 850 in the optimal location, the user operates the elongated body actuator 1010 positioned within the actuator recess 1011 on the handle 930 to expand the catheter 850 and deploy the expandable structure 1000. The rearward operation of the elongated body actuator 1010 may result in the outer sleeve 1055 retracting rearwardly, thereby exposing the expandable structure 1000 and permitting the expandable structure 1000 to assume a relaxed, expanded state wherein the one or more support arms 1025 flare outwardly, as shown in FIG. 26. The positioning of the expandable structure 1000, the support arms 1025, the electrodes 1030, and the sensors 1035 may be facilitated by the imaging apparatus 980 and/or the central imaging apparatus 355, and/or external imaging utilizing the radiopaque markers 970.

FIG. 30 shows the expandable structure 1000 positioned and deployed in an expanded condition within a curved atherosclerotic portion 1300 of the renal artery 854 (similar to the portion 876 shown in FIG. 17) according to one embodiment of the present disclosure. The support arms 1025 have expanded outwardly from the longitudinal axis CA, thereby permitting the electrodes 1030 and sensors 1035 located on the support arms 1025 to contact the internal luminal surface 1310 of the vessel 1300. The luminal surfaces 1310a, 1310b correspond to raised, irregular inner surfaces of the vessel 1300 that have been deformed by a circumferential atherosclerotic plaque 1320. The luminal surface 1310a covers the thinnest portion of the plaque 1320, unlike the luminal surface 1310b, which covers a thicker portion of the plaque 1320. As shown, the expandable structure 1000 has been positioned adjacent to the luminal surface 1310a, which is an optimal intravascular position for thermal neuromodulation because of a relatively small intra-to-extravascular distance D6.

An apex of the medial section 1105a of first support arm 1025a is extended a first distance D4 from the guidewire lumen 1075 while permitting an electrode 1030a and a sensor 1035a positioned thereon to remain in contact with the vessel wall 1310a. A first distal tip 1330a of the support arm 1025a is positioned adjacent to or proximate to the first support arm retainer 1115a within the retainer sleeve 1120. A second support arm 1025b has an apex that is positioned a second distance D5 from the guidewire lumen 1075 while permitting an electrode 1030a and a sensor 1035b positioned thereon to remain in contact with the vessel wall 1310b, wherein the second distance D5 is smaller than the first distance D4. The second distal tip 1330b of the second support arm 1025b is positioned distally from the retainer 1115b within the retainer sleeve 1120. As a result, the electrodes 1030a, 1030b and the sensors 1035a, 1035b positioned on each of the support arms 1025a, 1025b remain in contact with the vessel wall 1310 despite the disparity between distances D4 and D5.

Thus, as a result of the expandable structure 1000 expanding radially outwards, the at least one electrode 1030 located on the at least one support arm 1025 radially engages the luminal wall 1310. Wall-contacting electrodes facilitate more efficient transfer of thermal energy across the vessel wall 1310 to the target nerve fibers 870 than electrodes positioned away from the wall 1310.

With reference to FIG. 29a, at step 1226, to aid in registering the electrodes 1030 (i.e., the ablative elements) with the circumferential luminal wall 1310 of the vessel 1300, the user and/or the processor 220 may perform intravascular imaging or external imaging of the distinctively shaped radiopaque markers, such as 1180b, of various support arms 1025. In some instances, at step 1227, the user and/or the processor 220 may again use the tissue characterization application 250 to characterize the tissue composition and ablation level of the target tissues.

At step 1228, the user and/or the processor 220 may utilize such imaging and/or characterization data to determine the circumferential placement of particular electrodes 1030 and to refine the treatment plan. For example, in some embodiments, the IVUS image may be brighter from an ablated region or a region with a more fibrous/necrotic core. Utilizing the real-time intravascular image data provided by the imaging apparatus 980 and/or the central imaging apparatus 355, as well as the real-time tissue characterization data, the user and/or the processor 220 may plan to apply uniform heating of all the electrodes 1030 or differential heating by selectively activating or energizing an individual electrode 1030 or a selective subset of electrodes 1030 with varying amounts of thermal energy, e.g., RF energy, to apply the optimal amount and type of thermal energy to the renal nerves 870 surrounding the vessel 1300 to properly ablate and/or denervate the target area. The tissue characterization data allows the user and/or processor 220 to determine the appropriate level of ablative energy necessary to ablate the various tissue components of the target object. The user and/or processor 220 may utilize the tissue characterization data to tune the thermal basket catheter 850 (i.e., the ablation catheter) to apply only the appropriate amount or intensity of ablative energy through the electrode(s) 1030 (i.e., the ablative element(s) 170). Throughout the thermal neuromodulation procedure, updated tissue characterization data about ablation level may be utilized as a reference against which changes in ablation level may be compared upon application of thermal energy to the target site.

In some embodiments, at step 1230, before initializing the application of ablative energy, the user and/or the processor 220 may utilize the electrodes 1030, the sensors 1035, and/or any auxiliary sensors to sense baseline measurements of various cardiovascular and neurological characteristics of the vessel, including by way of non-limiting example, vessel wall temperature, vessel lumen temperature, the temperature of surrounding non-target tissue, vessel wall impedance and/or conductivity at the target site (i.e., at points of electrode contact with the vessel wall). For example, by emitting a low voltage pulse from the electrodes 1030 through the vessel wall and measuring the electrical response, a baseline impedance for the vessel wall at a particular position may be established.

At step 1232 of FIG. 29a, the user and/or the processor 220 may utilize such baseline data to refine the treatment plan. For example, utilizing this baseline data, the user and/or the processor 220 may plan to apply uniform heating of all the electrodes 1030 or differential heating by selectively activating or energizing an individual electrode 1030 or a selective subset of electrodes 1030 with varying amounts of thermal energy to apply the optimal amount and type of thermal energy to the renal nerves 870 surrounding the vessel 1300 to properly denervate the target area. Throughout the thermal neuromodulation procedure, the baseline measurements may be utilized as a reference against which changes in impedance or conductivity may be compared upon application of thermal energy to the target vessel site.

At step 1234 of FIG. 29b, the user and/or the processor 220 may initiate the actual thermal neuromodulation (i.e., ablative) process by applying thermal (i.e., RF) energy to the renal nerves 870 through the electrodes 1030. Initially, in the pictured embodiment, the ablation source 225 generates a thermal electric field, which is selectively transferred to an individual electrode 1030 or a selective subset of electrodes 1030 on the expandable structure 1000. A bipolar electric field may be generated between electrodes 1030 positioned on the expandable structure 1000, or a monopolar electric field may be delivered between the electrode 1030 and the neutral electrode or ground pad. This thermal energy is transferred from the activated electrodes 1030 to the nerves 870 across the vessel wall 1310. The electric field thermally modulates the electrical activity along the nerve fibers 870 that control the sympathetic activity of the kidney through the application of heat. This thermal neuromodulation may ablate the nerves 870 or produce non-ablative injury in the nerves 870.

Desired neuromodulative effects may include raising the temperature of target nerves 870 over a certain threshold to achieve non-ablative neuromodulation, and raising the temperature of target nerves 870 over an even higher threshold to achieve non-ablative neuromodulation. For example, in some instances, desired neuromodulative effects may occur as a result of raising the temperature of the target nerves to a temperature ranging from about 42 to about 48 degrees Celsius. In most instances, the temperature of the target nerves should not be raised above 62 degrees Celsius to avoid breakdown of the surrounding tissue. These temperature ranges and thresholds are provided for illustrative purposes only, and are not intended to be limiting.

Additionally or alternatively, desired neuromodulative effects may include lowering the temperature of target nerves 870 under a certain threshold to achieve non-ablative neuromodulation, and lowering the temperature of target nerves 870 over an even lower threshold to achieve non-ablative neuromodulation. The electric field may also induce electroporation in the nerve fibers 870.

The non-target tissues surrounding the expandable structure 1000 may be protected by focusing the delivery of thermal energy on the target neural fibers 870 such that the intensity of thermal energy affecting the non-target tissues is insufficient to induce serious damage to the non-target tissues. Nevertheless, the surrounding non-target tissues of the vessel wall 1310 may also become heated and experience an increase in temperature during delivery of the thermal energy which may damage certain non-target tissues. During the neuromodulation process, the blood flowing through the spaces 1160 and passage 1150 of the expandable structure may act as a heat sink enabling the conductive and/or convective transfer of heat from the non-target tissue to the blood, thereby protecting the non-target tissue. With blood flowing through the vessel and across the electrodes, more thermal energy may be carried away from the non-target tissues, thereby enabling the use of longer and higher energy neuromodulation treatments. Therefore, the open, basket-like configuration of the expandable structure 1000 enables the application of higher energy and longer thermal neuromodulation treatments than would a device that blocked or impeded blood flow.

The user and/or the processor 220 directs the application of thermal energy to target nerves at a specific location for a desired amount of time. In some instances, the desired amount of time may be predetermined by the baseline calculations and/or the patient's underlying vascular pathology, depending upon the condition of the patient's vascular tissue and surrounding tissues. In other instances, the duration of the application of thermal energy to a specific target may vary depending upon imaging results and tissue characterizations obtained during the procedure. In some instances, a desired neuromodulative effect is attained after application of thermal energy to a target location for about 30 seconds to about 2 minutes. This exemplary duration is provided for illustrative purposes only and is not intended to be limiting.

After applying thermal energy at one target location in the vessel, the user and/or processor may reposition the expandable structure 1000 within the lumen and apply thermal energy at another location along the vessel. In some instances, the user and/or processor may reposition the expandable structure 1000 by rotating the catheter 850 and/or the expandable structure 1000. In some instances, the user and/or processor may reposition the expandable structure 1000 by moving the catheter 850 and/or the expandable structure 1000 linearly (i.e., proximally or distally) through the lumen of the vessel. The linear distance between two adjacent areas of application may be predetermined by the baseline calculations, the initial tissue characterizations, and/or the patient's underlying vascular pathology, depending upon the condition of the patient's vascular tissue and surrounding tissues. In other instances, the linear distance between two adjacent areas of application may vary depending upon imaging results and real-time tissue characterizations obtained during the procedure. For example, in some instances, the linear distance between two adjacent areas of application may range from about 1 to 3 mm. In one instance, the linear distance between two adjacent areas of application may be 2 mm. These distances are provided for illustrative purposes only, and are not intended to be limiting.

In some embodiments, the user and/or the processor 220 may direct the application of thermal energy to the plaque to ablate or remodel the plaque and/or reduce the plaque thickness prior to the thermal neuromodulation procedure. Such treatment may be tailored to short term and/or long term increases in lumen diameter and blood flow through the vessel of interest. In some embodiments, remodeling of the atherosclerotic plaque may comprise the use of higher energies to ablate and remove occlusive material from within vessel lumens, and particularly to remove atherosclerotic material from the blood vessel in order to improve blood flow. As described above in relation to FIGS. 6, 12-14, and 29a, the user and/or processor 220 may use real-time tissue characterization data to determine the appropriate level of ablative energy to apply to particular tissue components and adjust the amount of ablative energy applied through the electrode(s) 1030 accordingly.

At step 1236, as shown in FIGS. 29b and 30, as a result of the expandable structure 1000 expanding radially outwards, the at least one sensor 1035 located on the at least one support arm 1025 radially contacts the luminal wall 710, thereby enabling the measurement of the vessel wall temperature. Simultaneously, if provided, the ancillary sensor 1040 located proximate to the expandable structure 1000 on an exterior surface of the guidewire lumen 1075 may measure a characteristic of the environment surrounding the target area, e.g., the blood temperature within the blood vessel, without contacting the vessel wall 1310. Both the sensor 1035 and the ancillary sensor 1040 may send the collected data to the sensor coupler and/or the interface 940 via at least one sensor cable 1170, after which the data is transmitted to the controller 210 and the processor 220.

In some embodiments, the imaging apparatus 980 and/or central imaging apparatus 1001 continue to obtain intravascular image data and tissue characterization data during the application of thermal energy to the vessel wall 1310 to monitor and/or guide the progress of the renal neuromodulation. In some embodiments, the image and tissue characterization data provides evidence of damage to the vessel wall 1310, neural injury, and/or levels of neural ablation. At step 1238, the user and/or processor 220 may direct the imaging apparatus 980 and/or central imaging apparatus 355 obtain intravascular image data of the vessel wall adjacent the target nerves during and/or after the application of thermal energy to the vessel wall 1310. At step 1240, the characterization application 250 can analyze the intravascular image data of the vessel wall adjacent the target nerves during and/or after the application of thermal energy to the vessel wall 1310 to characterize different tissue components and the level of ablation achieved.

At step 1242, the user and/or the processor 220 may utilize such data (including, for example, the sensing, imaging, and/or tissue characterization data) to determine whether the desired level of thermal injury has been achieved. At step 1244, if the imaging data leads to an assessment that the desired level of thermal injury and/or neuromodulation has been achieved, the user and/or the processor 220 may stop the application of thermal energy at step 1246. If, at step 1248, user and/or the processor 220 use the imaging data to determine that the desired level of thermal injury and/or neuromodulation has not been achieved, the user and/or the processor 220 may continue the application of thermal energy and/or refine the treatment plan based on the acquired data at step 1250.

In particular, at step 1250, the user and/or the processor 220 may control or modulate the thermal neuromodulation by using the measured parameters from step 1236 as feedback. For example, in some embodiments, at least one sensor 1035 may be configured as a temperature sensor able to measure the temperature of the vessel wall and/or the non-target tissue. If the sensed temperature falls above a therapeutic range indicating a safe range for thermal neuromodulation or the sensed temperature reaches a temperature indicating the desired level of renal nerve injury or ablation, the ablation system 100 may be configured to alert the user and/or the processor to stop the application of thermal energy at step 1246. For example, in some instances, desired neuromodulative effects may occur as a result of raising the temperature of the target nerves to a temperature ranging from about 42 to about 48 degrees Celsius. For example, in some embodiments, the sensed vessel wall temperature should not exceed approximately 62 degrees Celsius. These temperature thresholds are provided for illustrative purposes only, and are not intended to be limiting.

At step 1242, if the sensed temperature falls within the therapeutic range indicating a safe range for thermal neuromodulation or the sensed temperature has not yet reached a temperature indicating the desired level of renal nerve injury or ablation, the system 100 may be configured to alert the user and/or the processor to continue the application of thermal energy and/or refine the treatment plan at step 1250. The potential for undesirably injuring the non-target tissue may be weighed against the expected benefits of thermally neuromodulating the target tissue.

In alternate embodiments, at least one sensor 1035 may be configured as an impedance or conductance sensor, obtaining data about the impedance of the vessel wall 1310 at any given point. Such sensors may measure the impedance of alternating current (AC) circuits between the electrode 1030 and the vessel wall 1310, and may include a measurement of both a real portion or magnitude of the impedance, and an imaginary portion or phase angle of the impedance. The impedance magnitude and phase angle generated at an appropriate frequency by the portion of the vessel wall 710 coupled to the electrode may provide a tissue signature. To enhance the accuracy of tissue signature measurements, a plurality of individual measurements may be taken and averaged. By measuring tissue signatures at a plurality of different frequencies within a frequency range, a signature profile for the portion of the vessel wall 1310 may be generated. In some embodiments, the various tissue signature measurements about a circumferential portion of the vessel wall 1310 may be compared to distinguish between healthy tissue, calcified plaque, fibrous plaque, lipid-rich plaques, untreated tissue, partially treated tissue, fully treated tissue, and the like. The user and/or the processor 220 may use the tissue profiles to determine where in the vessel wall 1310 the patient requires more neuromodulation and/or the effectiveness of the applied neuromodulation treatment.

In alternate embodiments, at least one sensor 1035 may be configured as a sensor of nerve conductivity/traffic/activity, obtaining data about the neurological activity of the renal nerves 870 overlying the vessel wall at any given point before, during, and/or after the neuromodulation procedure. Such sensors may measure the neurological activity of the renal nerves 870 overlying the vessel wall 710, and may include a measurement of afferent and/or efferent conductivity. In some embodiments, the various neurological conductivity measurements about a circumferential portion of the vessel wall 1310 may be compared to distinguish healthy neural tissue from damaged or ablated neural tissue. The user and/or the processor 220 may use the sensed data about neural conductivity/activity/traffic to determine where neural plexus overlying in the vessel wall 1310 the patient requires more neuromodulation and/or the effectiveness of the applied neuromodulation treatment. In some embodiments (not pictured in FIG. 29*b*), the user and/or the processor 220 may use the sensed data about neural conductivity/activity/traffic to determine whether the patient requires more neuromodulation after the other sensed data and/or imaging data suggest that the thermal neuromodulation procedure is complete.

In some embodiments, at least one sensor 1035 may be configured as a chemical or hormonal sensor, obtaining data about the sympathetic activity of the patient within the vessel 1300. For example, the sensor 1035*a* may monitor a norepinephrine level with the patient's blood, e.g., within the renal vessel 1300. Elevated norepinephrine levels may indicate elevated sympathetic activity. If the norepinephrine level rises above a certain threshold, the sensor 1035*a* may monitor renal blood flow and/or renal blood pressure within the renal artery 1300. Because sympathetic efferent activation causes renal vasoconstriction and a reduction in renal blood flow, blood flow and/or blood pressure in the renal vessel 1300 may indicate the level of renal sympathetic activity. If blood flow to kidneys is decreased and/or renal blood pressure is increased, the sensor 1035*a* may identify an increase in sympathetic activity and send data reflecting this information to the user (via the controller 210) and the processor 220. Once the blood flow and/or blood pressure return to normal, the sensor 1035*a* may switch back to monitoring norepinephrine levels. In alternate embodiments, the expandable structure 1000 utilizes a plurality of sensors, e.g., 1035*a* and 1035*b*, to obtain data reflective of changes in renal sympathetic activity.

The user and/or the processor 220 may identify changes in the sympathetic activity level of a patient based on one or more sensed physiological parameters, such as, by way of non-limiting example, blood pressure, blood flow, and/or norepinephrine levels, and control thermal energy delivery to the renal nerves 870 in response to the identified changes. The user and/or the processor 220 may use the sensed physiological parameters to determine when the patient requires more neuromodulation and/or the minimum level of neuromodulation required to maintain renal sympathetic activity below a desired level.

Similarly, the imaging apparatus 980 can continuously or periodically obtain image data about the vessel wall 1310 and/or a target object associated with the vessel 1300 at any given point. In some embodiments, the field of view of the imaging apparatus 980 overlaps the ablative field of the electrode 1030 such that the user and/or processor 220 can observe and image the ablation/neuromodulation in real time. Moreover, the image data obtained can be used by the characterization application 250 to output tissue characterization and the observed level of ablation in real time. To enhance the accuracy of tissue characterizations and ablation assessments, a plurality of individual characterizations and ablation assessment scores for neighboring scan lines from the image data may be taken and averaged. In some embodiments, the various tissue characterizations and ablation assessments about a circumferential portion of the vessel wall 1310 may be compared to distinguish between healthy tissue, calcified plaque, fibrous plaque, lipid-rich plaques, untreated tissue, partially treated tissue, fully treated tissue, and the like. The user and/or the processor 220 may use these tissue profiles to determine where in the vessel wall 1310 the patient requires more neuromodulation and/or the effectiveness of the applied neuromodulation treatment.

In some embodiments, as shown by steps 1234-1250 in FIG. 29b, the electrodes 1030 cooperate with the processor 220, the imaging apparatus 980, the characterization application 250, and the sensors 1035, 1040 to create a closed feedback loop wherein the processor 220 continuously or intermittently refines the treatment plan and application of thermal energy by directing an individual electrode or a particular combination of electrodes to deliver a particular type, magnitude, and duration of thermal energy depending upon the data received from the sensors 1035, 1040, the imaging apparatus 980, and the characterization application 250. Alternatively or additionally, the user may refines the treatment plan and application of thermal energy by directing an individual electrode or a particular combination of electrodes to deliver a particular type, magnitude, and duration of thermal energy with or without depending upon the data received from the sensors 1035, 575.

Steps 1234-1250 of FIG. 29b illustrate how the thermal neuromodulation process may be monitored and controlled by acquiring data from the imaging apparatus, the characterization application, and/or the sensors along the vessel wall 1310 in the region of treatment, and limiting the power and/or duration of the application of thermal energy to the vessel wall 1310 in response to that data. For example, in response to the data collected by the imaging devices, the characterization application, and the sensors, the user or program algorithms from the processor 220 may selectively direct individual electrodes 1030 or combinations of electrodes 1030 to apply thermal energy to the vessel wall 1310 while other electrodes remain inactive. In addition, the user or program algorithms from the processor 220 may selectively direct individual sensors 1035, 1040 or combinations of particular sensors 1035, 1040 to obtain measurements while other sensors remain inactive.

In the course of the neuromodulation process and data collection, the distal portion 960 of the body 920 may be retracted proximally or advanced distally within the vessel 1300, while the expandable structure 1000 is in an expanded condition, in order to determine a gradient of measurements and/or tissue characterizations over a longitudinal length of the vessel. For example, the user may advance and/or retract the expandable structure 1000 in 2 millimeter increments to apply thermal energy at various positions within a target vessel. Alternatively, the expandable structure 1000 may be repeatedly contracted or unexpanded, and the catheter 850 may be axially moved to reposition the expandable structure 1000, with subsequent expansion of the expandable structure 1000 at each of a plurality of treatment locations along the vessel 1300.

At step 1246, after determining that the neuromodulation process is complete based on the intravascular image data, the sensed data, and/or the tissue characterization data, the user may stop the application of thermal energy and, at step 1252, begin the process of removing the thermal basket catheter 850 from the target vessel and the patient's body. Initially, the user may return the elongated body actuator 1010 located on the handle 930 to a non-deployed position within the actuator recess 1011 (shown in FIG. 19). As a result, the outer sleeve 1055 may be advanced towards the distal portion 960, as shown in FIGS. 22 and 24, thereby allowing the body 920 to assume an unexpanded condition. While advancing towards the distal portion 960, an inner wall of the outer sleeve 1055 engages and compresses the expandable structure 1000 inwardly, thereby permitting the expandable structure 1000 to be received within the sleeve lumen 1060 and returning the expandable structure 1000 to a non-deployed, unexpanded configuration, as illustrated in FIG. 23. Prior to removing the catheter 850 from the blood vessel 1300, the user may delivery a therapeutic agent to an area of interest with the catheter 1300 through the guidewire port 1045, for example. Thereafter, the catheter 850 and the guidewire 1050 may be removed from the patient and the entry incisions may be closed.

The devices, systems, and methods described herein may be used to characterize tissue and provide real-time feedback as to the level of ablation during a variety of ablation and/or neuromodulation applications, including without limitation: carotid body ablation, cardiac ablation (including myocardial and valvular ablation, e.g., the mitral or atrial valves), renal neuromodulation intravascular lesion ablation, and chronic total occlusion ablation. In each of these embodiments, the database or memory 245 would be configured to contain pre-determined tissue imaging properties 480 and secondary parameters 490 associated with particular types of tissue at varying levels of ablation. The imaging apparatus 180 utilizes this database 245 to compare and correlate the signal properties of the tissue-of-interest with the pre-determined properties 480 to accurately characterize the tissue and determine the real-time level of ablation.

The systems and methods described herein provide automated, reliable, and reproducible tissue and ablation level characterization using a combination ablation and imaging probe and a database containing pre-determined tissue properties for various types and ablation levels of tissue components, thus reducing the need for highly trained, highly experienced observers and generally eliminating observer bias (as well as intra- and inter-observer variability). In addition, the systems and methods described herein may allow for an evaluation of the ablation therapy from the tissue characterization in real-time, thereby reducing the need for tissue biopsies and the time necessary to receive a diagnosis from the biopsy results. Even in instances where a biopsy is still indicated after tissue characterization by the systems and methods disclosed herein, the systems and methods described above may be utilized to provide detailed image guidance for biopsies (i.e., directing the user to a particular tissue type, tissue margin, or ablated area for biopsy). Moreover, the systems and methods disclosed herein offer the ability to analyze multiple parameters, such as, by way of non-limiting example, a patient's pre-existing medical condition, the sensed characteristics of the target object (e.g., temperature and impedance), the imaging data from multiple imaging modalities, the tissue characterization, and the determination of ablation level to optimize real-time evaluation and monitoring of an ablative procedure.

While the present invention has been illustrated by the description of embodiments thereof, and while the embodiments have been described in considerable detail, it is not the intention of the applicants to restrict or in any way limit the scope of the appended claims to such detail. Additional advantages and modifications will readily appear to those skilled in the art. Therefore, the invention, in its broader aspects, is not limited to the specific details, the representative apparatus, and illustrative examples shown and described. Accordingly, departures may be made from such details without departing from the spirit or scope of the applicant's general inventive concept.

The following includes definitions of selected terms used throughout the disclosure. Both singular and plural forms of all terms fall within each meaning.

"Computer-readable medium," as used herein, refers to any medium that participates in directly or indirectly providing signals, instructions and/or data to one or more processors for execution. Such a medium may take many forms, including but not limited to, non-volatile media, volatile media, and transmission media. Non-volatile media may include, for example, optical or magnetic disks. Volatile media may include dynamic memory. Transmission media may include coaxial cables, copper wire, and fiber optic cables. Transmission media can also take the form of acoustic or light waves, such as those generated during radio-wave and infra-red data communications, or take the form of one or more groups of signals. Common forms of computer-readable media include, for example, a floppy disk, a flexible disk, hard disk, magnetic tape, or any other magnetic medium, a CD-ROM, any other optical medium, punch cards, papertape, any other physical medium with patterns of holes, a RAM, a PROM, an EPROM, a FLASH-EPROM, any other memory chip or cartridge, a carrier wave/pulse, or any other medium from which a computer, processor or other electronic device can read.

"Logic," as used herein, includes, but is not limited to, hardware, firmware, software and/or combinations of each to perform a function(s) or an action(s), and/or to cause a function or action from another component. For example, based on a desired application or needs, logic may include a software controlled microprocessor, discrete logic such as an application specific integrated circuit (ASIC), a programmed logic device, memory device containing instructions, or the like. Logic may also be fully embodied as software.

"Signal," as used herein, includes, but is not limited to, one or more electrical signals, analog or digital signals, one or more computer or processor instructions, messages, a bit or bit stream, or other means that can be received, transmitted, and/or detected.

"Software," as used herein, includes, but is not limited to, one or more computer readable and/or executable instructions that cause a computer or other electronic device to perform functions, actions, and/or behave in a desired manner. The instructions may be embodied in various forms such as routines, algorithms, modules or programs including separate applications or code from dynamically linked libraries. Software may also be implemented in various forms such as a stand-alone program, a function call, a servlet, an applet, instructions stored in memory, part of an operating system or other type of executable instructions. It will be appreciated by one of ordinary skill in the art that the form of software is dependent on, for example, requirements of a desired application, the environment it runs on, and/or the desires of a designer/programmer or the like. Suitable software for implementing the various components of the present system and method using the teachings presented here include programming languages and tools such as Java, Pascal, C#, C++, C, CGI, Perl, SQL, APIs, SDKs, assembly, firmware, microcode, and/or other languages and tools. The components embodied as software include readable/executable instructions that cause one or more computers, processors and/or other electronic device to behave in a prescribed manner. Any software, whether an entire system or a component of a system, may be embodied as an article of manufacture and maintained as part of a computer-readable medium as defined previously. Another form of the software may include signals that transmit program code of the software to a recipient over a network or other communication medium. It will be appreciated that components described herein may be implemented as separate components or may be combined together.

"User," as used herein, includes, but is not limited to, one or more persons, software, computers or other devices, or combinations of these.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A method of ablating and characterizing a scanned object in a patient, the method comprising:

directing a first ablative energy from an ablative element toward an anatomical wall of the scanned object while the ablative element is positioned adjacent to the anatomical wall, wherein the ablative element and an imaging apparatus are disposed on a catheter;

emitting, with the imaging apparatus, imaging energy toward the scanned object while the imaging apparatus is positioned adjacent to the anatomical wall;

receiving, at a processor in communication with the imaging apparatus, signals representative of reflections of the emitted imaging energy from the scanned object;

determining, with the processor, one or more signal properties of the scanned object from the signals representative of the reflections of the emitted imaging energy;

associating, with the processor, the one or more signal properties to pre-determined signal properties of a tissue component and a plurality of ablation levels for the tissue component;

identifying, with the processor and based on the associating, the tissue component of the anatomical wall and an ablation level of the tissue component resulting from the first ablative energy, wherein the anatomical wall comprises a wall of a blood vessel, wherein the ablation level is identified as a first ablation level of the plurality of ablation levels;

determining, based on the identifying, if ablation of the tissue component resulting from the first ablative energy is therapeutically effective; and directing, when the ablation is not therapeutically effective, a second ablative energy from the ablative element toward the anatomical wall to cause at least a second ablation level of the plurality of ablation levels for the tissue component.

2. The method of claim 1, wherein the pre-determined signal properties comprise branch node conditions based on the pre-determined signal properties and two or more leaf nodes identifying the tissue component and a second tissue component each having a respective level of ablation of the plurality of ablation levels.

3. The method of claim 1, wherein the signals include a plurality of backscattered scan lines and the determining step includes determining the one or more signal properties for a plurality of segments from the plurality of backscattered scan lines.

4. The method of claim 1, wherein the receiving step includes collecting the signals by a plurality of imaging modalities.

5. The method of claim 1, wherein the receiving step includes collecting the signals from at least one of a carotid body, vascular plaque, or a nerve.

6. The method of claim 1, wherein associating the one or more signal properties to the pre-determined signal properties of the tissue component includes selecting the pre-determined signal properties based on secondary parameters associated with the scanned object.

7. The method of claim 1, wherein the scanned object comprises a renal vessel.

8. A system, comprising:
a catheter including:
an imaging apparatus configured to emit imaging energy toward an object while the imaging apparatus is positioned adjacent to an anatomical wall of the object; and
an ablative element configured to direct ablative energy toward the anatomical wall while the ablative element is positioned adjacent to the anatomical wall; and
a processor in communication with the catheter and configured to:
control the ablative element to direct a first ablative energy toward the anatomical wall;
control the imaging apparatus to emit the imaging energy toward the object;
receive signals representative of reflections of the emitted imaging energy from the object;
determine one or more signal properties of the object from the signals representative of the reflections of the emitted imaging energy;
associate the one or more signal properties to pre-determined signal properties of a tissue component and a plurality of ablation levels for the tissue component; and
identify, based on the associating, the tissue component of the anatomical wall and an ablation level of the tissue component resulting from the first ablative energy, wherein the anatomical wall comprises a wall of a blood vessel, wherein the ablation level is identified as a first ablation level of the plurality of ablation levels;
determine, based on the identifying, if ablation of the tissue component resulting from the first ablative energy is therapeutically effective; and
control the ablative element to direct, when the ablation is not therapeutically effective, a second ablative energy toward the anatomical wall to cause at least a second ablation level of the plurality of ablation levels for the tissue component.

9. The system of claim 8, wherein the pre-determined signal properties comprise branch node conditions based on the pre-determined signal properties and two or more leaf nodes identifying the tissue component and a second tissue component each having a respective level of ablation of the plurality of ablation levels.

10. The system of claim 8, wherein the signals include a plurality of backscattered scan lines, and wherein the processor is configured to determine by determining the one or more signal properties for a plurality of segments from the plurality of backscattered scan lines.

11. The system of claim 8, wherein the processor is configured to receive reflected signals by collecting reflected signals by a plurality of imaging modalities.

12. The system of claim 8, wherein the catheter is sized to be positioned within a blood vessel and configured to scan at least one of a carotid body, vascular plaque, or a nerve while positioned within the blood vessel.

13. The system of claim 8, wherein the processor is configured to associate the one or more signal properties to the pre-determined signal properties of the tissue component by selecting the pre-determined tissue properties based on secondary parameters associated with the object.

14. The system of claim 8, wherein the catheter is sized to be positioned within a renal vessel.

15. The system of claim 8, wherein the imaging energy is ultrasound imaging energy.

16. The system of claim 8, wherein the pre-determined signal properties comprise classification conditions stored in a data structure.

17. The system of claim 8, wherein the processor is configured to identify the tissue component and a second tissue component of the anatomical wall.

* * * * *